(12) United States Patent
Bamberg et al.

(10) Patent No.: US 7,358,373 B2
(45) Date of Patent: Apr. 15, 2008

(54) CATHEPSIN K INHIBITORS

(75) Inventors: Joe Timothy Bamberg, East Palo Alto, CA (US); Tobias Gabriel, San Francisco, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 0 days.

(21) Appl. No.: 11/493,208

(22) Filed: Jul. 25, 2006

(65) Prior Publication Data

US 2007/0032484 A1 Feb. 8, 2007

Related U.S. Application Data

(60) Provisional application No. 60/702,937, filed on Jul. 27, 2005.

(51) Int. Cl.
C07D 209/12 (2006.01)
C07D 277/64 (2006.01)
C07D 275/04 (2006.01)

(52) U.S. Cl. .................. 548/492; 548/180; 548/207

(58) Field of Classification Search ................. 548/492
See application file for complete search history.

(56) References Cited

U.S. PATENT DOCUMENTS

| 6,531,612 B2 * | 3/2003 | Gabriel et al. ............. 548/452 |
| 6,759,428 B2 * | 7/2004 | Bamberg et al. ............ 514/419 |
| 7,173,051 B2 | 2/2007 | Liu et al. |
| 2004/0204368 A1 | 10/2004 | Ohmoto et al. |

FOREIGN PATENT DOCUMENTS

| EP | 1 234 820 | 8/2002 |
| EP | 1 254 898 A1 | 11/2002 |
| WO | WO 00/48993 A1 | 8/2000 |
| WO | WO 02/069901 A2 | 9/2002 |
| WO | WO 02/070517 A2 | 9/2002 |
| WO | WO 2004/084843 A2 | 10/2004 |
| WO | WO 2004/106285 | 12/2004 |

* cited by examiner

*Primary Examiner*—Rebecca Anderson
*Assistant Examiner*—Shawquia Young
(74) *Attorney, Agent, or Firm*—Robert C. Hall

(57) ABSTRACT

The present invention provides a compound of the Formula:

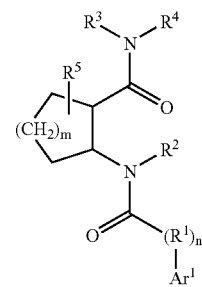

a pharmaceutically acceptable salt, a solvate, or a prodrug thereof, wherein m, n, $Ar^1$, $R^1$, $R^2$, $R^3$, $R^4$, and $R^5$ are those defined herein. The present invention also provides methods for using and preparing compounds of Formula I.

14 Claims, No Drawings

CATHEPSIN K INHIBITORS

CROSS-REFERENCE TO RELATED APPLICATIONS

This application claims the benefit of priority of U.S. Provisional Patent Application Ser. No. 60/702,937 filed Jul. 27, 2005, the disclosure of which is incorporated herein by reference in its entirety.

FIELD OF THE INVENTION

The invention relates to compounds of Formula I and methods for using and preparing the same.

BACKGROUND OF THE INVENTION

Cysteine proteases have been viewed as lysosomal mediators of terminal protein degradation. Several newly discovered members of this enzyme class, however, are regulated proteases with limited tissue expression, which implies specific roles in cellular physiology and thus would allow a specific targeting of these activities without interfering with the general lysosomal protein degradation. Development of inhibitors of specific cysteine proteases promises to provide new drugs for modifying immunity, osteoporosis, neurodegeneration, chronic inflammation, cancer and malaria (Brömme, Drug News Perspect 1999, 12(2), 73-82; Chapman et al., Annu. Rev. Phys. 1997, 59, 63-88).

Cysteine proteases can be grouped into two superfamilies: the family of enzymes related to interleukin 1β converting enzyme (ICE), and the papain superfamily of cysteine proteases. Presently there are at least 12 human proteases of the papain family from which sequences have been obtained (cathepsin B, L, H, S, O, K, C, W, F, V(L2), Z(X) and bleomycin hydrolase). Cathepsin K was first discovered as a cDNA prominent in rabbit osteoclasts and referred to as OC-2 (Tezuka et al., J. Biol. Chem. 1994, 269, 1106-1109). Recent observations indicate that cathepsin K is the most potent mammalian elastase yet described. Cathepsin K, as well as cathepsins S and L, are also potent collagenases and gelatinases. Macrophages appear capable of mobilizing the active proteases within endosomal and/or lysosomal compartments to the cell surface under special circumstances. In this case, the cell surface/substrate interface becomes a compartment from which endogenous inhibitors are excluded and can be viewed as a physiological extension of the lysosome. This type of physiology is an innate trait of osteoclasts, a bone macrophage, and may also be exploited by other macrophages or cells in the context of inflammation. The abundance of cathepsin K in osteoclasts leads to the suggestion that cathepsin K plays an important role in bone resorption. Studies revealed that cathepsin K is the predominant cysteine protease in osteoclasts and is specifically expressed in human osteoclasts. A correlation between inhibition of cysteine protease activity and bone resorption has been reported (Lerner et al., J. Bone Min. Res. 1992, 7, 433; Everts et al., J. Cell. Physiol. 1992, 150, 221). Cathepsin K has been detected in synovial fibroblasts of RA patients, as well as in mouse hypertrophic chondrocytes (Hummel et al., J. Rheumatol. 1998, 25(10), 1887-1894.). Both results indicate a direct role of cathepsin K in cartilage erosion. P. Libby (Libby et al., J. Clin. Invest. 1998, 102 (3), 576-583) reported that normal arteries contain little or no cathepsin K or S whereas macrophages in atheroma contained abundant immunoreactive cathepsins K and S. Most of the elastolytic activity of tissue extracts associated with human atheroma compared to non-atherosclerotic arteries could be inhibited with E64, a non-selective cysteine protease inhibitor.

Tumor progression and metastasis are characterized by the invasion of tumors into adjacent tissues as well as by the dissociation of cancer cells from primary tumors and the infiltration of metastatic cells into organs. These processes are associated with the degragation of extracellular matrix proteins and thus require proteolytic activity. Cathepsin K has been identified in primary breast tumors, as well as in breast tumor-derived bone metastasis (Littlewood-Evans et al., Cancer Res. 1997, 57, 5386-5390), and prostate cancer (Brubaker et al., Journal of Bone and Mineral Research 2003, 18(2), 222-230.

Different classes of compounds, such as aldehydes, alpha-ketocarbonyl compounds, halomethyl ketones, diazomethyl ketones, (acyloxy)methyl ketones, ketomethylsulfonium salts, epoxy succinyl compounds, vinyl sulfones, aminoketones, and hydrazides have been identified as cysteine protease inhibitors (Schirmeister et al., Chem. Rev. 1997, 97, 133-171; Veber et al., Proc. Natl. Acad. Sci. USA 1997, 94, 14249-14254). The shortcomings these compounds suffer from include lack of selectivity, poor solubility, rapid plasma clearance and cytotoxicity. A need therefore exists for novel inhibitors useful in treating diseases caused by pathological levels of proteases, especially cysteine proteases, including cathepsins, especially cathepsin K.

SUMMARY

One aspect of the invention provides compounds of the Formula:

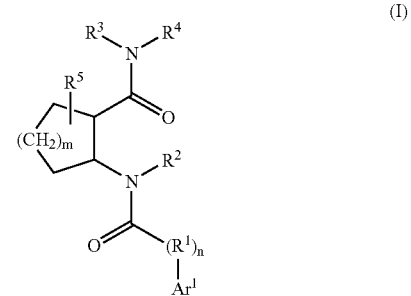

or pharmaceutically acceptable salts thereof,
wherein
m is an integer from 1 to 3;
n is 0 or 1;
$Ar^1$ is aryl, bi-aryl, or heteroaryl;
$R^1$ is alkylene;
each of $R^2$, $R^3$ and $R^5$ is independently hydrogen or alkyl; and
$R^4$ is aralkyl, cycloalkyl, heterocyclyl, heteroaralkyl, or —CH($R^6$)—$Z^1$, wherein
  $R^6$ is hydrogen, alkyl or heteroalkyl;
  $Z^1$ is —($CR^7R^8)_p$—$X^1$,
  wherein
    p is 1 or 2;
    $X^1$ is —$OR^{10}$ or —$NR^{10}R^{11}$;

wherein

R$^{10}$ is hydrogen, alkyl or heteroalkyl; and

R$^{11}$ is hydrogen, acetyl, alkyl, aryl, aralkyl, heteroaryl, —S(O)$_x$Ar$^2$, hydroxy, alkoxy, aralkoxy, —C(O)-aryl, —C(O)—O-aralkyl, or heteroalkoxy, wherein x is an integer from 0 to 2; and Ar$^2$ is aryl; or R$^{10}$ and R$^{11}$ together with the nitrogen atom to which they are attached may form a heterocyclyl;

each R$^7$ is independently hydrogen or alkyl;

each R$^8$ is independently hydrogen, alkyl, hydroxy, alkoxy, hydroxyalkyl, alkoxyalkyl or aryl; or Z$^1$ is —(CR$^9$)=X$^2$; wherein X$^2$ is O or NR$^{12}$;

wherein

R$^{12}$ is hydrogen, alkyl, alkoxy, aralkoxy, hydroxyalkyl, alkoxyalkyl, hydroxy, or —NH—C(=X$^3$)—R$^{13}$, wherein X$^3$ is O or S; and R$^{13}$ is alkyl, aryl, arylamino, or aralkylamino;

R$^9$ is hydrogen, alkyl, hydroxy, alkoxy, aralkoxyalkyl, heteroalkyl, heteroalkylamino, aryl, arylamino, or heteroaryl;

R$^6$ is hydrogen, alkyl, or heteroalkyl; or

R$^6$ and one of R$^7$ and R$^8$ together with the atoms to which they are attached may form cycloalkyl or heterocyclyl; or one of R$^6$ or R$^7$ together with one of R$^{10}$ or R$^{11}$ and the atoms to which they are attached form heterocyclyl or aryl-heterocyclyl; or one of R$^6$ or R$^9$ together with R$^{12}$ and the atoms to which they are attached form cycloalkyl, heterocyclyl, or aryl-heterocyclyl.

In one embodiment, Ar$^1$ is heteroaryl. Preferably, Ar$^1$ is selected from the group consisting of indolyl, benzothiazolyl, thienyl, and quinolinyl, each of which is optionally substituted. More preferably, Ar$^1$ is optionally substituted indolyl. And most preferably, Ar$^1$ is 1-methyl-1H-indol-2-yl.

In another embodiment, Ar$^1$ is aryl or bi-aryl. Preferably, Ar$^1$ is selected from the group consisting of phenyl, naphthyl, and biphenyl, each of which is optionally substituted.

In one particular embodiment, R$^4$ is aralkyl, cycloalkyl, or heteroaralkyl. Preferably, R$^4$ is selected from the group consisting of: 2-methoxybenzyl; 2-hydroxycyclohexyl; 2-hydroxycyclopentyl; 4-phenylbutyl; 3-phenylpropyl; 2-phenylethyl; pyridin-2-ylmethyl; isoquinolin-3-ylmethyl; quinolin-2-ylmethyl; 5,6,7,8-tetrahydroquinolin-2-ylmethyl; 1H-indol-2-ylmethyl; 2-pyridin-4-ylethyl; 2-pyridin-2-ylethyl; and 2-pyridin-3-ylethyl.

Preferably, m is 2.

Preferably, R$^2$ is hydrogen.

Preferably, R$^3$ is hydrogen.

A particularly preferred compound of the present invention is of the formula:

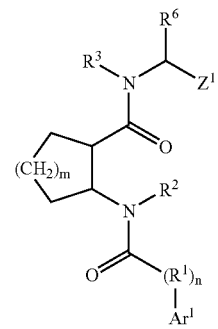

IA wherein m, n, R$^1$, R$^2$, R$^3$, R$^6$, Z$^1$, and Ar$^1$ are those defined herein.

In one embodiment, among compounds of Formula IA, one preferred group of compounds is where Z$^1$ is —(CR$^7$R$^8$)$_p$—X$^1$, and wherein p, R$^7$, R$^8$ and X$^1$ are those defined herein. Within compounds of this group, one preferred embodiment is a group of compounds where:

(I) p is 1; and (A) R$^6$, R$^7$, R$^8$ are hydrogen, and
  (i) X$^1$ is —OR$^{10}$, and R$^{10}$ is acy or phenyl; or
  (ii) X$^1$ is —NR$^{10}$R$^{11}$, wherein
    (a) R$^{10}$ is hydrogen and R$^{11}$ is:
      (1) 4-methoxyphenyl;
      (2) hydrogen;
      (3) benzyl;
      (4) phenyl;
      (5) benzoyl; or
      (6) —SO$_2$—AR$^2$, wherein Ar$^2$ is phenyl;
    (b) R$^{10}$ is methyl and R$^{11}$ is:
      (1) methyl; or
      (2) 4-methoxyphenyl; or
    (c) R$^{10}$ and R$^{11}$ together with nitrogen atom to which they are attached to form morpholino;

(B) R$^6$ is 2-hydroxyethyl, R$^7$ and R$^8$ are hydrogen and X$^1$ is hydroxy; or (C) R$^6$ and R$^8$ are hydrogen, and
  (i) R$^7$ is methyl and X$^1$ is hydroxy; or
  (ii) X$^1$ is —NR$^{10}$R$^{11}$, wherein R$^{10}$ is hydrogen, and R$^7$ together with R$^{11}$ and the atoms to which they are attached form 1,2,3,4-tetrahydroquinolin-2-yl;

(D) R$^6$ is 2-methylpropyl, R$^7$ and R$^8$ are hydrogen and X$^1$ is —NR$^{10}$R$^{11}$, wherein R$^{10}$ is hydrogen and R$^{11}$ is:
  (i) 2-phenylethyl;
  (ii) benzyl;
  (iii) 4-methoxyphenyl;
  (iv) phenyl;
  (v) 3-phenylpropyl;
  (vi) 4-phenylbutyl;
  (vii) pyridin-2-yl;
  (viii) pyridin-3-yl;
  (ix) 2H-pyrazol-3-yl;
  (x) 2-methylphenyl;
  (xi) 3-methylphenyl;
  (xii) 4-methylphenyl;
  (xiii) pyrrol-1-yl;
  (xiv) isoxazol-3-yl;
  (xv) 2H-tetrazol-5-yl; or
  (xvi) 4-chlorophenyl; or (E) $R^7$ and $R^8$ are hydrogen, and $X^1$ is $—NR^{10}R^{11}$, wherein
  (i) $R^{10}$ is benzyl, and $R^6$ together with $R^{11}$ and the atoms to which they are attached form pyrrolidinyl;
  (ii) $R^{10}$ is hydrogen, and $R^6$ together with $R^{11}$ and the atoms to which they are attached form pyrrolidin-3-yl; or
  (iii) $R^6$ is aminomethyl, $R^{10}$ is hydrogen and $R^{11}$ is 4-methoxyphenyl; or
(II) p is 2; and
  (A) $X^1$ is methoxy; $R^6$, $R^7$, and $R^8$ geminal to $X^1$ are hydrogen; and $R^8$ vicinal to $X^1$ is hydroxy; or
  (B) $R^6$, $R^7$, and $R^8$ are hydrogen; $X^1$ is $—NR^{10}R^{11}$, wherein $R^{10}$ and $R^{11}$ together with nitrogen atom to which they are attached to form morpholino.

In another embodiment, among compounds of Formula IA, another preferred group of compounds is where $Z^1$ is $—(CR^9)=X^2$, and wherein $R^9$ and $X^2$ are those defined herein. Within compounds of this group, one preferred embodiment is a group of compounds where:

(A) $X^2$ is O, and
  (a) $R^6$ and $R^9$ together form $—CH_2—CH_2—O—$ or $—(CH_2)_4—$;
  (b) $R^6$ is hydrogen and $R^9$ is:
    (i) methoxy
    (ii) hydroxy,
    (iii) methoxymethyl,
    (iv) methyl,
    (v) benzyloxymethyl,
    (vi) 3-nitrophenyl,
    (vii) phenyl,
    (viii) phenylamino,
    (ix) 4-methoxyphenylamino, or
    (x) 2-hydroxyamino,
  (c) $R^9$ is hydrogen and $R^6$ is:
    (i) 2-methylpropyl; or
    (ii) hydrogen;
  (d) $R^9$ is $—X^3—C(=X^4)—R^{13}$, wherein $X^3$ is NH, $X^4$ is O, and $R^{13}$ benzyloxy; or
  (e) $R^6$ is propyl and $R^9$ is benzooxazol-2-yl; or
(B) $X^2$ is $NR^{12}$; $R^6$ is 2-methylpropyl; and $R^{12}$ is:
  (a) hydroxy;
  (b) benzyloxy;
  (c) carboxymethoxy;
  (d) methoxy; or
  (e) $—NH—C(=X^3)—R^{13}$, wherein:
    (i) $X^3$ is O; and $R^{13}$ is:
      (1) phenylamino;
      (2) methyl; or
      (3) 4-chlorophenyl; or
    (ii) $X^3$ is S; and $R^{13}$ is benzylamino.

In certain embodiments of formula IA, the subject compounds may be represented by the formula IB:

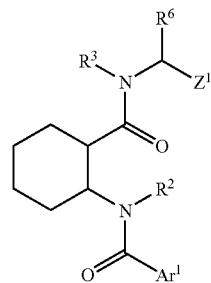

wherein n, $R^2$, $R^3$, $R^6$, $Z^1$, and $Ar^1$ are those defined herein.

Another preferred compound of the invention is a compound of the formula:

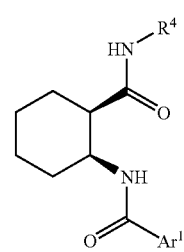

wherein $Ar^1$ and $R^4$ are as defined herein.

Still another preferred compound of the invention is a compound of the formula ID:

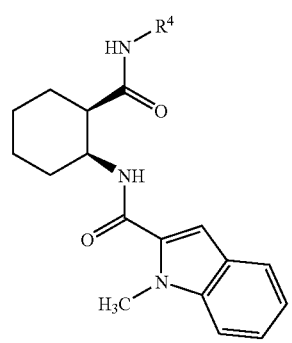

wherein $R^4$ is as defined herein. In certain embodiments of either of formulas IC or ID, $R^4$ may be a group selected from:

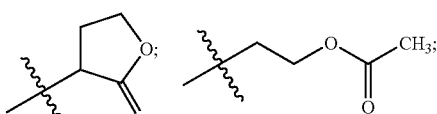

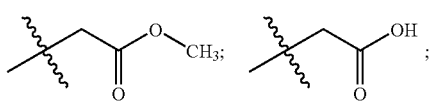

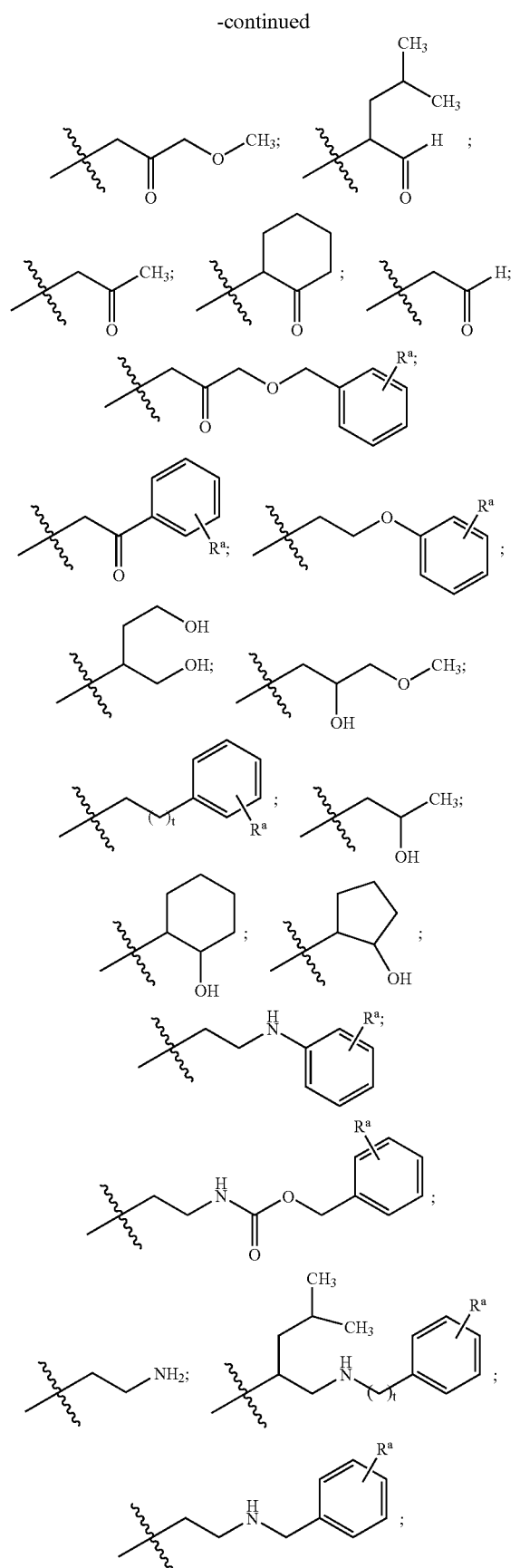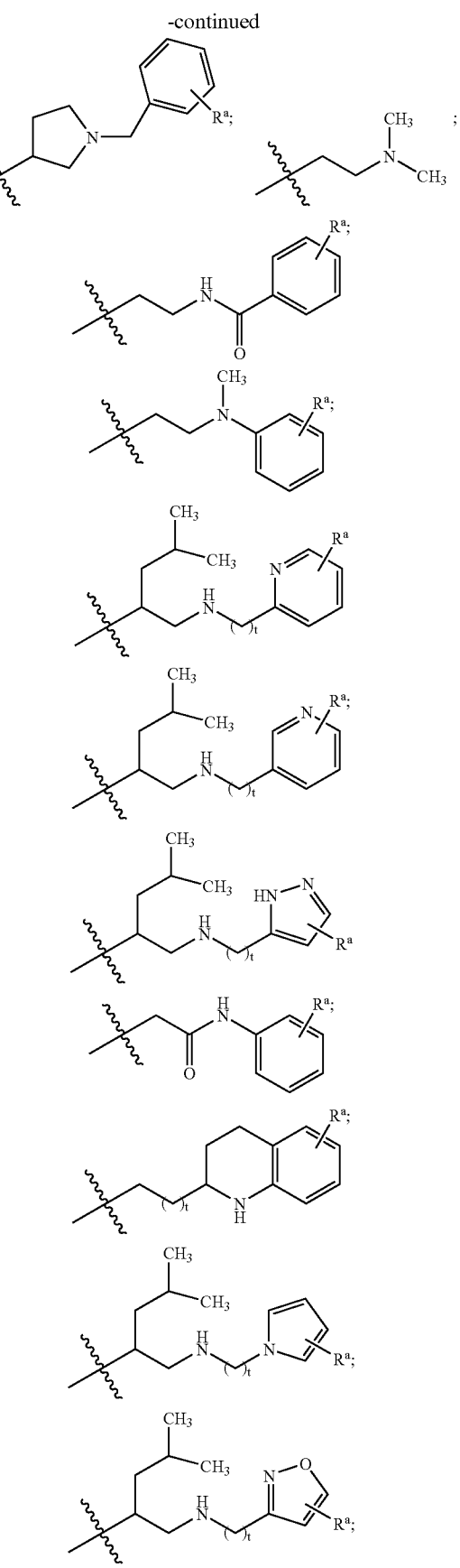

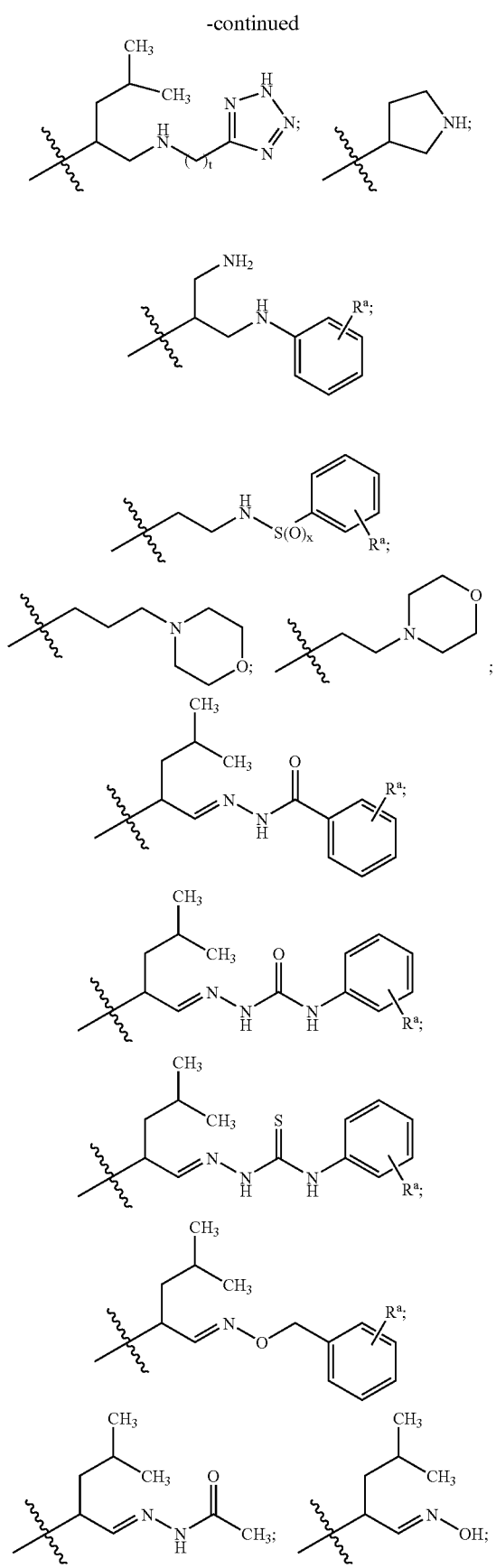
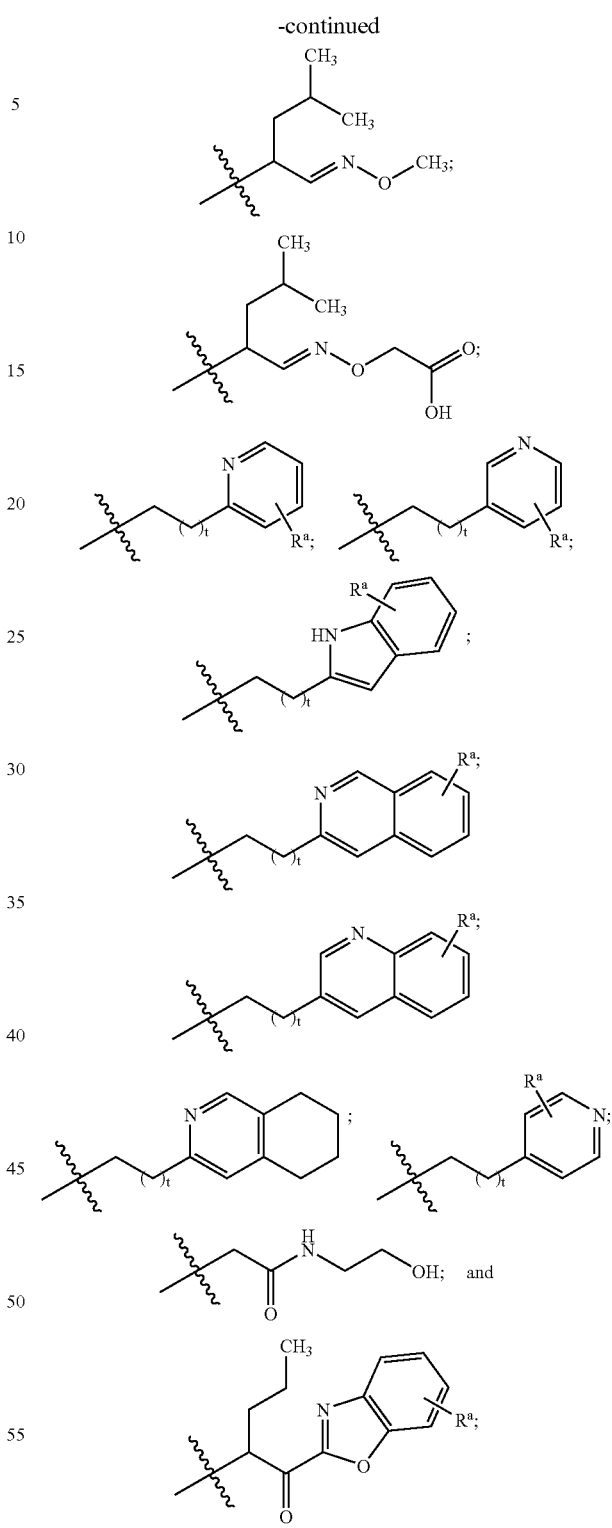
wherein t is from 0 to 4 and $R^a$ is hydrogen, alkyl, alkoxy, halo, haloalkyl, cyano or heteroalkyl. In many such embodiments t is 1 and $R^a$ is alkoxy or alkyl, preferably methoxy or methyl, and most preferably methoxy.
In certain embodiments of either of formula IC or ID, $R^4$ may be more specifically a group selected from:

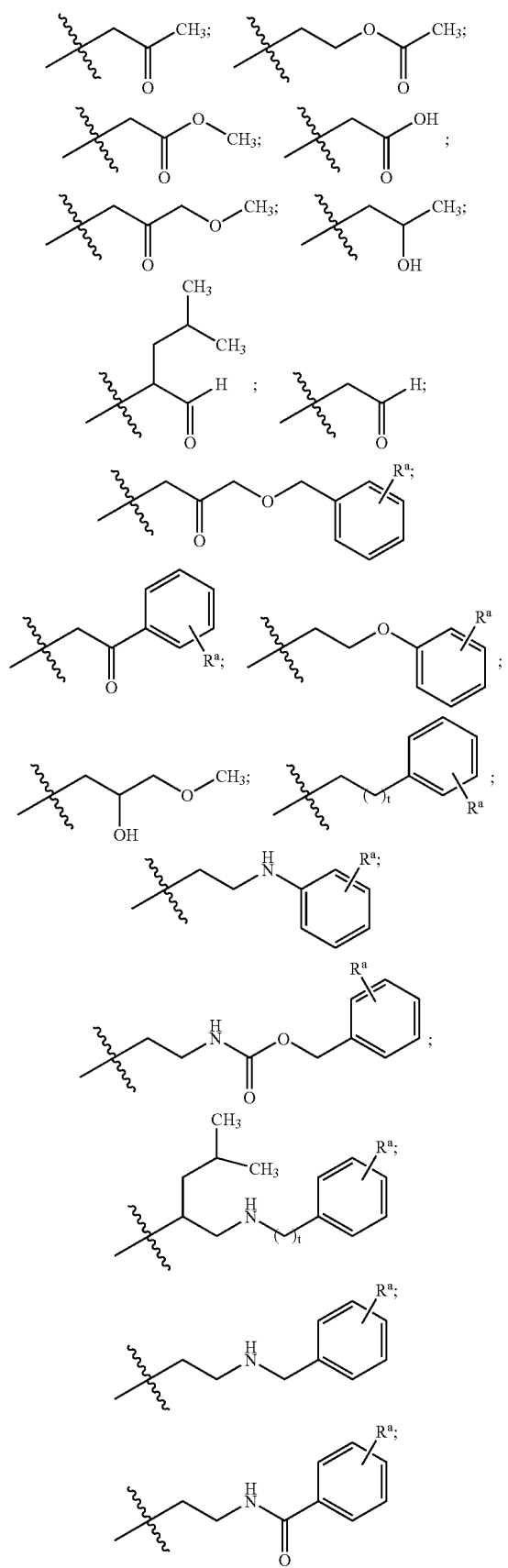
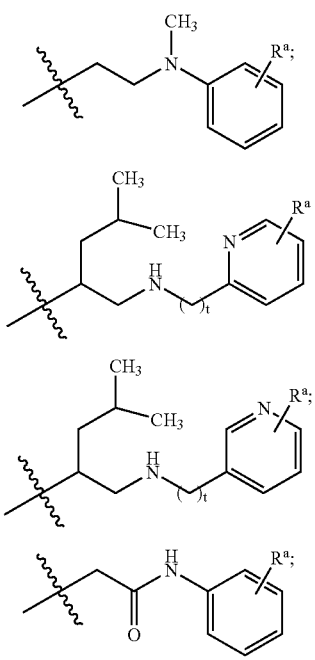
wherein t and $R^a$ are as defined herein.
In still other embodiments of either of formula IC or ID, $R^4$ may be selected from:
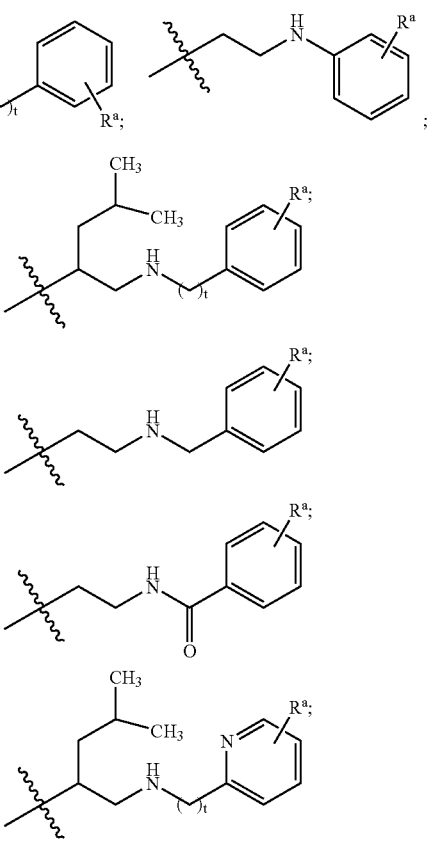

-continued

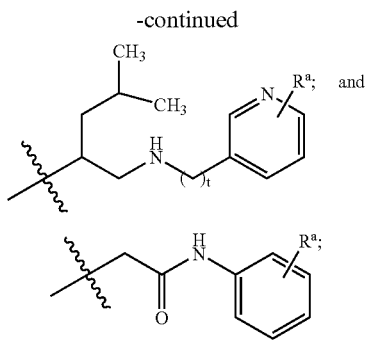

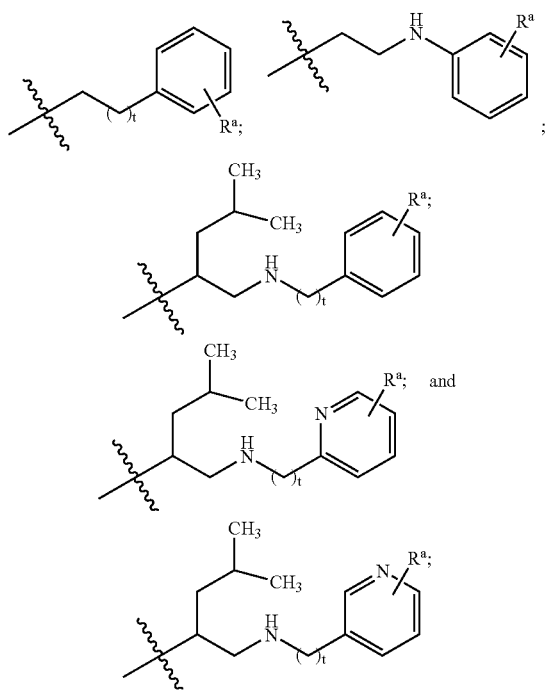

wherein t and R$^a$ are as defined herein. In many such embodiments t is 1 and R$^a$ is alkoxy or alkyl, preferably methoxy or methyl, and most preferably methoxy.

In yet other embodiments of either of formula IC or ID, R$^4$ may be selected from:

wherein t and R$^a$ are as defined herein. In many such embodiments t is 1 and R$^a$ is alkoxy or alkyl, preferably methoxy or methyl, and most preferably methoxy.

In certain embodiments of either of formula IC or ID, R$^4$ is

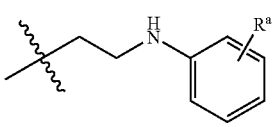

wherein R$^a$ is as defined herein.

In other embodiments of either formula IC or ID, R$^4$ is

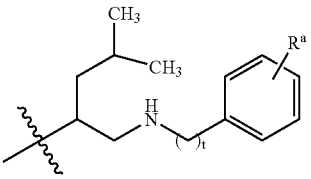

wherein t and R$^a$ are as defined herein.

In still other embodiments of either of formula IC or ID, R$^4$ is

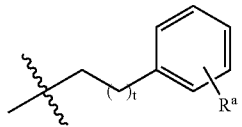

wherein t and R$^a$ are as defined herein.

A particularly preferred compound of Formula I is selected from the group consisting of:
1-methyl-1H-indole-2-carboxylic acid [(1S,2R)-2-((S)-2-oxo-tetrahydro-furan-3-ylcarbamoyl)-cyclohexyl]-amide;
acetic acid, 2-({(1R,2S)-2-[(1-methyl-1H-indole-2-carbonyl)-amino]-cyclohexanecarbonyl}-amino)-ethyl ester;
({(1R,2S)-2-[(1-methyl-1H-indole-2-carbonyl)-amino]-cyclohexanecarbonyl}-amino)-acetic acid methyl ester;
({(1R,2S)-2-[(1-methyl-1H-indole-2-carbonyl)-amino]-cyclohexanecarbonyl}-amino)-acetic acid;
1-methyl-1H-indole-2-carboxylic acid [(1S,2R)-2-(3-methoxy-2-oxo-propylcarbamoyl)-cyclohexyl]-amide;
1-methyl-1H-indole-2-carboxylic acid [(1S,2R)-2-((R)-1-formyl-3-methyl-butylcarbamoyl)-cyclohexyl]-amide;
1-Methyl-1H-indole-2-carboxylic acid [(1S,2R)-2-((S)-1-formyl-3-methyl-butylcarbamoyl)-cyclohexyl]-amide;
1-Methyl-1H-indole-2-carboxylic acid [(1S,2R)-2-(2-oxo-propylcarbamoyl)-cyclohexyl]-amide;
1-Methyl-1H-indole-2-carboxylic acid [(1S,2R)-2-((S)-2-oxo-cyclohexylcarbamoyl)-cyclohexyl]-amide;
1-Methyl-1H-indole-2-carboxylic acid [(1S,2R)-2-(2-oxo-ethylcarbamoyl)-cyclohexyl]-amide;
1-Methyl-1H-indole-2-carboxylic acid [(1S,2R)-2-(3-benzyloxy-2-oxo-propylcarbamoyl)-cyclohexyl]-amide;
1-Methyl-1H-indole-2-carboxylic acid {(1S,2R)-2-[2-(3-nitro-phenyl)-2-oxo-ethylcarbamoyl]-cyclohexyl}-amide;
1-Methyl-1H-indole-2-carboxylic acid [(1S,2R)-2-(2-oxo-2-phenyl-ethylcarbamoyl)-cyclohexyl]-amide;
1-Methyl-1H-indole-2-carboxylic acid [(1S,2R)-2-(2-phenoxy-ethylcarbamoyl)-cyclohexyl]-amide;
1-Methyl-1H-indole-2-carboxylic acid [(1S,2R)-2-((S)-3-hydroxy-1-hydroxymethyl-propylcarbamoyl)-cyclohexyl]-amide;
1-Methyl-1H-indole-2-carboxylic acid [(1S,2R)-2-(2-hydroxy-3-methoxy-propylcarbamoyl)-cyclohexyl]-amide;
1-Methyl-1H-indole-2-carboxylic acid [(1S,2R)-2-(2-methoxy-benzylcarbamoyl)-cyclohexyl]-amide;
1-Methyl-1H-indole-2-carboxylic acid [(1S,2R)-2-((R)-2-hydroxy-propylcarbamoyl)-cyclohexyl]-amide;
1-Methyl-1H-indole-2-carboxylic acid [(1S,2R)-2-((1S,2S)-2-hydroxy-cyclohexylcarbamoyl)-cyclohexyl]-amide;

1-Methyl-1H-indole-2-carboxylic acid [(1S,2R)-2-(2-hydroxy-cyclopentylcarbamoyl)-cyclohexyl]-amide;
1-Methyl-1H-indole-2-carboxylic acid {(1S,2R)-2-[2-(4-methoxy-phenylamino)-ethylcarbamoyl]-cyclohexyl}-amide;
N-{(1S,2R)-2-[2-(4-Methoxy-phenylamino)-ethylcarbamoyl]-cyclohexyl}-4-(3-pyridin-4-yl-propoxy)-benzamide;
[2-({(1R,2S)-2-[(1-Methyl-1H-indole-2-carbonyl)-amino]-cyclohexanecarbonyl}-amino)-ethyl]-carbamic acid benzyl ester;
1-Methyl-1H-indole-2-carboxylic acid [(1S,2R)-2-(2-amino-ethylcarbamoyl)-cyclohexyl]-amide;
1-Methyl-1H-indole-2-carboxylic acid {(1S,2R)-2-[3-methyl-1-(phenethylamino-methyl)-butylcarbamoyl]-cyclohexyl}-amide;
1-Methyl-1H-indole-2-carboxylic acid {(1S,2R)-2-[1-(benzylamino-methyl)-3-methyl-butylcarbamoyl]-cyclohexyl}-amide;
1-Methyl-1H-indole-2-carboxylic acid ((1S,2R)-2-{1-[(4-methoxy-phenylamino)-methyl]-3-methyl-butylcarbamoyl}-cyclohexyl)-amide;
1-Methyl-1H-indole-2-carboxylic acid [(1S,2R)-2-((S)-3-methyl-1-phenylaminomethyl-butylcarbamoyl)-cyclohexyl]-amide;
1-Methyl-1H-indole-2-carboxylic acid [(1S,2R)-2-(2-benzylamino-ethylcarbamoyl)-cyclohexyl]-amide;
1-Methyl-1H-indole-2-carboxylic acid [(1S,2R)-2-(2-dimethylamino-ethylcarbamoyl)-cyclohexyl]-amide;
1-Methyl-1H-indole-2-carboxylic acid [(1S,2R)-2-(2-phenylamino-ethylcarbamoyl)-cyclohexyl]-amide;
1-Methyl-1H-indole-2-carboxylic acid [(1S,2R)-2-(2-benzoylamino-ethylcarbamoyl)-cyclohexyl]-amide;
1-Methyl-1H-indole-2-carboxylic acid [(1S,2R)-2-(1-benzyl-pyrrolidin-3-ylcarbamoyl)-cyclohexyl]-amide;
1-Methyl-1H-indole-2-carboxylic acid ((1S,2R)-2-{2-[(4-methoxy-phenyl)-methyl-amino]-ethylcarbamoyl}-cyclohexyl)-amide;
1-Methyl-1H-indole-2-carboxylic acid ((1S,2R)-2-{3-methyl-1-[(3-phenyl-propylamino)-methyl]-butylcarbamoyl}-cyclohexyl)-amide;
1-Methyl-1H-indole-2-carboxylic acid ((1S,2R)-2-{3-methyl-1-[(4-phenyl-butylamino)-methyl]-butylcarbamoyl}-cyclohexyl)-amide;
1-Methyl-1H-indole-2-carboxylic acid {(1S,2R)-2-[3-methyl-1-(pyridin-2-ylaminomethyl)-butylcarbamoyl]-cyclohexyl}-amide;
1-Methyl-1H-indole-2-carboxylic acid {(1S,2R)-2-[3-methyl-1-(pyridin-3-ylaminomethyl)-butylcarbamoyl]-cyclohexyl}-amide;
1-Methyl-1H-indole-2-carboxylic acid ((1S,2R)-2-{3-methyl-1-[(2H-pyrazol-3-ylamino)-methyl]-butylcarbamoyl}-cyclohexyl)-amide;
1-Methyl-1H-indole-2-carboxylic acid [(1S,2R)-2-(phenylcarbamoylmethylcarbamoyl)-cyclohexyl]-amide;
1-Methyl-1H-indole-2-carboxylic acid ((1S,2R)-2-{[(4-methoxy-phenylcarbamoyl)-methyl]-carbamoyl}-cyclohexyl)-amide;
1-Methyl-1H-indole-2-carboxylic acid {(1S,2R)-2-[(1,2,3,4-tetrahydro-quinolin-2-ylmethyl)-carbamoyl]-cyclohexyl}-amide;
N-{(1S,2R)-2-[2-(4-Methoxy-phenylamino)-ethylcarbamoyl]-cyclohexyl}-4-(quinolin-4-ylmethoxy)-benzamide;
1H-Indole-2-carboxylic acid {(1S,2R)-2-[2-(4-methoxy-phenylamino)-ethylcarbamoyl]-cyclohexyl}-amide;
4-Methoxy-N-{(1S,2R)-2-[2-(4-methoxy-phenylamino)-ethylcarbamoyl]-cyclohexyl}-benzamide;
4-Chloro-N-{(1S,2R)-2-[2-(4-methoxy-phenylamino)-ethylcarbamoyl]-cyclohexyl}-benzamide;
Benzothiazole-6-carboxylic acid {(1S,2R)-2-[2-(4-methoxy-phenylamino)-ethylcarbamoyl]-cyclohexyl}-amide;
Thiophene-2-carboxylic acid {(1S,2R)-2-[2-(4-methoxy-phenylamino)-ethylcarbamoyl]-cyclohexyl}-amide;
Thiophene-3-carboxylic acid {(1S,2R)-2-[2-(4-methoxy-phenylamino)-ethylcarbamoyl]-cyclohexyl}-amide;
Naphthalene-2-carboxylic acid {(1S,2R)-2-[2-(4-methoxy-phenylamino)-ethylcarbamoyl]-cyclohexyl}-amide;
1-Methyl-1H-indole-2-carboxylic acid {(1S,2R)-2-[(S)-3-methyl-1-(o-tolylamino-methyl)-butylcarbamoyl]-cyclohexyl}-amide;
1-Methyl-1H-indole-2-carboxylic acid {(1S,2R)-2-[(S)-3-methyl-1-(m-tolylamino-methyl)-butylcarbamoyl]-cyclohexyl}-amide;
1-Methyl-1H-indole-2-carboxylic acid {(1S,2R)-2-[(S)-3-methyl-1-(p-tolylamino-methyl)-butylcarbamoyl]-cyclohexyl}-amide;
1-Methyl-1H-indole-2-carboxylic acid {(1S,2R)-2-[(S)-3-methyl-1-(pyrrol-1-ylaminomethyl)-butylcarbamoyl]-cyclohexyl}-amide;
1-Methyl-1H-indole-2-carboxylic acid {(1S,2R)-2-[(S)-1-(isoxazol-3-ylaminomethyl)-3-methyl-butylcarbamoyl]-cyclohexyl}-amide;
1-Methyl-1H-indole-2-carboxylic acid ((1S,2R)-2-{(S)-3-methyl-1-[(2H-tetrazol-5-ylamino)-methyl]-butylcarbamoyl}-cyclohexyl)-amide;
1-Methyl-1H-indole-2-carboxylic acid [(1S,2R)-2-((R)-3-methyl-1-phenylaminomethyl-butylcarbamoyl)-cyclohexyl]-amide;
1-Methyl-1H-indole-2-carboxylic acid [(1S,2R)-2-(pyrrolidin-3-ylcarbamoyl)-cyclohexyl]-amide;
1-Methyl-1H-indole-2-carboxylic acid ((1S,2R)-2-{(S)-1-[(4-chloro-phenylamino)-methyl]-3-methyl-butylcarbamoyl}-cyclohexyl)-amide;
4-(1Hydroxy-1-methyl-ethyl)-N-{(1S,2R)-2-[2-(4-methoxy-phenylamino)-ethylcarbamoyl]-cyclohexyl}-benzamide;
N-{(1S,2R)-2-[2-(4-Methoxy-phenylamino)-ethylcarbamoyl]-cyclohexyl}-benzamide;
Quinoline-3-carboxylic acid {(1S,2R)-2-[2-(4-methoxy-phenylamino)-ethylcarbamoyl]-cyclohexyl}-amide;
Quinoline-6-carboxylic acid {(1S,2R)-2-[2-(4-methoxy-phenylamino)-ethylcarbamoyl]-cyclohexyl}-amide;
4'-Hydroxy-biphenyl-4-carboxylic acid {(1S,2R)-2-[2-(4-methoxy-phenylamino)-ethylcarbamoyl]-cyclohexyl}-amide;
Biphenyl-4-carboxylic acid {(1S,2R)-2-[2-(4-methoxy-phenylamino)-ethylcarbamoyl]-cyclohexyl}-amide;
1H-Indole-5-carboxylic acid {(1S,2R)-2-[2-(4-methoxy-phenylamino)-ethylcarbamoyl]-cyclohexyl}-amide;
1-Methyl-1H-indole-2-carboxylic acid ((1S,2R)-2-{2-amino-1-[(4-methoxy-phenylamino)-methyl]ethylcarbamoyl}-cyclohexyl)-amide;
1-Methyl-1H-indole-2-carboxylic acid [(1S,2R)-2-(2-benzenesulfonylamino-ethylcarbamoyl)-cyclohexyl]-amide;
1-Methyl-1H-indole-2-carboxylic acid [(1S,2R)-2-(3-morpholin-4-yl-propylcarbamoyl)-cyclohexyl]-amide;
1-Methyl-1H-indole-2-carboxylic acid [(1S,2R)-2-(2-morpholin-4-yl-ethylcarbamoyl)-cyclohexyl]-amide;
1-Methyl-1H-indole-2-carboxylic acid {(1S,2R)-2-[1-(hydroxyimino-methyl)-3-methyl-butylcarbamoyl]-cyclohexyl}-amide;
1-Methyl-1H-indole-2-carboxylic acid ((1S,2R)-2-{1-[(anilinocarbonyl)hydrazono-methyl]-3-methyl-butylcarbamoyl}-cyclohexyl)-amide;

1-Methyl-1H-indole-2-carboxylic acid [(1S,2R)-2-(1-{[(benzylamino)carbonothioyl]hydrazono-methyl}-3-methyl-butylcarbamoyl)-cyclohexyl]-amide;

1-Methyl-1H-indole-2-carboxylic acid {(1S,2R)-2-[1-(benzyloxyimino-methyl)-3-methyl-butylcarbamoyl]-cyclohexyl}-amide;

1-Methyl-1H-indole-2-carboxylic acid {(1S,2R)-2-[1-(acetyl-hydrazonomethyl)-3-methyl-butylcarbamoyl]-cyclohexyl}-amide;

1-Methyl-1H-indole-2-carboxylic acid ((1S,2R)-2-{1-[(4-chloro-benzoyl)-hydrazonomethyl]-3-methyl-butylcarbamoyl}-cyclohexyl)-amide;

[4-Methyl-2-({(1R,2S)-2-[(1-methyl-1H-indole-2-carbonyl)-amino]-cyclohexanecarbonyl}-amino)-pent-(E)-ylidene-aminooxy]-acetic acid;

1-Methyl-1H-indole-2-carboxylic acid {(1S,2R)-2-[1-(methoxyimino-methyl)-3-methyl-butylcarbamoyl]-cyclohexyl}-amide;

1-Methyl-1H-indole-2-carboxylic acid [(1S,2R)-2-(4-phenyl-butylcarbamoyl)-cyclohexyl]-amide;

1-Methyl-1H-indole-2-carboxylic acid [(1S,2R)-2-(3-phenyl-propylcarbamoyl)-cyclohexyl]-amide;

1-Methyl-1H-indole-2-carboxylic acid ((1S,2R)-2-phenethylcarbamoyl-cyclohexyl)-amide;

1-Methyl-1H-indole-2-carboxylic acid {(1S,2R)-2-[(pyridin-2-ylmethyl)-carbamoyl]-cyclohexyl}-amide;

1-Methyl-1H-indole-2-carboxylic acid {(1S,2R)-2-[(isoquinolin-3-ylmethyl)-carbamoyl]-cyclohexyl}-amide;

1-Methyl-1H-indole-2-carboxylic acid {(1S,2R)-2-[(quinolin-2-ylmethyl)-carbamoyl]-cyclohexyl}-amide;

1-Methyl-1H-indole-2-carboxylic acid {(1S,2R)-2-[(5,6,7,8-tetrahydro-quinolin-2-ylmethyl)-carbamoyl]-cyclohexyl}-amide;

1-Methyl-1H-indole-2-carboxylic acid {(1S,2R)-2-[(1H-indol-2-ylmethyl)-carbamoyl]-cyclohexyl}-amide;

1-Methyl-1H-indole-2-carboxylic acid [(1S,2R)-2-(2-pyridin-4-yl-ethylcarbamoyl)-cyclohexyl]-amide;

1-Methyl-1H-indole-2-carboxylic acid [(1S,2R)-2-(2-pyridin-2-yl-ethylcarbamoyl)-cyclohexyl]-amide;

1-Methyl-1H-indole-2-carboxylic acid [(1S,2R)-2-(2-pyridin-3-yl-ethylcarbamoyl)-cyclohexyl]-amide;

1-Methyl-1H-indole-2-carboxylic acid ((1S,2R)-2-{[(2-hydroxy-ethylcarbamoyl)-methyl]-carbamoyl}-cyclohexyl)-amide; and 1-Methyl-1H-indole-2-carboxylic acid {(1S,2R)-2-[(S)-1-(benzooxazole-2-carbonyl)-butylcarbamoyl]-cyclohexyl}-amide.

Another aspect of the present invention provides a pharmaceutical composition comprising a compound of Formula I and a pharmaceutically acceptable carrier and/or adjuvant.

Yet another aspect of the present invention provides a method for the treatment of osteoporosis, tumor metastasis, instable angina pectoris and/or plaque rupture, which method comprises administering a compound of Formula I to a human being or animal.

Still another aspect of the present invention provides a method for the treatment of osteoporosis, tumor metastasis, instable angina pectoris and/or plaque rupture, comprising administering to a subject in need thereof an effective amount of a compound of Formula I in combination with an effective amount of a phosphonic acid or phosphonic ester selected from alendronic acid, cimadronic acid, clodronic acid, tiludronic acid, etidronic acid, ibandronic acid, risedronic acid, pyridronic acid, pamidronic acid, zolendronic acid, or a pharmaceutically acceptable salt or solvate thereof, or mixture thereof.

Further aspect of the present invention provides a pharmaceutical composition comprising a compound of Formula I and a phosphonic acid or phosphonic ester selected from alendronic acid, cimadronic acid, clodronic acid, tiludronic acid, etidronic acid, ibandronic acid, risedronic acid, pyridronic acid, pamidronic acid, zolendronic acid, or a pharmaceutically acceptable salt or solvate thereof, or mixture thereof.

Yet another aspect of the present invention provides a method of producing a compound of Formula I comprising:

(a) reacting a compound of the Formula:

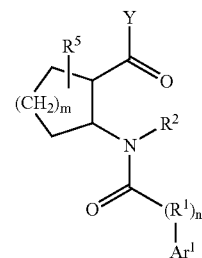

wherein

Y is a leaving group; and m, n, Ar$^1$, R$^1$, R$^2$, and R$^5$ are those defined herein;

with an amino compound of the Formula: HNR$^3$R$^4$, wherein R$^3$ and R$^4$ are those defined herein, to produce a compound of Formula I;

or (b) reacting a compound of Formula:

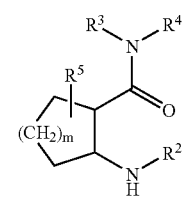

wherein m, R$^2$, R$^3$, R$^4$, and R$^5$ are those defined herein, with a compound of Formula:

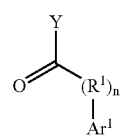

wherein

Y is a leaving group; and n, R$^1$, and Ar$^1$ are those defined herein, to produce a compound of Formula I.

DETAILED DESCRIPTION OF THE INVENTION

The compounds of the invention have an inhibitory activity on cysteine proteases, more particularly on cysteine proteases of the papain superfamily, even more particularly on cysteine proteases of the cathepsin family, most particularly on cathepsin K. It was surprisingly fond that this inhibiting effect on cathepsin K is selective with respect to other cathepsins. While compounds of Formula I very efficiently inhibit cathepsin K, the inhibition of other protease inhibitors such as cathepsin S, cathepsin L and cathepsin B is much weaker. Therefore, the compounds of Formula I are useful for specifically inhibiting cathepsin K. They can accordingly be used for the treatment of disorders which are associated with cysteine proteases such as osteoporosis, osteoarthritis, rheumatoid arthritis, tumor metastasis, glomerulonephritis, atherosclerosis, myocardial infarction, angina pectoris, instable angina pectoris, stroke, plaque rupture, transient ischemic attacks, amaurosis fugax, peripheral arterial occlusive disease, restenosis after angioplasty and stent placement, abdominal aortic aneurysm formation, inflammation, autoimmune disease, malaria, ocular fundus tissue cytopathy and respiratory disease.

Accordingly, other aspects of the present invention relate to a method for the prophylactic and/or therapeutic treatment of diseases which are associated with cystein proteases such as osteoporosis, osteoarthritis, rheumatoid arthritis, tumor metastasis, glomerulonephritis, atherosclerosis, myocardial infarction, angina pectoris, instable angina pectoris, stroke, plaque rupture, transient ischemic attacks, amaurosis fugax, peripheral arterial occlusive disease, restenosis after angioplasty and stent placement, abdominal aortic aneurysm formation, inflammation, autoimmune disease, malaria, ocular fundus tissue cytopathy and respiratory disease. Some methods of the present invention comprise administering a compound of Formula I to a human being or an animal.

Still other aspects of the present invention relate to pharmaceutical compositions comprising a compound of Formula I and a pharmaceutically acceptable carrier and/or adjuvant.

The present invention also relates to the use of such compounds for the preparation of medicaments for the treatment of disorders which are associated with cystein proteases. Yet other aspects of the present invention relate to processes for the preparation of the compounds of Formula I.

Definitions

Unless otherwise indicated the following definitions are set forth to illustrate and define the meaning and scope of the various terms used to describe the invention herein.

In this specification the term "lower" is used to mean a group consisting of one to seven, preferably of one to four carbon atom(s).

The term "alkyl" refers to a branched or straight chain monovalent saturated aliphatic hydrocarbon radical of one to eight carbon atoms.

The term "lower-alkyl" refers to a branched or straight chain monovalent alkyl radical of one to six carbon atoms, preferably one to four carbon atoms. This term is further exemplified by such radicals as methyl, ethyl, n-propyl, isopropyl, n-butyl, s-butyl, t-butyl and the like.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Cycloalkyl" means a monovalent saturated carbocyclic moiety consisting of mono- or bicyclic rings. Cycloalkyl can optionally be substituted with one or more substituents, wherein each substituent is independently hydroxy, alkyl, alkoxy, halo, haloalkyl, amino, monoalkylamino, or dialkylamino, unless otherwise specifically indicated. Examples of cycloalkyl moieties include, but are not limited to, cyclopropyl, cyclobutyl, cyclopentyl, cyclohexyl, cycloheptyl, and the like, including partially unsaturated derivatives thereof such as cyclohexenyl, cyclopentenyl, and the like.

"Cycloalkylalkyl" means a moiety of the formula —R'—R", where R' is alkylene and R" is cycloalkyl as defined herein.

"Alkylamino" or "monoalkylamino" means a radical —NHR where R represents an alkyl, cycloalkyl or cycloalkyl-alkyl group as defined herein. Representative examples include, but are not limited to methylamino, ethylamino, isopropylamino, cyclohexylamino, and the like.

"Dialkylamino" means a radical —NRR' where R and R' independently represent an alkyl, cycloalkyl, or cycloalkylalkyl group as defined herein. Representative examples include, but are not limited to dimethylamino, methyethylamino, di(1-methylethyl)amino, (cyclohexyl)(methyl)amino, (cyclohexyl)(ethyl)amino, (cyclohexyl)(propyl)amino, (cyclohexylmethyl)(methyl)amino, (cyclohexylmethyl)(ethyl)amino, and the like.

The term "halo" refers to fluorine, chlorine, bromine and iodine, with fluorine, chlorine and bromine being preferred.

"Haloalkyl" means alkyl substituted with one or more same or different halo atoms, e.g., —$CH_2Cl$, —$CF_3$, —$CH_2CF_3$, —$CH_2CCl_3$, and the like.

"Heteroalkyl" means an alkyl radical as defined herein wherein one, two or three hydrogen atoms have been replaced with a substituent independently selected from the group consisting of —$OR^a$, —$NR^bR^c$, and —$S(O)_nR^d$ (where n is an integer from 0 to 2), with the understanding that the point of attachment of the heteroalkyl radical is through a carbon atom, wherein $R^a$ is hydrogen, acyl, alkyl, aryl, aralkyl, cycloalkyl, or cycloalkylalkyl; $R^b$ and $R^c$ are independently of each other hydrogen, acyl, alkyl, aryl, aralkyl, cycloalkyl, or cycloalkylalkyl; when n is 0, $R^d$ is hydrogen, alkyl, cycloalkyl, or cycloalkylalkyl, and when n is 1 or 2, Rd is alkyl, cycloalkyl, cycloalkylalkyl, amino, acylamino, monoalkylamino, or dialkylamino. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like.

"Heteroaryl" means a monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring is optionally substituted independently with one or more substituents, preferably one or two substituents, selected from alkyl, haloalkyl, hydroxyalkyl, heteroalkyl, acyl, alkylene—C(O)—XR (where X is a bond, O or NR' (where R' is hydrogen or lower-alkyl) and R is hydrogen, alkyl, alkenyl, hydroxy, alkoxy, amino, monoalkylamino or dialkylamino) acylamino, amino, monoalkylamino, dialkylamino, NR'C(O)

OR" (where R' is hydrogen or alkyl and R" is alkyl or alkenyl), alkylthio, alkylsulfinyl, alkylsulfonyl, —SO₂NR'R" (where R' and R" are independently hydrogen, alkyl, cycloalkyl or cycloalkyl-alkyl), NRSO₂R' (where R is hydrogen or lower alkyl, and R' is alkyl, cycloalkyl, cycloalkyl-alkyl, amino, monoalkylamino or dialkylamino), alkoxy, haloalkoxy, alkoxycarbonyl, carbamoyl, hydroxy, halo, nitro, cyano, cyanoalkyl, mercapto, methylenedioxy, ethylenedioxy, benzyloxy, heterocyclyl-alkoxy or optionally substituted phenyl. Examples of heteroaryl moieties include, but are not limited to, optionally substituted imidazolyl, oxazolyl, isoxazolyl, thiazolyl, isothiazolyl, oxadiazolyl, thiadiazolyl, pyrazinyl, thienyl, benzothienyl, thiophenyl, furanyl, pyranyl, pyridyl, pyrrolyl, pyrazolyl, pyrimidyl, quinolinyl, isoquinolinyl, benzofuryl, benzothiophenyl, benzothiopyranyl, benzimidazolyl, benzooxazolyl, benzooxadiazolyl, benzothiazolyl, benzothiadiazolyl, benzopyranyl, indolyl, isoindolyl, triazolyl, triazinyl, quinoxalinyl, purinyl, quinazolinyl, quinolizinyl, naphthyridinyl, pteridinyl, carbazolyl, azepinyl, diazepinyl, acridinyl, thazinanyl and the like, including partially hydrogenated derivatives thereof.

"Heteroarylalkyl" and "heteroaralkyl", which may be used interchangeably, mean a radical —R$^a$R$^b$ where R$^a$ is an alkylene group and R$^b$ is heteroaryl group as defined herein; e.g., thienylmethyl, pyridinylmethyl, imidazolylethyl, pyrazolylpropyl, and the like are examples of heteroarylalkyl.

"Heterocyclyl" means a saturated or unsaturated non-aromatic cyclic radical of 3 to 8 ring atoms in which one or two ring atoms are heteroatoms selected from N, N(O), O, or S(O)$_n$ (where n is an integer from 0 to 2), the remaining ring atoms being C. The heterocyclyl ring may be optionally substituted independently with one, two, or three substituents selected from alkyl, haloalkyl, heteroalkyl, halo, nitro, cyanoalkyl, hydroxy, alkoxy, amino, monoalkylamino or dialkylamino. Examples of heterocyclyl moieties include but are not limited to, optionally substituted piperidinyl, piperazinyl, homopiperazinyl, azepinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, quinuclidinyl, quinolinyl, isoquinolinyl, benzimidazolyl, thiadiazolylidinyl, benzothiazolidinyl, benzoazolylidinyl, dihydrofuryl, tetrahydrofuryl, dihydropyranyl, tetrahydropyranyl, thiamorpholinyl, thiamorpholinylsulfoxide, thiamorpholinylsulfone, dihydroquinolinyl, dihydrisoquinolinyl, tetrahydroquinolinyl, tetrahydrisoquinolinyl, and the like, including partially unsaturated derivatives thereof.

"Heterocyclylalkyl" means a group —R$^x$—R$^y$ where R$^x$ is an alkylene group and R$^y$ is a heterocyclyl group. Representative examples include, but are not limited to, 2-(morpholin-4-yl)ethyl, 2-(4-methyl-piperazin-1-yl)ethyl, 3-(piperidin-1-yl)propyl and the like.

"Heterocyclyl-alkoxy" means a group —OR$^x$—R$^y$ were R$^x$ is an alkylene group and R$^y$ is a heterocyclyl group. Representative examples include, but are not limited to 2-(morpholin-4-yl)ethoxy, 2-(4-methyl-piperazin-1-yl) ethoxy and the like.

"Hydroxyalkyl" means an alkyl radical as defined herein, substituted with one or more, preferably one, two or three hydroxy groups, provided that the same carbon atom does not carry more than one hydroxy group. Representative examples include, but are not limited to, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxypropyl, preferably 2-hydroxyethyl, 2,3-dihydroxypropyl and 1-(hydroxymethyl)-2-hydroxyethyl. Accordingly, as used herein, the term "hydroxyalkyl" is used to define a subset of heteroalkyl groups.

The term "alkoxy" refers to the group —OR', wherein R' is an alkyl. The term "lower-alkoxy" refers to the group —OR', wherein R' is a lower-alkyl.

The term "alkenyl" stands for alone or in combination with other groups, a straight-chain or branched hydrocarbon residue containing an olefinic bond and up to 20, preferably up to 16 C-atoms. The term "lower-alkenyl" refers to a straight-chain or branched hydrocarbon residue containing an olefinic bond and up to 7, preferably up to 4 C-atoms.

"Aryl" means a monocyclic or bicyclic ("bi-aryl") aromatic hydrocarbon radical which is optionally substituted with one or more substituents, preferably one, two or three, substituents preferably selected from the group consisting of alkyl, haloalkyl, hydroxyalkyl, heteroalkyl, acyl, acylamino, amino, alkylamino, dialkylamino, alkylthio, alkylsulfinyl, alkylsulfonyl, —SO₂NR'R" (where R' and R" are independently hydrogen or alkyl), alkoxy, haloalkoxy, alkoxycarbonyl, carbamoyl, hydroxy, halo, nitro, cyano, mercapto, methylenedioxy or ethylenedioxy. More specifically the term aryl includes, but is not limited to, phenyl, chlorophenyl, fluorophenyl, methoxyphenyl, 1-naphthyl, 2-naphthyl, and the derivatives thereof.

"Arylalkyl" and "Aralkyl", which may be used interchangeably, means a radical —R$^a$R$^b$ where R$^a$ is an alkylene group and R$^b$ is an aryl group as defined herein; e.g., benzyl, phenylethyl, 3-(3-chlorophenyl)-2-methylpentyl, and the like are examples of arylalkyl.

"Aryl-heterocyclyl" means a fused bicyclic or tricyclic moiety having at least one heterocyclyl group and at least one aryl group with the understanding that the point of attachment is on the heterocyclyl group.

"Bi-aryl" means an aryl moiety that is substituted with another aryl group.

The term "pharmaceutically acceptable salts" embraces salts of the compounds of Formula I with inorganic or organic acids such as hydrochloric acid, hydrobromic acid, nitric acid, sulphuric acid, phosphoric acid, citric acid, formic acid, maleic acid, acetic acid, succinic acid, tartaric acid, methanesulphonic acid, p-toluenesulphonic acid and the like, which are relatively non toxic to living organisms at an amount that is used in preparation of pharmaceutical salts.

The term "pharmaceutically acceptable esters" embraces esters of the compounds of formula (I), in which hydroxy groups have been converted to the corresponding esters with inorganic or organic acids such as hydrochloric acid, hydrobromic acid, nitric acid, sulphuric acid, phosphoric acid, citric acid, formic acid, maleic acid, acetic acid, succinic acid, tartaric acid, methanesulphonic acid, p-toluenesulphonic acid and the like, which are non toxic to living organisms.

All references, patents and publications sited in this disclosure are incorporated herein by reference in their entirety.

Nomenclature and Chemical Structures

In general, the nomenclature used in this Application is based on AutoNom®, a Beilstein Institute computerized system for the generation of IUPAC systematic nomenclature. Chemical structures shown herein were prepared using ISIS® Draw version 2.5. Any open valency shown on a carbon, nitrogen or oxygen in the structures herein indicates the presence of a hydrogen.

Compounds

One aspect of the present invention provides a compound of the formula:

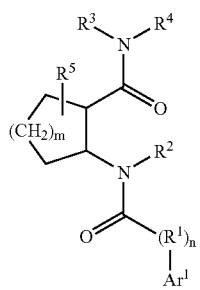

I or pharmaceutically acceptable salts thereof,
wherein
m is an integer from 1 to 3;
n is 0 or 1;
$Ar^1$ is aryl, bi-aryl, or heteroaryl;
$R^1$ is alkylene;
each of $R^2$, $R^3$ and $R^5$ is independently hydrogen or alkyl; and
$R^4$ is aralkyl, cycloalkyl, heterocyclyl, heteroaralkyl, or —CH($R^6$)—$Z^1$, wherein
  $R^6$ is hydrogen, alkyl or heteroalkyl;
  $Z^1$ is —$(CR^7R^8)_p$—$X^1$,
  wherein
    p is 1 or 2;
    $X^1$ is —$OR^{10}$ or —$NR^{10}R^{11}$;
    wherein
      $R^{10}$ is hydrogen, alkyl or heteroalkyl; and
      $R^{11}$ is hydrogen, acetyl, alkyl, aryl, aralkyl, heteroaryl, —$S(O)_xAr^2$, hydroxy, alkoxy, aralkoxy, —C(O)-aryl, —C(O)—O-aralkyl, or heteroalkoxy,
      wherein
        x is an integer from 0 to 2; and
        $Ar^2$ is aryl; or
      $R^{10}$ and $R^{11}$ together with the nitrogen atom to which they are attached may form a heterocyclyl;
    each $R^7$ is independently hydrogen or alkyl;
    each $R^8$ is independently hydrogen, alkyl, hydroxy, alkoxy, hydroxyalkyl, alkoxyalkyl or aryl; or
  $Z^1$ is —$(CR^9)=X^2$; wherein
    $X^2$ is O or $NR^{12}$;
    wherein
      $R^{12}$ is hydrogen, alkyl, alkoxy, aralkoxy, hydroxyalkyl, alkoxyalkyl, hydroxy, or —NH—C(=$X^3$)—$R^{13}$,
      wherein
        $X^3$ is O or S; and
        $R^{13}$ is alkyl, aryl, arylamino, or aralkylamino;
    $R^9$ is hydrogen, alkyl, hydroxy, alkoxy, aralkoxyalkyl, heteroalkyl, heteroalkylamino, aryl, arylamino, or heteroaryl;
  $R^6$ is hydrogen, alkyl, or heteroalkyl; or
  $R^6$ and one of $R^7$ and $R^8$ together with the atoms to which they are attached may form cycloalkyl or heterocyclyl; or
  one of $R^6$ or $R^7$ together with one of $R^{10}$ or $R^{11}$ and the atoms to which they are attached form heterocyclyl or aryl-heterocyclyl; or
  one of $R^6$ or $R^9$ together with $R^{12}$ and the atoms to which they are attached form cycloalkyl, heterocyclyl, or aryl-heterocyclyl.

In one embodiment, $Ar^1$ is heteroaryl. Preferably, $Ar^1$ is selected from the group consisting of indolyl, benzothiazolyl, thienyl, and quinolinyl, each of which is optionally substituted. More preferred heteroaryl of $Ar^1$ is optionally substituted indolyl with 1-methyl-1H-indol-2-yl being an especially preferred heteroaryl of $Ar^1$.

In another embodiment, $Ar^1$ is aryl or bi-aryl. Preferred aryls and bi-aryls include phenyl, naphthyl, and biphenyl, each of which is optionally substituted.

Still in another embodiment, m is 2.

In some embodiments, $R^2$ is hydrogen.

Yet in other embodiments, $R^3$ is hydrogen.

In another embodiment, $R^4$ is aralkyl, cycloalkyl, or heteroaralkyl. Preferably, $R^4$ is selected from the group consisting of phenylalkyl, cyclohexyl, cyclopentyl, pyridinylalkyl, isoquinolinylalkyl, quinolinylalkyl, 5,6,7,8-tetrahydroquinolinylalkyl, and 1H-indolylalkyl, wherein each of aryl, cycloalkyl and heteroaryl group is optionally substituted. More preferably, $R^4$ is selected from the group consisting of 2-methoxybenzyl, 2-hydroxycyclohexyl, 2-hydroxycyclopentyl, 4-phenylbutyl, 3-phenylpropyl, 2-phenylethyl, pyridin-2-ylmethyl, isoquinolin-3-ylmethyl, quinolin-2-ylmethyl, 5,6,7,8-tetrahydroquinolin-2-ylmethyl, 1H-indol-2-ylmethyl, 2-pyridin-4-ylethyl, 2-pyridin-2-ylethyl, and 2-pyridin-3-ylethyl.

Still in another embodiment, $R^4$ is —CH($R^6$)—$Z^1$, where $R^6$ and $Z^1$ are as defined herein.

In one particular embodiment, $Z^1$ is —$(CR^7R^8)_p$—$X^1$ where p, $R^7$, $R^8$ and $X^1$ are as defined herein.

Yet in another embodiment, $X^1$ is —$NR^{10}R^{11}$, where $R^{10}$ and $R^{11}$ are as defined herein. Within this group of compounds, in one particular embodiment, $R^{10}$ is hydrogen, and $R^7$ together with $R^{11}$ and the atoms to which they are attached form 1,2,3,4-tetrahydroquinolin-2-yl. Still in other embodiments within this group of compounds, $R^{10}$ is benzyl, and $R^6$ together with $R^{11}$ and the atoms to which they are attached form pyrrolidinyl. Yet in other compounds within this group of compounds, $R^{10}$ is hydrogen, and $R^6$ together with $R^{11}$ and the atoms to which they are attached form pyrrolidin-3-yl. Still yet other embodiments within this group of compounds, $R^6$ is aminomethyl, $R^{10}$ is hydrogen and $R^{11}$ is 4-methoxyphenyl. In other embodiments within this group of compounds, $R^{10}$ and $R^{11}$ together with nitrogen atom to which they are attached to form morpholino.

Yet in another embodiment, $Z^1$ is —$(CR^9)=X^2$, where $R^9$ and $X^2$ are as defined herein. Within this group of compounds, in one particular embodiment, $X^2$ is O. Still in other embodiments within this group of compounds, $X^2$ is $NR^{12}$, where $R^{12}$ is as defined herein.

Preferably $R^5$ is hydrogen.

In some embodiments, $R^6$ is hydrogen, 2-hydroxyethyl, 2-methylpropyl, aminomethyl, 2-methylpropyl, propyl, or 2-methylpropyl.

Still in other embodiments, $R^7$ is hydrogen or methyl.

Yet in other embodiments, $R^8$ is selected from the group consisting of hydrogen or hydroxy.

In other embodiments, $R^9$ is hydrogen, methoxy, hydroxy, methoxymethyl, methyl, benzyloxymethyl, 3-nitrophenyl, phenyl, phenylamino, 4-methoxyphenylamino, 2-hydroxyamino, or benzooxazol-2-yl.

Still in other embodiments, $R^{10}$ is hydrogen, acyl or phenyl, methyl, or benzyl.

Yet in another embodiment, $R^{11}$ is hydrogen, 4-methoxyphenyl, benzyl, phenyl, benzoyl, or —SO$_2$—Ar$^2$ (wherein Ar$^2$ is optionally substituted aryl, preferably phenyl), methyl, 4-methoxyphenyl, 2-phenylethyl, benzyl, 4-methoxyphenyl, phenyl, 3-phenylpropyl, 4-phenylbutyl, pyridin-2-yl, pyridin-3-yl, 2H-pyrazol-3-yl, 2-methylphenyl, 3-methylphenyl, 4-methylphenyl, pyrrol-1-yl, isoxazol-3-yl, 2H-tetrazol-5-yl, or 4-chlorophenyl.

Still in another embodiment, $R^{12}$ is hydroxy, benzyloxy, carboxymethoxy, methoxy, or —NH—C(=X$^3$)—R$^{13}$, where X$^3$ and R$^{13}$ are as defined herein.

Yet in other embodiments, $R^{13}$ is benzyloxy, phenylamino, methyl, 4-chlorophenyl, or benzylamino.

Still in other embodiments, $R^{14}$ is hydrogen.

In one embodiment, n is 0. This is particularly preferred when Ar$^1$ is heteroaryl.

Still further, combinations of the different variations of substituent groups described herein form other embodiments. For example, in one particularly example Ar$^1$ is 1-methyl-1H-indol-2-yl; n is 0; m is 2; $R^2$, $R^3$, and $R^5$ are hydrogen; and $R^4$ is —CH(R$^6$)—Z$^1$, where $R^6$ is hydrogen and $Z^1$ is —(CR$^9$)=X$^2$, where $R^9$ is methoxy and X$^2$ is O. In this manner, a variety of different compounds are embodied within the present invention.

Representative compounds in accordance with the invention are shown in Table 1. The Experimental Methods associated with preparation of the individual compounds are referenced in Table 1.

TABLE 1

| # | Structure | Method | Name (Autonom) |
|---|---|---|---|
| 1 | 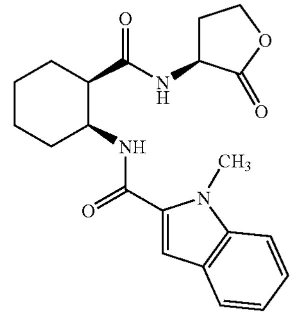 | A | 1-Methyl-1H-indole-2-carboxylic acid [(1S,2R)-2-((S)-2-oxo-tetrahydro-furan-3-ylcarbamoyl)-cyclohexyl]-amide |
| 2 | 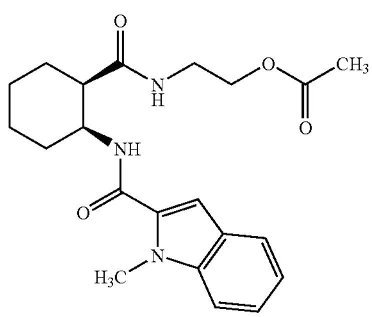 | A, J | Acetic acid 2-({(1R,2S)-2-[(1-methyl-1H-indole-2-carbonyl)-amino]-cyclohexanecarbonyl}-amino)-ethyl ester |
| 3 | 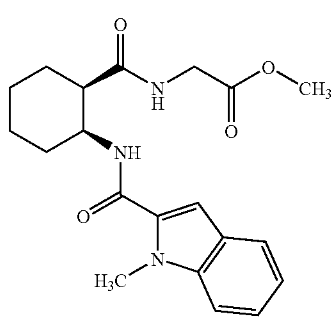 | A | ({(1R,2S)-2-[(1-Methyl-1H-indole-2-carbonyl)-amino]-cyclohexanecarbonyl}-amino)-acetic acid methyl ester |

TABLE 1-continued

| # | Structure | Method | Name (Autonom) |
|---|---|---|---|
| 4 | 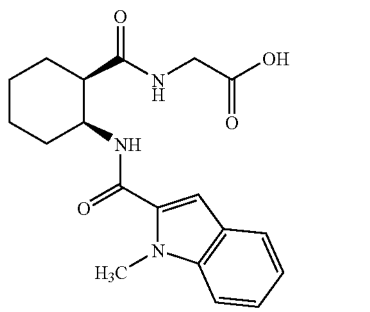 | A, R | ({(1R,2S)-2-[(1-Methyl-1H-indole-2-carbonyl)-amino]-cyclohexanecarbonyl}-amino)-acetic acid |
| 5 | 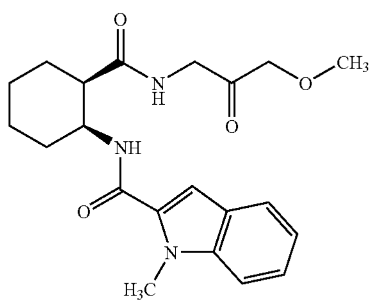 | A, F | 1-Methyl-1H-indole-2-carboxylic acid [(1S,2R)-2-(3-methoxy-2-oxo-propylcarbamoyl)-cyclohexyl]-amide |
| 6 | 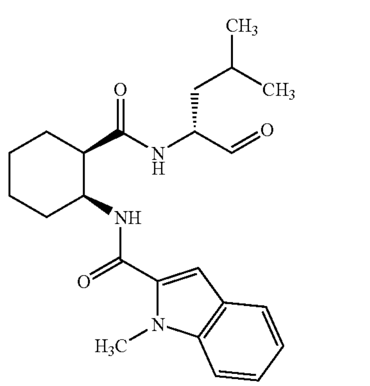 | A, F | 1-Methyl-1H-indole-2-carboxylic acid [(1S,2R)-2-((R)-1-formyl-3-methyl-butylcarbamoyl)-cyclohexyl]-amide |
| 7 | 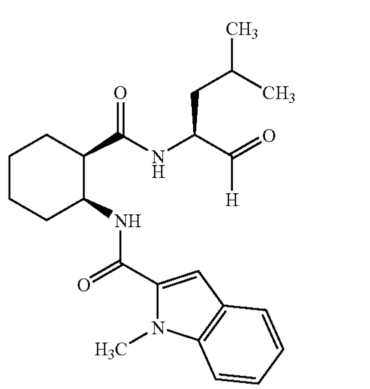 | A, F | 1-Methyl-1H-indole-2-carboxylic acid [(1S,2R)-2-((S)-1-formyl-3-methyl-butylcarbamoyl)-cyclohexyl]-amide |

TABLE 1-continued

| # | Structure | Method | Name (Autonom) |
|---|---|---|---|
| 8 | 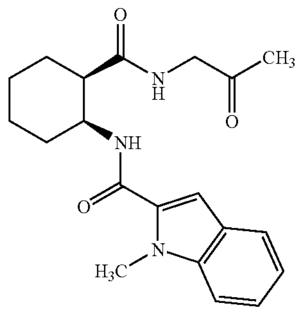 | A, E | 1-Methyl-1H-indole-2-carboxylic acid [(1S,2R)-2-(2-oxo-propylcarbamoyl)-cyclohexyl]-amide |
| 9 | 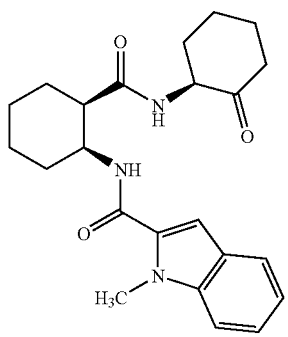 | A, E | 1-Methyl-1H-indole-2-carboxylic acid [(1S,2R)-2-((S)-2-oxo-cyclohexylcarbamoyl)-cyclohexyl]-amide |
| 10 | 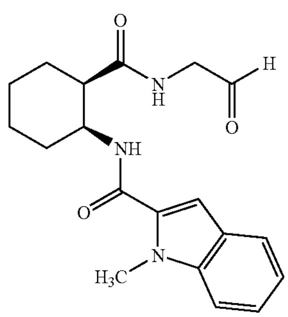 | A, E | 1-Methyl-1H-indole-2-carboxylic acid [(1S,2R)-2-(2-oxo-ethylcarbamoyl)-cyclohexyl]-amide |
| 11 | 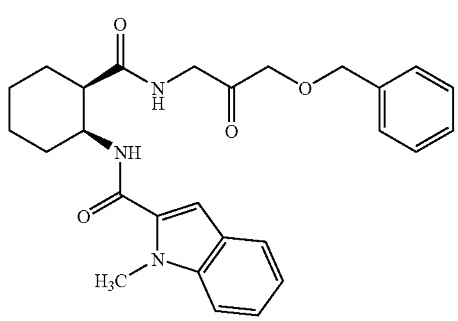 | A, E | 1-Methyl-1H-indole-2-carboxylic acid [(1S,2R)-2-(3-benzyloxy-2-oxo-propylcarbamoyl)-cyclohexyl]-amide |

TABLE 1-continued

| # | Structure | Method | Name (Autonom) |
|---|---|---|---|
| 12 | 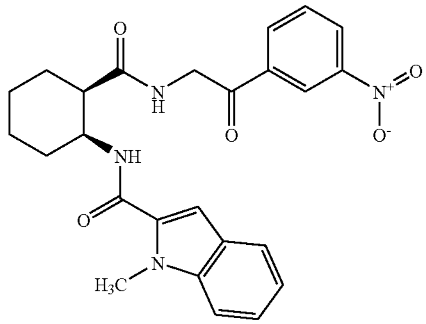 | A | 1-Methyl-1H-indole-2-carboxylic acid {(1S,2R)-2-[2-(3-nitro-phenyl)-2-oxo-ethylcarbamoyl]-cyclohexyl}-amide |
| 13 | 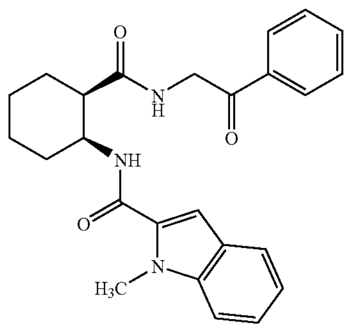 | A | 1-Methyl-1H-indole-2-carboxylic acid [(1S,2R)-2-(2-oxo-2-phenyl-ethylcarbomoyl)-cyclohexyl]-amide |
| 14 | 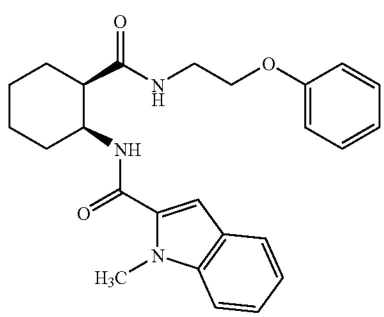 | A | 1-Methyl-1H-indole-2-carboxylic acid [(1S,2R)-2-(2-phenoxy-ethylcarbamoyl)-cyclohexyl]-amide |
| 15 | 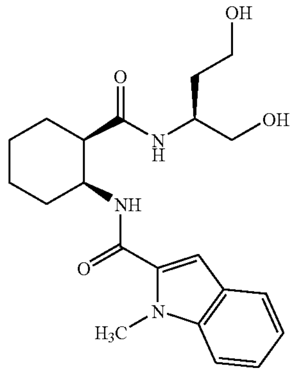 | A, B | 1-Methyl-1H-indole-2-carboxylic acid [(1S,2R)-2-((S)-3-hydroxy-1-hydroxymethyl-propylcarbamoyl)-cyclohexyl]-amide |

TABLE 1-continued

| # | Structure | Method | Name (Autonom) |
|---|---|---|---|
| 16 | 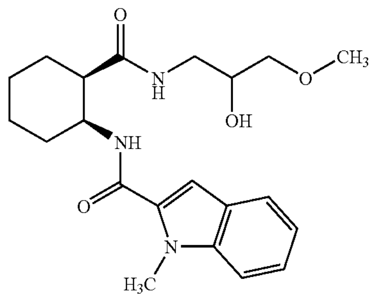 | A | 1-Methyl-1H-indole-2-carboxylic acid [(1S,2R)-2-(2-hydroxy-3-methoxy-propylcarbamoyl)-cyclohexyl]-amide |
| 17 | 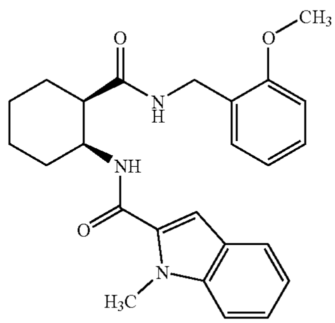 | A | 1-Methyl-1H-indole-2-carboxylic acid [(1S,2R)-2-(2-methoxy-benzylcarbamoyl)-cyclohexyl]-amide |
| 18 | 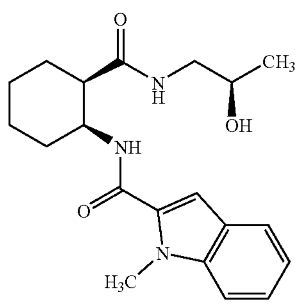 | A | 1-Methyl-1H-indole-2-carboxylic acid [(1S,2R)-2-((R)-2-hydroxy-propylcarbamoyl)-cyclohexyl]-amide |
| 19 | 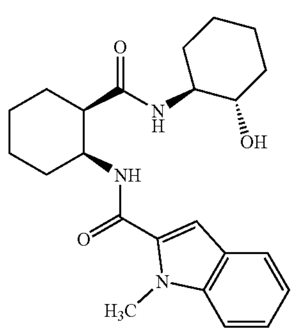 | A | 1-Methyl-1H-indole-2-carboxylic acid [(1S,2R)-2-((1S,2S)-2-hydroxy-cyclohexylcarbamoyl)-cyclohexyl]-amide |
| 20 | 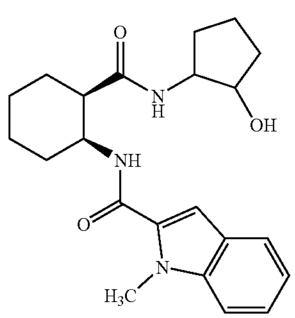 | A | 1-Methyl-1H-indole-2-carboxylic acid [(1S,2R)-2-(2-hydroxy-cyclopentylcarbamoyl)-cyclohexyl]-amide |

TABLE 1-continued

| # | Structure | Method | Name (Autonom) |
|---|---|---|---|
| 21 | 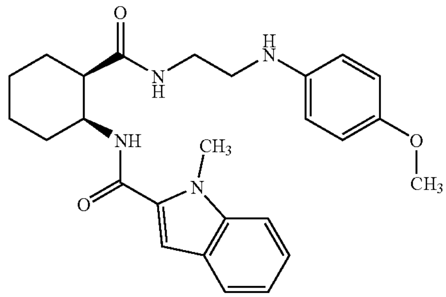 | A | 1-Methyl-1H-indole-2-carboxylic acid {(1S,2R)-2-[2-(4-methoxy-phenylamino)-ethylcarbamoyl]-cyclohexyl}-amide |
| 22 | 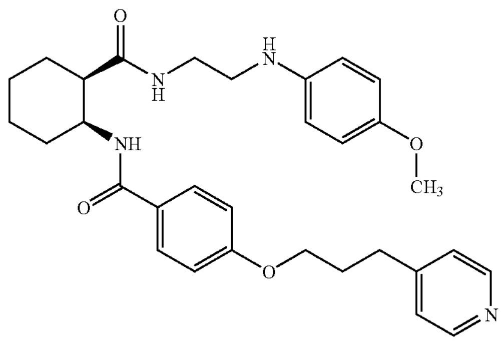 | T, R, A | N-{(1S,2R)-2-[2-(4-Methoxy-phenylamino)-ethylcarbamoyl]-cyclohexyl}-4-(3-pyridin-4-yl-propoxy)-benzamide |
| 23 | 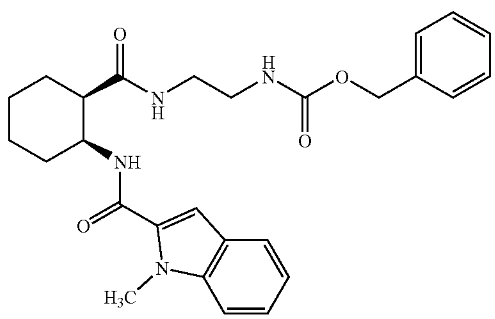 | A | [2-({(1R,2S)-2-[(1-Methyl-1H-indole-2-carbonyl)-amino]-cyclohexanecarbonyl}-amino)-ethyl]-carbamic acid benzyl ester |
| 24 | 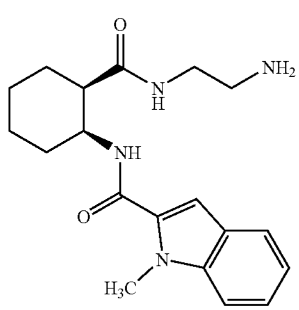 | A, D (+ Cbz removal) | 1-Methyl-1H-indole-2-carboxylic acid [(1S,2R)-2-(2-amino-ethylcarbamoyl)-cyclohexyl]-amide |

TABLE 1-continued

| # | Structure | Method | Name (Autonom) |
|---|---|---|---|
| 25 | 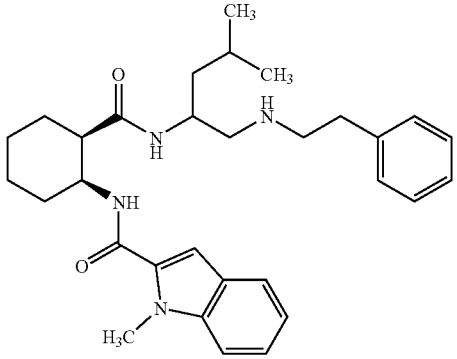 | A, F, G | 1-Methyl-1H-indole-2-carboxylic acid {(1S,2R)-2-[3-methyl-1-(phenethylamino-methyl)-butylcarbamoyl]-cyclohexyl}-amide |
| 26 | 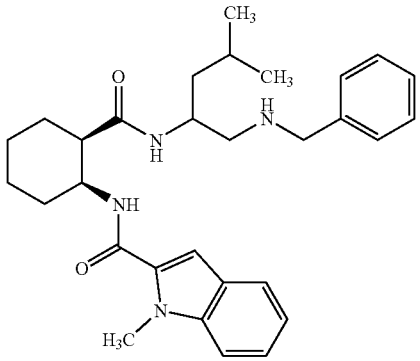 | A, F, G | 1-Methyl-1H-indole-2-carboxylic acid {(1S,2R)-2-[1-(benzylamino-methyl)-3-methyl-butylcarbamoyl]-cyclohexyl}-amide |
| 27 | 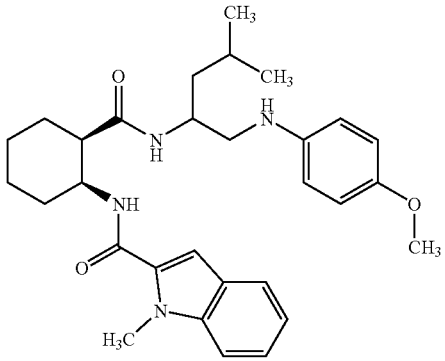 | A, F, G | 1-Methyl-1H-indole-2-carboxylic acid ((1S,2R)-2-{1-[(4-methoxy-phenylamino)-methyl]-3-methyl-butylcarbamoyl}-cyclohexyl)-amide |
| 28 | 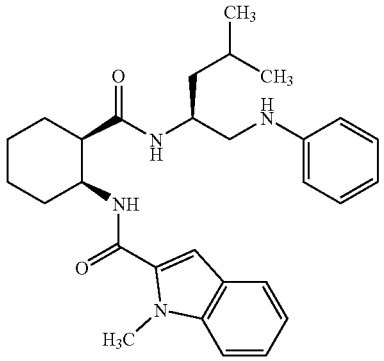 | A, F, G | 1-Methyl-1H-indole-2-carboxylic acid [(1S,2R)-2-((S)-3-methyl-1-phenylaminomethyl-butylcarbamoyl)-cyclohexyl]-amide |

TABLE 1-continued

| # | Structure | Method | Name (Autonom) |
|---|---|---|---|
| 29 | 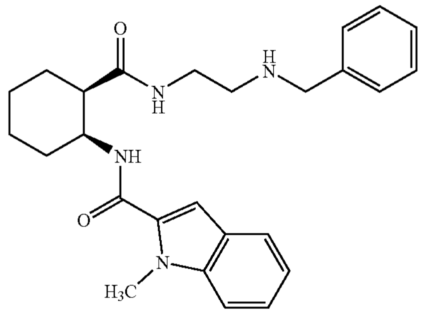 | A | 1-Methyl-1H-indole-2-carboxylic acid [(1S,2R)-2-(2-benzylamino-ethylcarbamoyl)-cyclohexyl]-amide |
| 30 | 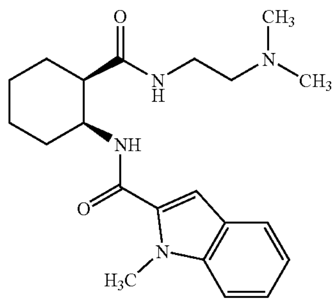 | A | 1-Methyl-1H-indole-2-carboxylic acid [(1S,2R)-2-(2-dimethylamino-ethylcarbamoyl)-cyclohexyl]-amide |
| 31 | 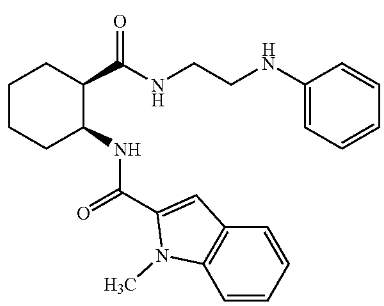 | A | 1-Methyl-1H-indole-2-carboxylic acid [(1S,2R)-2-(2-phenylamino-ethylcarbamoyl)-cyclohexyl]-amide |
| 32 | 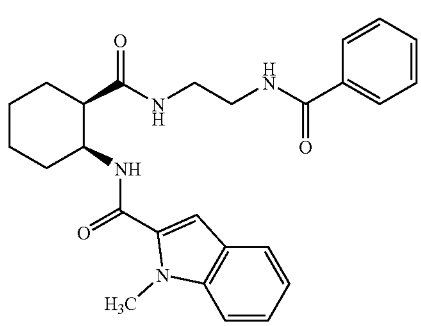 | A, D (+ Cbz removal), A | 1-Methyl-1H-indole-2-carboxylic acid [(1S,2R)-2-(2-benzoylamino-ethylcarbamoyl)-cyclohexyl]-amide |

TABLE 1-continued

| # | Structure | Method | Name (Autonom) |
|---|---|---|---|
| 33 | 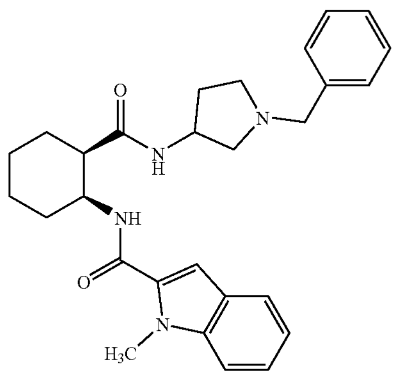 | A | 1-Methyl-1H-indole-2-carboxylic acid [(1S,2R)-2-(1-benzyl-pyrrolidin-3-ylcarbamoyl)-cyclohexyl]-amide |
| 34 | 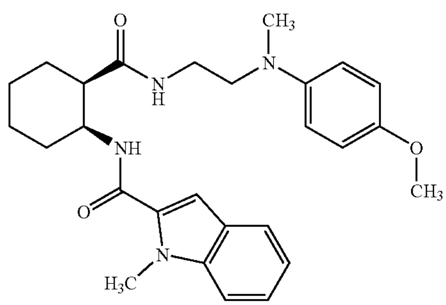 | A, K | 1-Methyl-1H-indole-2-carboxylic acid ((1S,2R)-2-{2-[(4-methoxy-phenyl)-methyl-amino]-ethylcarbamoyl}-cyclohexyl)-amide |
| 35 | 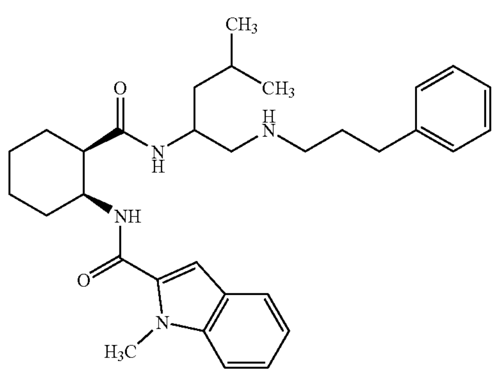 | A, F, G | 1-Methyl-1H-indole-2-carboxylic acid ((1S,2R)-2-{3-methyl-1-[(3-phenyl-propylamino)-methyl]-butylcarbamoyl}-cyclohexyl)-amide |
| 36 | 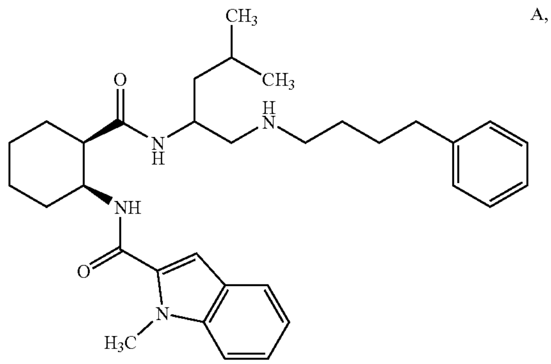 | A, F, G | 1-Methyl-1H-indole-2-carboxylic acid ((1S,2R)-2-{3-methyl-1-[(4-phenyl-butylamino)-methyl]-butylcarbamoyl}-cyclohexyl)-amide |

TABLE 1-continued

| # | Structure | Method | Name (Autonom) |
|---|---|---|---|
| 37 | 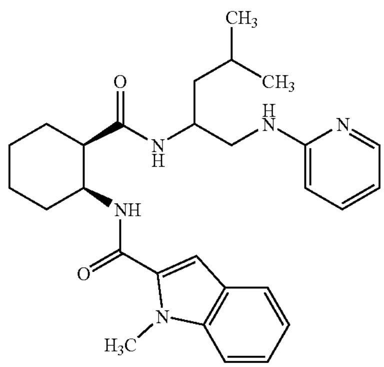 | A, F, G | 1-Methyl-1H-indole-2-carboxylic acid {(1S,2R)-2-[3-methyl-1-(pyridin-2-ylaminomethyl)-butylcarbamoyl]-cyclohexyl}-amide |
| 38 | 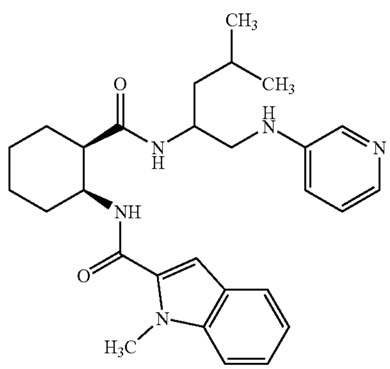 | A, F, G | 1-Methyl-1H-indole-2-carboxylic acid {(1S,2R)-2-[3-methyl-1-(pyridin-3-ylaminomethyl)-butylcarbamoyl]-cyclohexyl}-amide |
| 39 | 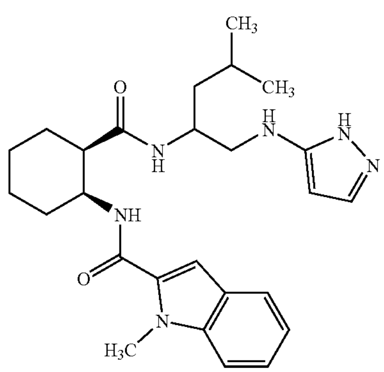 | A, F, G | 1-Methyl-1H-indole-2-carboxylic acid ((1S,2R)-2-{3-methyl-1-[(2H-pyrazol-3-ylamino)-methyl]-butylcarbamoyl}-cyclohexyl)-amide |
| 40 | 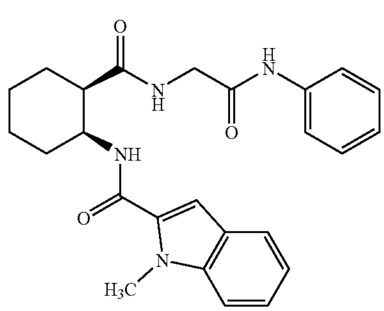 | A, R, A | 1-Methyl-1H-indole-2-carboxylic acid [(1S,2R)-2-(phenylcarbamoylmethyl-carbamoyl)-cyclohexyl]-amide |

TABLE 1-continued

| # | Structure | Method | Name (Autonom) |
|---|---|---|---|
| 41 | 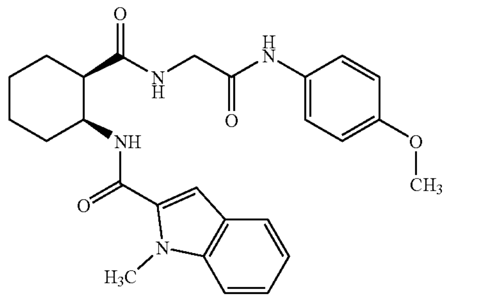 | A, R, A | 1-Methyl-1H-indole-2-carboxylic acid ((1S,2R)-2-{[(4-methoxy-phenylcarbamoyl)-methyl]-carbamoyl}-cyclohexyl)-amide |
| 42 | 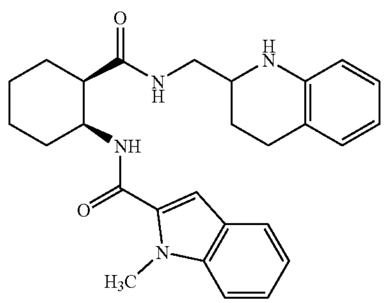 | A | 1-Methyl-1H-indole-2-carboxylic acid {(1S,2R)-2-[(1,2,3,4-tetrahydro-quinolin-2-ylmethyl)-carbamoyl]-cyclohexyl}-amide |
| 43 | 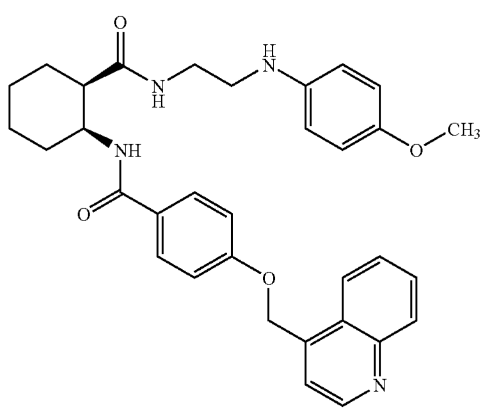 | Q, R, A | N-{(1S,2R)-2-[2-(4-Methoxy-phenylamino)-ethylcarbamoyl]-cyclohexyl}-4-(quinolin-4-ylmethoxy)-benzamide |
| 44 | 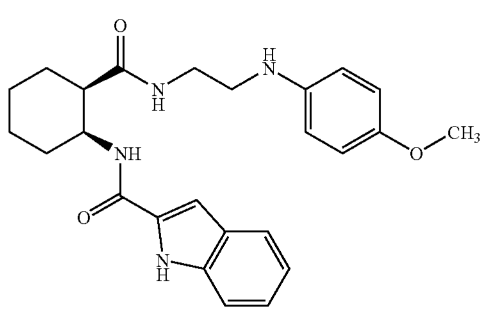 | I | 1H-Indole-2-carboxylic acid {(1S,2R)-2-[2-(4-methoxy-phenylamino)-ethylcarbamoyl]-cyclohexyl}-amide |

TABLE 1-continued

| # | Structure | Method | Name (Autonom) |
|---|---|---|---|
| 45 | 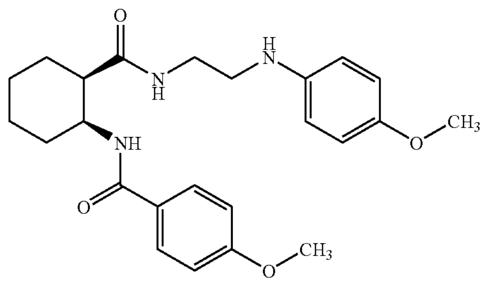 | I | 4-Methoxy-N-{(1S,2R)-2-[2-(4-methoxy-phenylamino)-ethylcarbamoyl]-cyclohexyl}-benzamide |
| 46 | 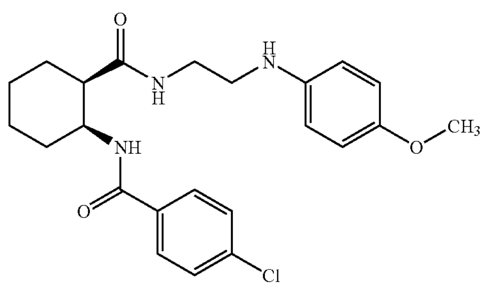 | I | 4-Chloro-N-{(1S,2R)-2-[2-(4-methoxy-phenylamino)-ethylcarbamoyl]-cyclohexyl}-benzamide |
| 47 | 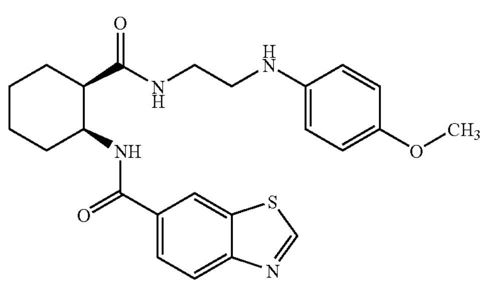 | I | Benzothiazole-6-carboxylic acid {(1S,2R)-2-[2-(4-methoxy-phenylamino)-ethylcarbamoyl-cyclohexyl}-amide |
| 48 | 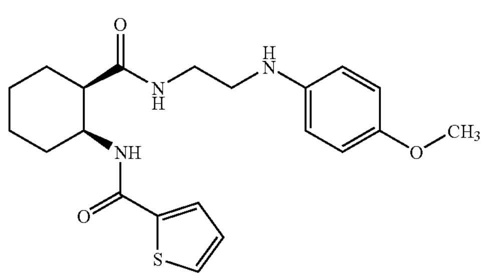 | I | Thiophene-2-carboxylic acid {(1S,2R)-2-[2-(4-methoxy-phenylamino)-ethylcarbamoyl-cyclohexyl}-amide |
| 49 | 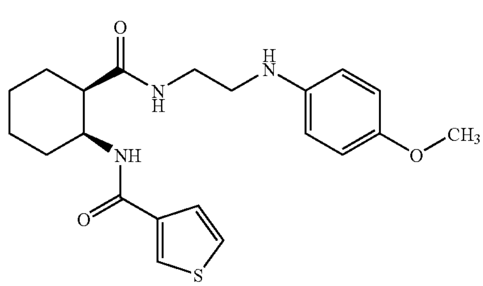 | I | Thiophene-3-carboxylic acid {(1S,2R)-2-[2-(4-methoxy-phenylamino)-ethylcarbamoyl-cyclohexyl}-amide |

TABLE 1-continued

| # | Structure | Method | Name (Autonom) |
|---|---|---|---|
| 50 | 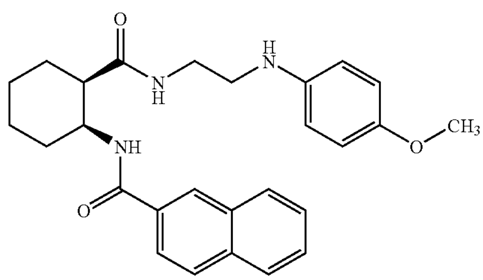 | I | Naphthalene-2-carboxylic acid {(1S,2R)-2-[2-(4-methoxy-phenylamino)-ethylcarbamoyl]-cyclohexyl}-amide |
| 51 | 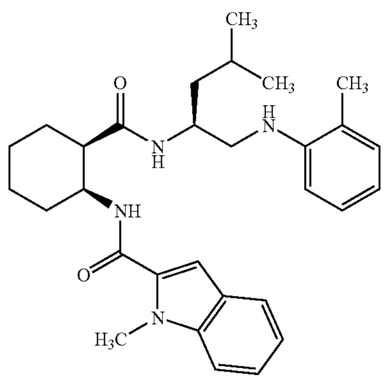 | A, F, G | 1-Methyl-1H-indole-2-carboxylic acid {(1S,2R)-2-[(S)-3-methyl-1-(o-tolylamino-methyl)-butylcarbamoyl]-cyclohexyl}-amide |
| 52 | 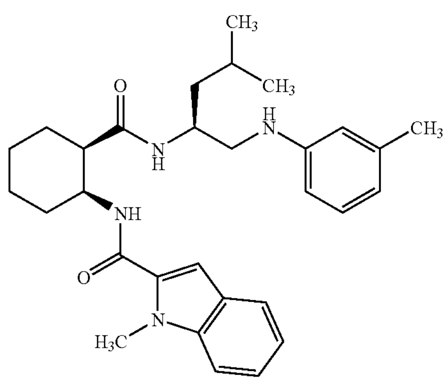 | A, F, G | 1-Methyl-1H-indole-2-carboxylic acid {(1S,2R)-2-[(S)-3-methyl-1-(m-tolylamino-methyl)-butylcarbamoyl]-cyclohexyl}-amide |
| 53 | 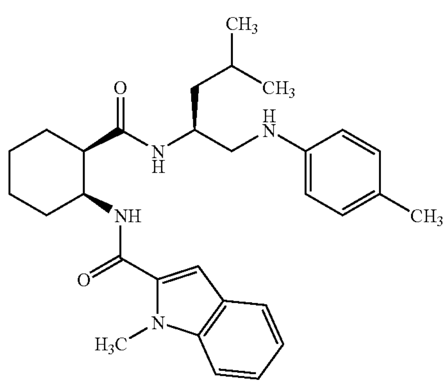 | A, F, G | 1-Methyl-1H-indole-2-carboxylic acid {(1S,2R)-2-[(S)-3-methyl-1-(p-tolylamino-methyl)-butylcarbamoyl]-cyclohexyl}-amide |

TABLE 1-continued

| # | Structure | Method | Name (Autonom) |
|---|---|---|---|
| 54 | 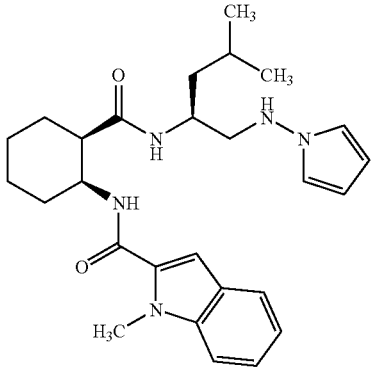 | A, F, G | 1-Methyl-1H-indole-2-carboxylic acid {(1S,2R)-2-[(S)-3-methyl-1-(pyrrol-1-ylaminomethyl)-butylcarbamoyl]-cyclohexyl}-amide |
| 55 | 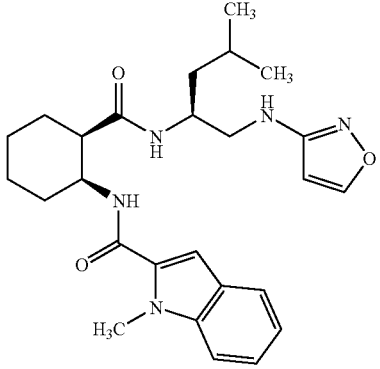 | A, F, G | 1-Methyl-1H-indole-2-carboxylic acid {(1S,2R)-2-[(S)-1-(isoxazol-3-ylaminomethyl)-3-methyl-butylcarbamoyl]-cyclohexyl}-amide |
| 56 | 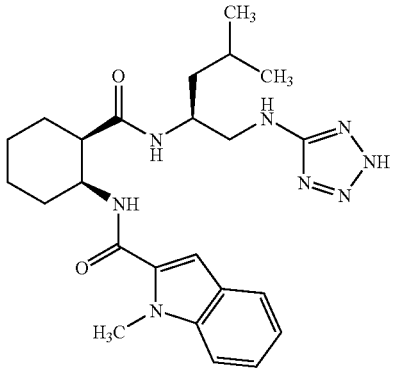 | A, F, G | 1-Methyl-1H-indole-2-carboxylic acid ((1S,2R)-2-{(S)-3-methyl-1-[(2H-tetrazol-5-ylamino)-methyl]-butylcarbamoyl}-cyclohexyl)-amide |
| 57 | 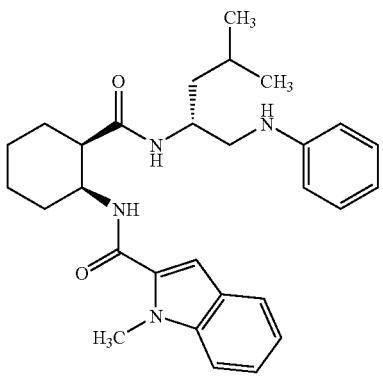 | A, F, G | 1-Methyl-1H-indole-2-carboxylic acid [(1S,2R)-2-((R)-3-methyl-1-phenylaminomethyl-butylcarbamoyl)-cyclohexyl]-amide |

TABLE 1-continued

| # | Structure | Method | Name (Autonom) |
|---|---|---|---|
| 58 | 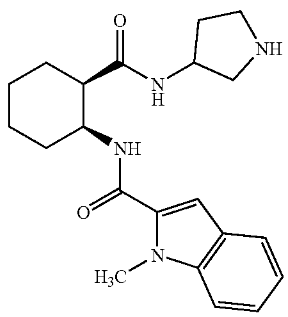 | A, C | 1-Methyl-1H-indole-2-carboxylic acid [(1S,2R)-2-(pyrrolidin-3-ylcarbamoyl)-cyclohexyl]-amide |
| 59 | 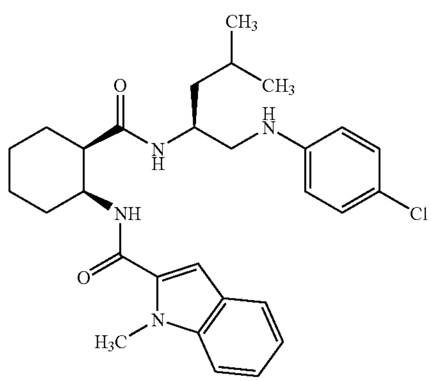 | A, F, G | 1-Methyl-1H-indole-2-carboxylic acid ((1S,2R)-2-{(S)-1-[(4-chloro-phenylamino)-methyl]-3-methyl-butylcarbamoyl}-cyclohexyl)-amide |
| 60 | 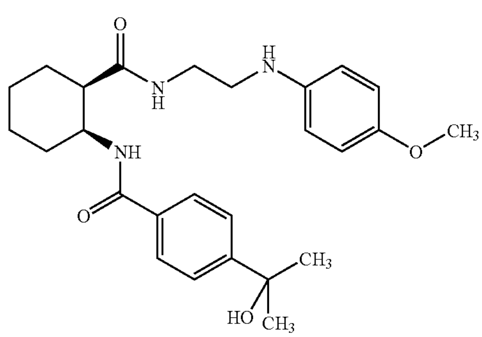 | S, I | 4-(1-Hydroxy-1-methyl-ethyl)-N-{(1S,2R)-2-[2-(4-methoxy-phenylamino)-ethylcarbamoyl]-cyclohexyl}-benzamide |
| 61 | 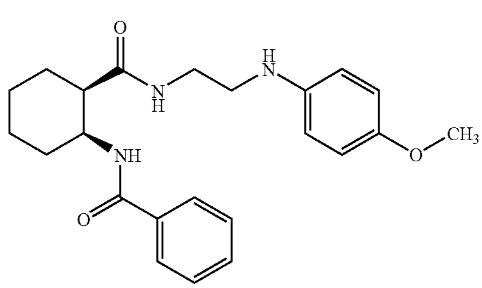 | I | N-{(1S,2R)-2-[2-(4-Methoxy-phenylamino)-ethylcarbamoyl]-cyclohexyl}-benzamide |

TABLE 1-continued

| # | Structure | Method | Name (Autonom) |
|---|---|---|---|
| 62 | 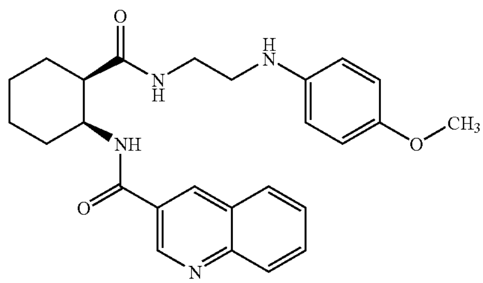 | I | Quinoline-3-carboxylic acid {(1S,2R)-2-[2-(4-methoxy-phenylamino)-ethylcarbamoyl]-cyclohexyl}-amide |
| 63 | 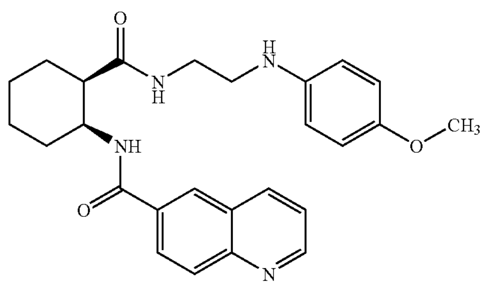 | I | Quinoline-6-carboxylic acid {(1S,2R)-2-[2-(4-methoxy-phenylamino)-ethylcarbamoyl]-cyclohexyl}-amide |
| 64 | 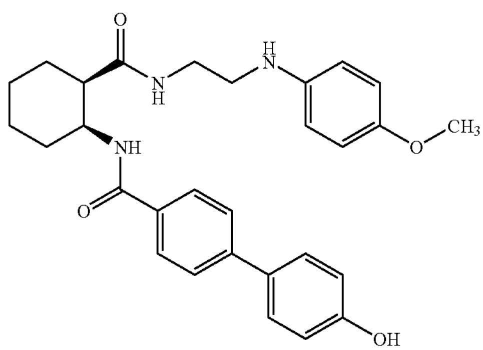 | I | 4'-Hydroxy-biphenyl-4-carboxylic acid {(1S,2R)-2-[2-(4-methoxy-phenylamino)-ethylcarbamoyl]-cyclohexyl}-amide |
| 65 | 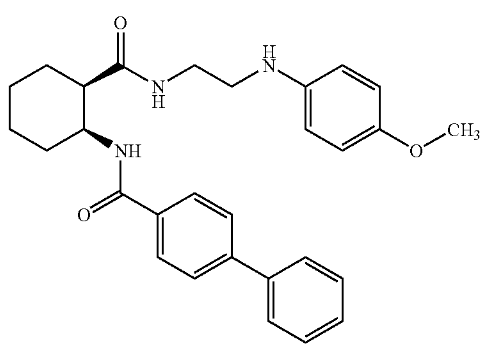 | I | Biphenyl-4-carboxylic acid {(1S,2R)-2-[2-(4-methoxy-phenylamino)-ethylcarbamoyl]-cyclohexyl}-amide |
| 66 | 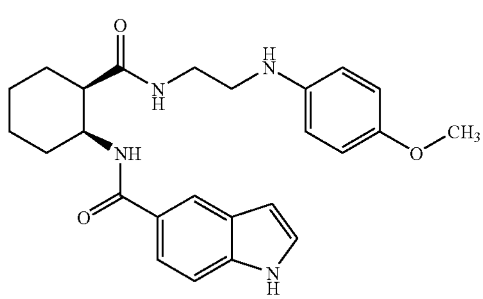 | I | 1H-Indole-5-carboxylic acid {(1S,2R)-2-[2-(4-methoxy-phenylamino)-ethylcarbamoyl]-cyclohexyl}-amide |

TABLE 1-continued

| # | Structure | Method | Name (Autonom) |
|---|---|---|---|
| 67 | 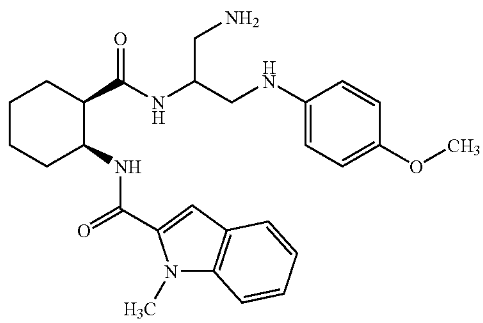 | M, N, O, P, A, D | 1-Methyl-1H-indole-2-carboxylic acid ((1S,2R)-2-{2-amino-1-[(4-methoxy-phenylamino)-methyl]-ethylcarbamoyl}-cyclohexyl)-amide |
| 68 | 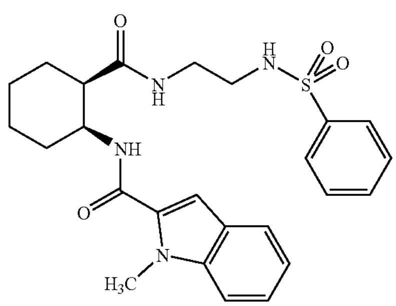 | A, D (+ Cbz removal) | 1-Methyl-1H-indole-2-carboxylic acid [(1S,2R)-2-(2-benzenesulfonylamino-ethylcarbamoyl)-cyclohexyl]-amide |
| 69 | 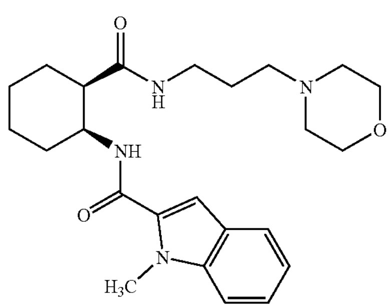 | A | 1-Methyl-1H-indole-2-carboxylic acid [(1S,2R)-2-(3-morpholin-4-yl-propylcarbamoyl)-cyclohexyl]-amide |
| 70 | 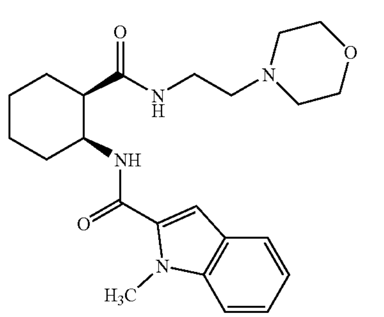 | A | 1-Methyl-1H-indole-2-carboxylic acid [(1S,2R)-2-(2-morpholin-4-yl-ethylcarbamoyl)-cyclohexyl]-amide |

TABLE 1-continued

| # | Structure | Method | Name (Autonom) |
|---|---|---|---|
| 71 | 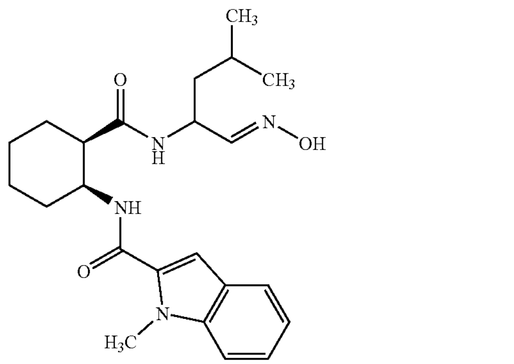 | A, F, H | 1-Methyl-1H-indole-2-carboxylic acid {(1S,2R)-2-[1-(hydroxyimino-methyl)-3-methyl-butylcarbamoyl]-cyclohexyl}-amide |
| 72 | 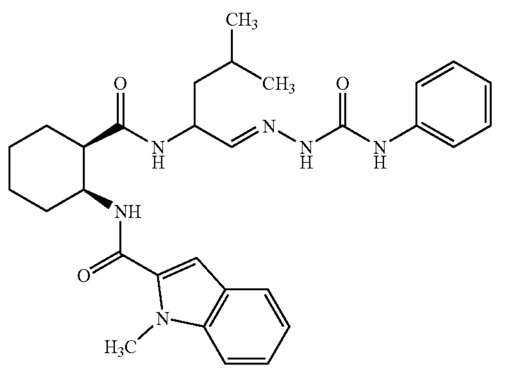 | A, F, H | 1-Methyl-1H-indole-2-carboxylic acid ((1S,2R)-2-{1-[(anilinocarbonyl)hydrazono-methyl]-3-methyl-butylcarbamoyl}-cyclohexyl)-amide |
| 73 | 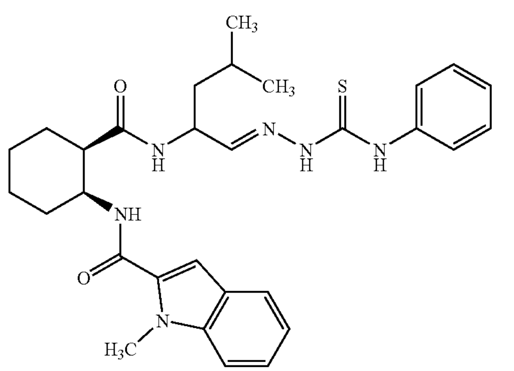 | A, F, H | 1-Methyl-1H-indole-2-carboxylic acid [(1S,2R)-2-(1-{[(benzylamino)carbonothioyl]hydrazono-methyl}-3-methyl-butylcarbamoyl)-cyclohexyl]-amide |
| 74 | 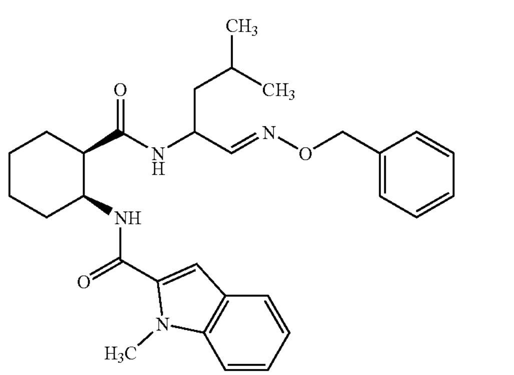 | A, F, H | 1-Methyl-1H-indole-2-carboxylic acid {(1S,2R)-2-[1-(benzyloxyimino-methyl)-3-methyl-butylcarbamoyl]-cyclohexyl}-amide |

TABLE 1-continued

| # | Structure | Method | Name (Autonom) |
|---|---|---|---|
| 75 | 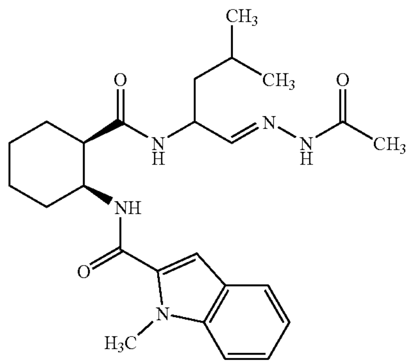 | A, F, H | 1-Methyl-1H-indole-2-carboxylic acid {(1S,2R)-2-[1-(acetyl-hydrazonomethyl)-3-methyl-butylcarbamoyl]-cyclohexyl}-amide |
| 76 | 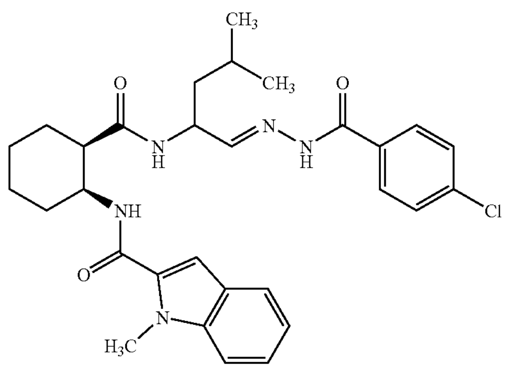 | A, F, H | 1-Methyl-1H-indole-2-carboxylic acid ((1S,2R)-2-{1-[4-chloro-benzoyl)-hydrazonomethyl]-3-methyl-butylcarbamoyl}-cyclohexyl)-amide |
| 77 | 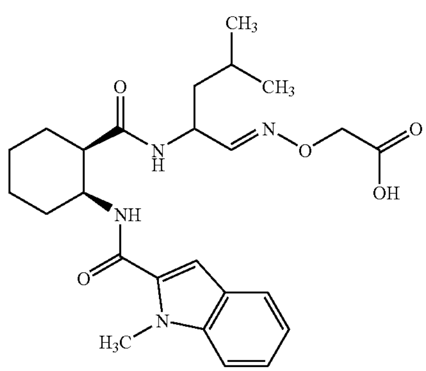 | A, F, H | [4-Methyl-2-({(1R,2S)-2-[(1-methyl-1H-indole-2-carbonyl)-amino]-cyclohexanecarbonyl}-amino)-pent-(E)-ylideneaminooxy]-acetic acid |
| 78 | 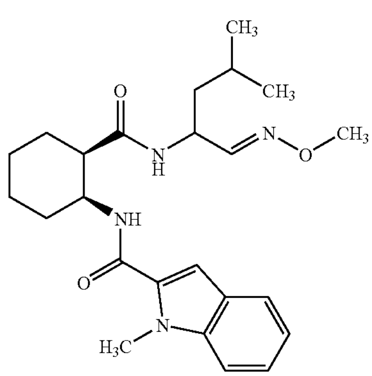 | A, F, H | 1-Methyl-1H-indole-2-carboxylic acid {(1S,2R)-2-[1-(methoxyimino-methyl)-3-methyl-butylcarbamoyl]-cyclohexyl}-amide |

TABLE 1-continued

| # | Structure | Method | Name (Autonom) |
|---|---|---|---|
| 79 | 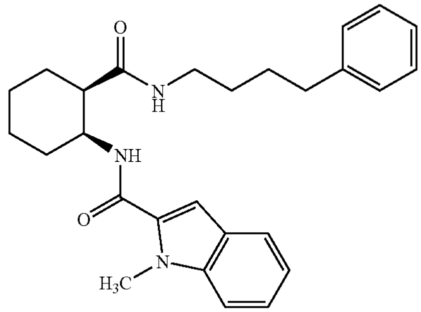 | A | 1-Methyl-1H-indole-2-carboxylic acid [(1S,2R)-2-(4-phenyl-butylcarbamoyl)-cyclohexyl]-amide |
| 80 | 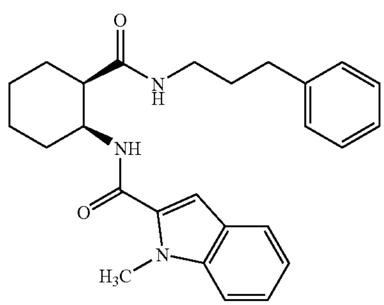 | A | 1-Methyl-1H-indole-2-carboxylic acid [(1S,2R)-2-(3-phenyl-propylcarbamoyl)-cyclohexyl]-amide |
| 81 | 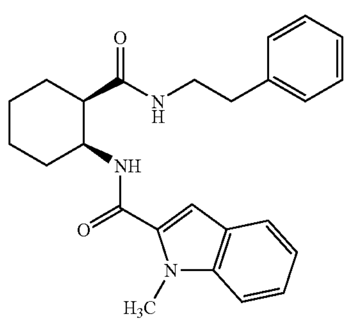 | A | 1-Methyl-1H-indole-2-carboxylic acid ((1S,2R)-2-phenethylcarbamoyl-cyclohexyl)-amide |
| 82 | 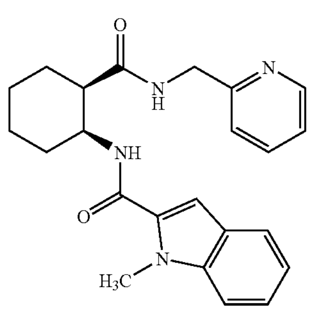 | A | 1-Methyl-1H-indole-2-carboxylic acid {(1S,2R)-2-[(pyridin-2-ylmethyl)-carbamoyl]-cyclohexyl}-amide |
| 83 | 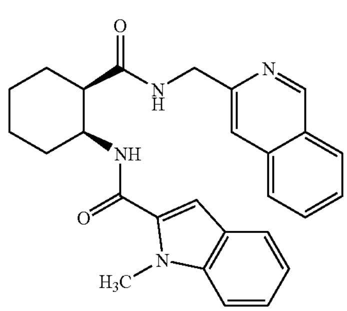 | A | 1-Methyl-1H-indole-2-carboxylic acid {(1S,2R)-2-[(isoquinolin-3-ylmethyl)-carbamoyl]-cyclohexyl}-amide |

TABLE 1-continued

| # | Structure | Method | Name (Autonom) |
|---|---|---|---|
| 84 | 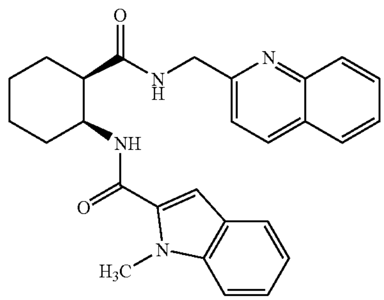 | A | 1-Methyl-1H-indole-2-carboxylic acid {(1S,2R)-2-[(quinolin-2-ylmethyl)-carbamoyl]-cyclohexyl}-amide |
| 85 | 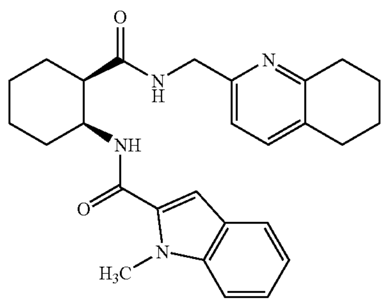 | A | 1-Methyl-1H-indole-2-carboxylic acid {(1S,2R)-2-[(5,6,7,8-tetrahydro-quinolin-2-ylmethyl)-carbamoyl]-cyclohexyl}-amide |
| 86 | 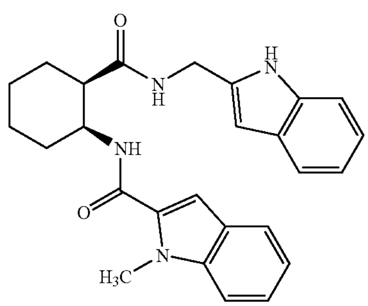 | A | 1-Methyl-1H-indole-2-carboxylic acid {(1S,2R)-2-[(1H-indol-2-ylmethyl)-carbamoyl]-cyclohexyl}-amide |
| 87 | 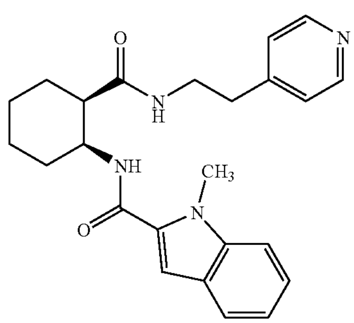 | A | 1-Methyl-1H-indole-2-carboxylic acid [(1S,2R)-2-(2-pyridin-4-yl-ethylcarbamoyl)-cyclohexyl]-amide |
| 88 | 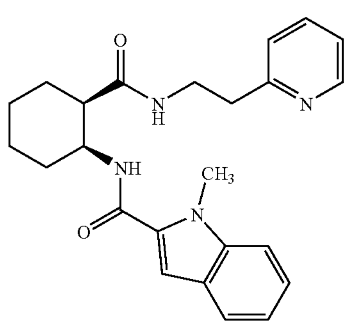 | A | 1-Methyl-1H-indole-2-carboxylic acid [(1S,2R)-2-(2-pyridin-2-yl-ethylcarbamoyl)-cyclohexyl]-amide |

TABLE 1-continued

| # | Structure | Method | Name (Autonom) |
|---|---|---|---|
| 89 | 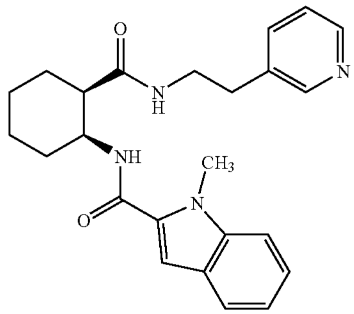 | A | 1-Methyl-1H-indole-2-carboxylic acid [(1S,2R)-2-(2-pyridin-3-yl-ethylcarbamoyl)-cyclohexyl]-amide |
| 90 | 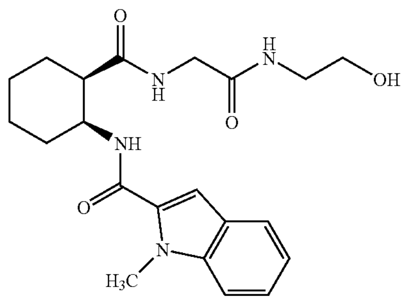 | A, R, A | 1-Methyl-1H-indole-2-carboxylic acid ((1S,2R)-2-{[(2-hydroxy-ethylcarbamoyl)-methyl]-carbamoyl}-cyclohexyl)-amide |
| 91 | 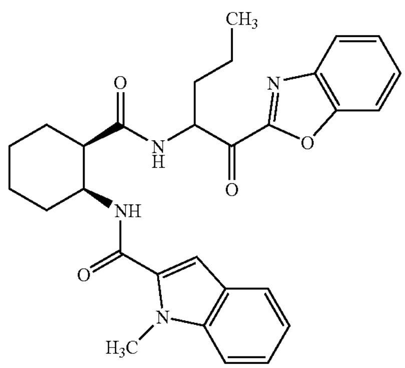 | A, E | 1-Methyl-1H-indole-2-carboxylic acid {(1S,2R)-2-[(S)-1-(benzooxazole-2-carbonyl)-butylcarbamoyl]-cyclohexyl}-amide |

Utility

The present invention also relates to a method for the prophylactic and/or therapeutic treatment of diseases which are associated with cystein proteases such as osteoporosis, osteoarthritis, rheumatoid arthritis, tumor metastasis, glomerulonephritis, atherosclerosis, myocardial infarction, angina pectoris, instable angina pectoris, stroke, plaque rupture, transient ischemic attacks, amaurosis fugax, peripheral arterial occlusive disease, restenosis after angioplasty and stent placement, abdominal aortic aneurysm formation, inflammation, autoimmune disease, malaria, ocular fundus tissue cytopathy and respiratory disease, which method comprises administering a compound of Formula I to a human being or an animal.

The invention also provides for the use of the aforementioned compounds for the preparation of medicaments for the treatment or prophylaxis of diseases which are associated with cystein proteases, such as osteoporosis, osteoarthritis, rheumatoid arthritis, tumor metastasis, glomerulonephritis, atherosclerosis, myocardial infarction, angina pectoris, instable angina pectoris, stroke, plaque rupture, transient ischemic attacks, amaurosis fugax, peripheral arterial occlusive disease, restenosis after angioplasty and stent placement, abdominal aortic aneurysm formation, inflammation, autoimmune disease, malaria, ocular fundus tissue cytopathy and respiratory disease. In one embodiment the invention relates to the use of compounds as defined above for the preparation of medicaments for the treatment or prophylaxis of osteoporosis, instable angina pectoris or plaque rupture. Such medicaments comprise a compound as defined above.

Another embodiment of the invention relates to a method for the prophylactic and/or therapeutic treatment of disorders in which cathepsin K plays a significant pathological role, such as osteoporosis, osteoarthritis, rheumatoid arthritis, tumor metastasis, glomerulonephritis, atherosclerosis, myocardial infarction, angina pectoris, instable angina pectoris, stroke, plaque rupture, transient ischemic attacks, amaurosis fugax, peripheral arterial occlusive disease, restenosis after angioplasty and stent placement, abdominal aortic aneurysm formation, inflammation, autoimmune disease, malaria, ocular fundus tissue cytopathy and respiratory disease, which method comprises administering a compound as defined above to a human being or an animal. A preferred embodiment of the invention relates to a method for the prophylactic and/or therapeutic treatment of osteoporosis, instable angina pectoris or plaque rupture, which method comprises administering a compound as defined above to a human being or an animal.

The invention also provides combination therapies and methods comprising administering a compound of Formula I, in combination with one or more additional compounds of Formula I, or in combination with one or more additional active ingredients, to a patient or subject in need thereof. In one embodiment the combination therapy method of the invention comprises administering a compound of Formula I, in combination with a therapeutic amount of a bisphosphonic acid, bisphosphonic ester, or pharmaceutically acceptable salt thereof, to a subject or patient. Exemplary bisphosphonic acids and esters usable in combination therapies with compounds of Formula I include, by way of example:

b 4-amino-1-hydroxybutylidene-1,1-bisphosphonic acid (alendronic acid) and 4-amino-1-hydroxybutylidene-1,1-bisphosphonate monosodium trihydrate (alendronate monosodium trihydrate), described in U.S. Pat. Nos. 4,922,007; 5,019,651; 5,510,517; and 5,648,491; cycloheptylaminomethylene-1,1-bisphosphonic acid (cimadronic acid), described in U.S. Pat. No. 4,970,335; 1,1-dichloromethyene-1,1-diphosphonic acid (clondronic acid) and the sodium salt thereof, described in Belgian Patent No. 672,205 and in J. Org. Chem 1967, 32, 4111; 1-hydroxy-3-pyrrolidin-1-ylpropylidene-1,1-bisphosphonic acid (EB-1053); 1-hydroxyethylidene-1,1-diphosphonic acid (etidronic acid); 1-hydroxy-3-(N-methyl-N-pentylamino)propylidene-1,1-bisphosphonic acid (ibandronic acid), described in U.S. Pat. No. 4,927,814; 6-amino-1-hydroxypropylidene-1,1-bisphosphonic acid (neridronic acid) 3-(dimethylamino)-1-hydroxypropylidene-1,1-bisphosphonic acid (olpadronic acid); 3-amino-1-hydroxypropylidene-1,1-bisphosphonic acid (pamidronic acid); 2-pyrid-2-ylethylidene-1,1-bisphosphonic acid (pyridonic acid), described in U.S. Pat. No. 4,761,406; 1-hydroxy-2-pyrid-3-ylethylidene-1,1-bisphosphonic acid (risedronic acid); 4-chlorophenylsulfanylmethylenebisphosphonic acid (tiludronic acid); and 1-hydroxy-2-(1H-imidazol-1-yl)ethylidene-1,1-bisphosphonic acid (zoledronic acid).

In certain embodiments, the combination therapy may comprise administering to a patient or subject in need thereof an effective amount of a compound of Formula I in combination with alendronic acid, cimadronic acid, clodronic acid, tiludronic acid, etidronic acid, ibandronic acid, risedronic acid, pyridronic acid, pamidronic acid, zolendronic acid, or a pharmaceutically acceptable salt or solvate thereof, and mixtures thereof.

Synthesis

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis;* Wiley & Sons: New York, 1991, Volumes 1-20; *Rodd's Chemistry of Carbon Compounds,* Elsevier Science Publishers, 1989, Volumes 1-5 and Supplementals; and *Organic Reactions,* Wiley & Sons: New York, 1991, Volumes 1-40. The following synthetic reaction schemes are merely illustrative of some methods by which the compounds of the present invention may be synthesized, and various modifications to these synthetic reaction schemes may be made and will be suggested to one skilled in the art having referred to the disclosure contained in this Application.

The starting materials and the intermediates of the synthetic reaction schemes may be isolated and purified if desired using conventional techniques, including but not limited to filtration, distillation, crystallization, chromatography, and the like. Such materials may be characterized using conventional means, including physical constants and spectral data.

Unless specified to the contrary, the reactions describes herein preferably take place at atmospheric pressure over a temperature range from about −78° C. to about 150° C., more preferably from about 0° C. to about 125° C., and most preferably and conveniently at about room (or ambient) temperature, e.g., about 20° C.

Many of the intermediates and/or starting materials can be obtained commercially or from the processes disclosed in the commonly assigned U.S. patent Application Ser. No. 10/453,112 (Publication No. US 2004/0077646 A1), which is incorporated herein by reference in its entirety.

Some of the compounds of Formula I were prepared using the synthetic strategy shown in Scheme I. The starting compound was prepared as described in the above disclosed U.S. patent application Ser. No. 10/453,112.

Scheme I

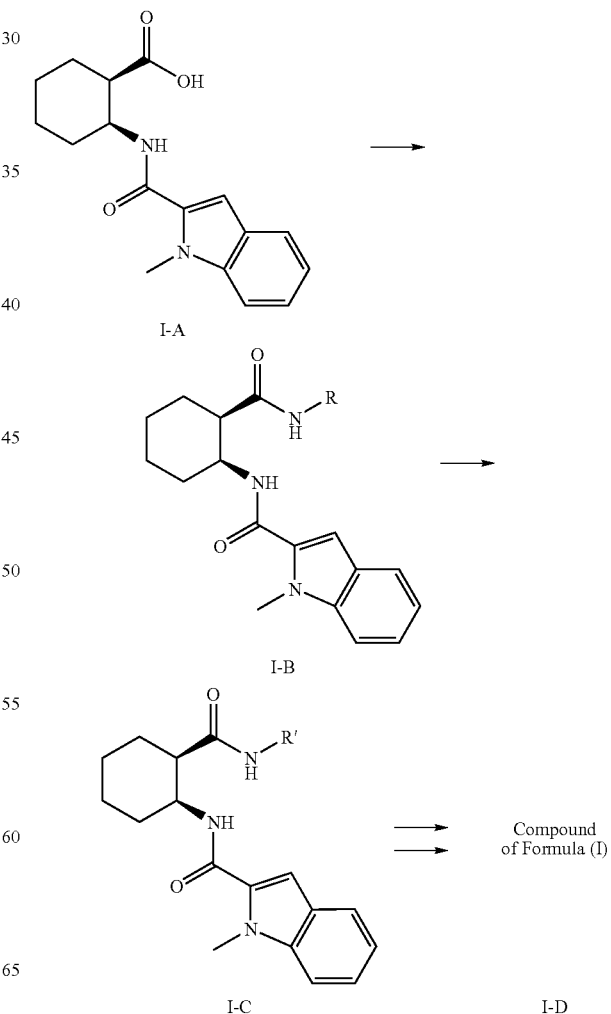

Briefly, the carboxylic acid I-A is converted to the amide compound I-B. Such conversion of a carboxylic acid to an amide is well known to one skilled in the art. Typically this is achieved by converting the carboxylic acid moiety to a suitable leaving group including, but not limited to, an anhydride, ester, acyl halide, and other leaving groups, such as by reacting with a carbodiimide (e.g., a mixture of DCC or EDCI and HOBT). Typical reaction conditions for this transformation are disclosed in Method A of Example 1. The activated carboxylic acid moiety is then reacted with an amine compound such as R—NH$_2$ to produce an amide I-B. Depending on the functional group(s) present on the amide I-B, one can further derivatize the amide I-B to an amide I-C. For example, if the amide I-B contains a protected amino group on the R group, it can be deprotected and further modified to another amide group or a mono- or di-alkylated amino group. If necessary, it can be further modified to produce other compounds of Formula I, such as a heterocyclyl, heteroaryl, or aryl moiety containing R group.

Another exemplary synthetic scheme for preparing compounds of Formula I is shown in Scheme II. Similar to Scheme I, the starting compound of Scheme II can be prepared using the processes described in the above disclosed U.S. patent application Ser. No. 10/453,112.

Scheme II

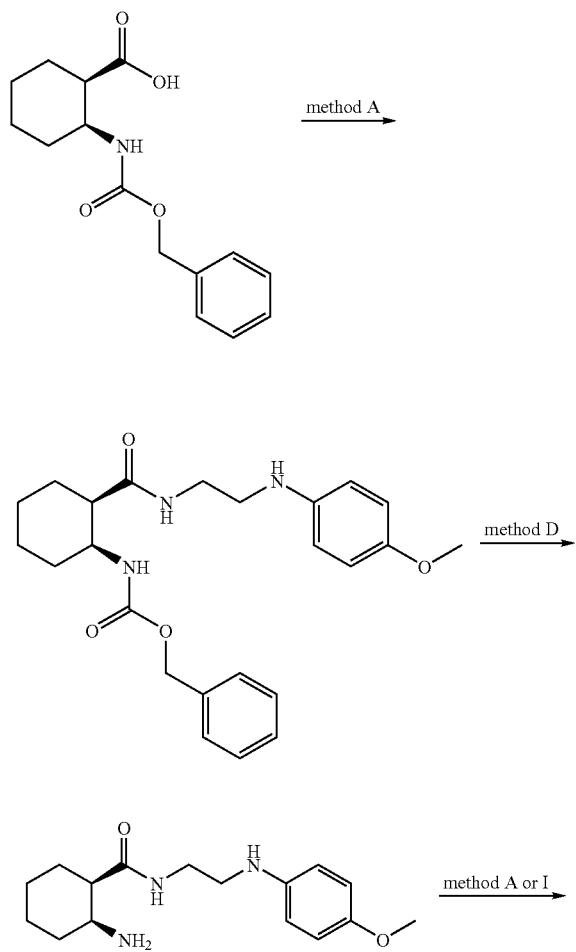

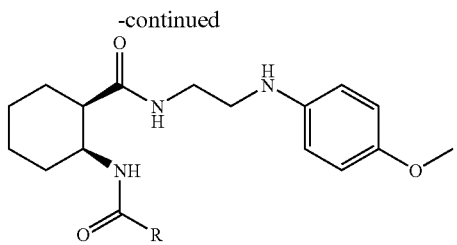

The references to the methods in Scheme II refer to those disclosed in the Examples section of this disclosure. Generally, the synthetic strategy exemplified in Scheme II utilizes coupling of an amino group of the cycloalkyl ring with the activated carboxylic acid moiety that is represented by a moiety of the formula —C(=O)—(R$^1$)$_n$—Ar$^1$ in Formula I. As described in reference to Scheme I above, typical coupling reaction conditions of an amino group to a carboxylic acid moiety is well known to one skilled in the art.

Administration and Pharmaceutical Composition

The invention includes pharmaceutical compositions comprising a compound as defined above and a pharmaceutically acceptable carrier and/or adjuvant or diluent. The compositions are for use in context with diseases associated with cysteine proteases such as osteorporsis, osteoarthritis, rheumatoid arthritis, tumor metastasis, glomerulonephritis, atherosclerosis, myocardial infarction, angina pectoris, instable angina pectoris, stroke, plaque rupture, transient ischemic attacks, amaurosis fugax, peripheral arterial occlusive disease, restenosis after angioplasty and stent placement, abdominal aortic aneurysm formation, inflammation, autoimmune disease, malaria, ocular fundus tissue cytopathy and respiratory disease. In one embodiment the invention relates to pharmaceutical compositions comprising a compound as defined above and a pharmaceutically acceptable carrier and/or adjuvant for use in context with osteoporosis, instable angina pectoris or plaque rupture.

In general, the compounds of the invention will be administered in a therapeutically effective amount by any of the accepted modes of administration for agents that serve similar utilities. Suitable dosage ranges are typically 1-500 mg daily, preferably 1-100 mg daily, and most preferably 1-30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

In general, compounds of the present invention will be administered as pharmaceutical formulations including those suitable for oral (including buccal and sublingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

A compound or compounds of the present invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the present invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in Remington: *The Science and Practice of Pharmacy*, 1995, edited by E. W. Martin, Mack Publishing Company, 9th edition, Easton, Pa. Representative pharmaceutical formulations containing a compound of the present invention are described in the following examples.

EXAMPLES

The following examples and preparations are provided to enable those skilled in the art to more clearly understand and to practice the present invention. They should not be considered as limiting the scope of the invention, but merely as being illustrative and representative thereof. The starting materials used in the examples and preparations are either commercially available or can be obtained by methods known in the art (e.g., from: DE 26 24 290; WO 98/0354; *Chem. Pharm. Bull.*, 38(2), 350-354 (1990), "Chiral Synthon Obtained with Pig Liver Esterase: Introduction of Chiral Centers into Cyclohexene Skeleton"; *J. Chem. Soc. Perkin Trans.*, 1, 1411-1415 (1994), "Asymmetric Synthesis of (–)-(1R,2S)-Cispentacin and Related cis- and trans-2-Amino Cyclopentane- and Cyclohexane-1-carboxylic Acids") or can be obtained by methods analogous to the methods described before. Table 2 provides a list of acronyms for reagents and solvents used in the following examples.

TABLE 2

| Representative acronyms of reagents. | |
|---|---|
| Burgess Reagent | (Methoxycarbonylsulfamoyl)triethylammonium hydroxide, inner salt |
| DCM or CH$_2$Cl$_2$ | Dichloromethane |
| DIC | 2-Dimethylaminoisopropyl chloride, hydrochloride |
| DIPEA | N,N-Diisopropylethylamine |
| DMAP | 4-Dimethylaminopyridine |
| DMF | N,N-Dimethylformamide |

TABLE 2-continued

| Representative acronyms of reagents. | |
|---|---|
| EDCl | 1-(3-Dimethylaminopropyl)-3-ethylcarbodiimide hydrochloride |
| HOBT | 1-Hydroxybenzotriazole hydrate |
| MEOH | Methanol |
| NMM | N-Methylmorpholine |
| NMP | 1-Methyl-2-pyrrolidinone |
| TBS | tert-Butyldimethylsilyl (a protecting group) |
| TFA | Trifluoroacetic acid |
| THF | Tetrahydrofuran |

Example 1

This example illustrates a various methods for preparing compounds of Formula I. Typically, one or more methods described in this example will be used for the synthesis of compounds of Formula I. Methods that are used will necessarily depend on a variety of factors including the substituents present in compounds of Formula I. Methods disclosed herein are merely illustrative of a particular transformation and are not intended to be limiting.

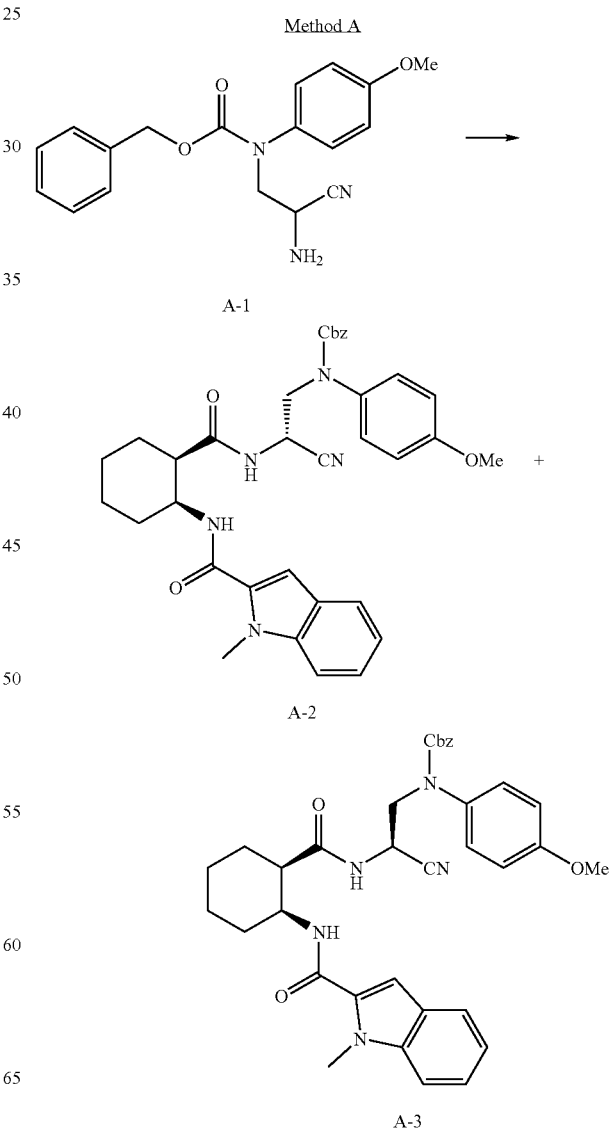

To a flask was added amino-nitrile A-1 (1.10 g, 3.66 mol), the acid (1.20 g, 4.01 mmol), EDCI hydrochloride (0.80 g, 4.17 mmol), HOBT (0.54 g, 4.00 mmol), NMM (1.5 mL, 13.6 mmol) and 18 mL of DMF. The reaction mixture was stirred at ambient temperature for 5 hrs. The reaction mixture was partitioned between 150 mL of water and 150 mL of ethyl acetate. The organic layer was washed with 150 mL of 1 N aq. HCl solution, 150 mL of water, dried over sodium sulfate, filtered, concentrated and purified by column chromatography (40-50:60-50, ethyl acetate:hexanes) to give 902 mg of the (R)-epimer and 908 mg of the (S)-epimer as white foams. Yield: 81%, MS: 630 (M+Na$^+$), mp=78.0-88.7° C. (S-epimer), mp=79.6-83.8° C. (R-epimer).

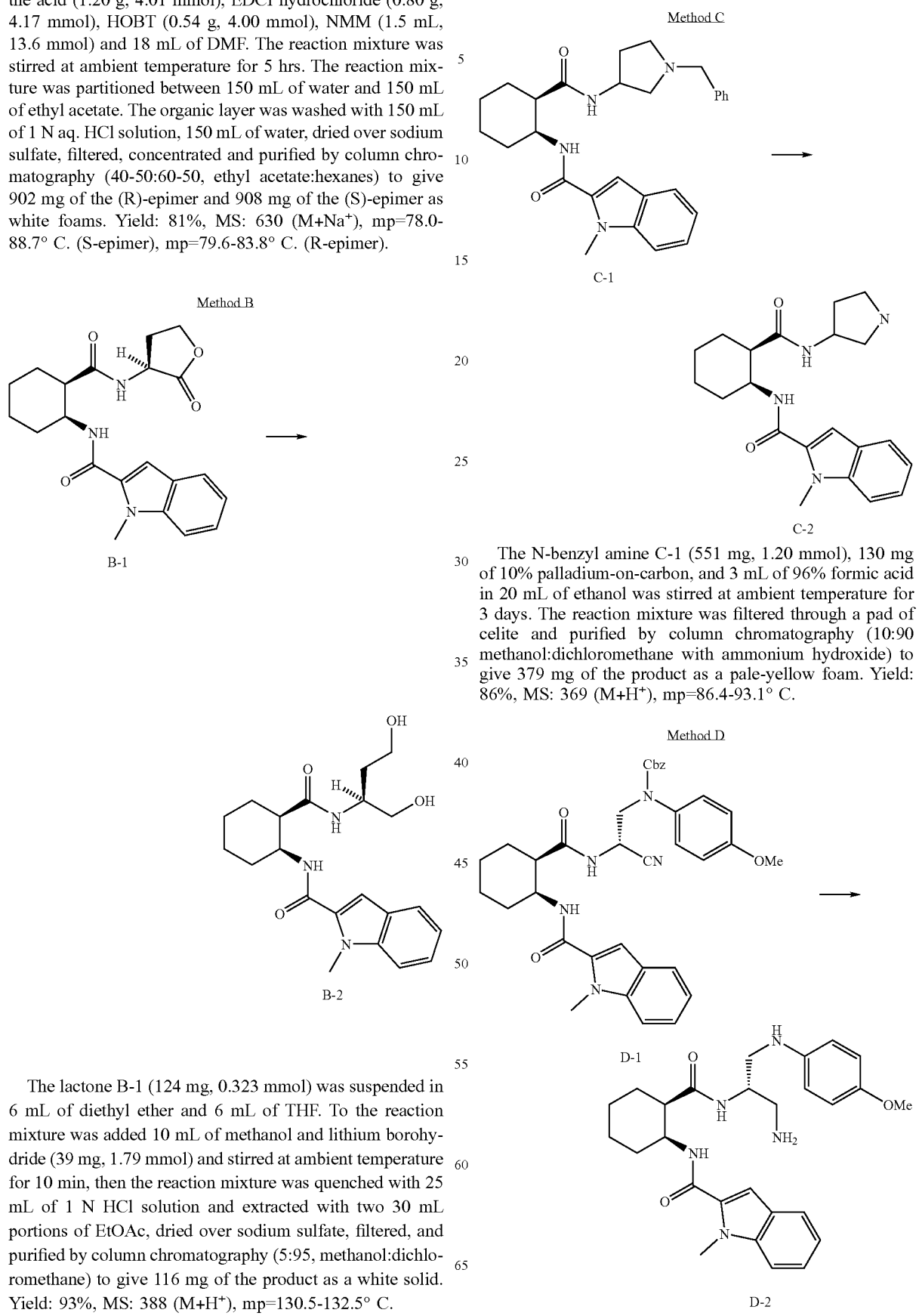

The lactone B-1 (124 mg, 0.323 mmol) was suspended in 6 mL of diethyl ether and 6 mL of THF. To the reaction mixture was added 10 mL of methanol and lithium borohydride (39 mg, 1.79 mmol) and stirred at ambient temperature for 10 min, then the reaction mixture was quenched with 25 mL of 1 N HCl solution and extracted with two 30 mL portions of EtOAc, dried over sodium sulfate, filtered, and purified by column chromatography (5:95, methanol:dichloromethane) to give 116 mg of the product as a white solid. Yield: 93%, MS: 388 (M+H$^+$), mp=130.5-132.5° C.

The N-benzyl amine C-1 (551 mg, 1.20 mmol), 130 mg of 10% palladium-on-carbon, and 3 mL of 96% formic acid in 20 mL of ethanol was stirred at ambient temperature for 3 days. The reaction mixture was filtered through a pad of celite and purified by column chromatography (10:90 methanol:dichloromethane with ammonium hydroxide) to give 379 mg of the product as a pale-yellow foam. Yield: 86%, MS: 369 (M+H$^+$), mp=86.4-93.1° C.

The nitrile D-1 (866 mg, 1.43 mmol) and 10% palladium-on-carbon (320 mg) in 25 mL of ethyl alcohol was stirred at ambient temperature under a H$_2$-atmosphere overnight. The reaction mixture was filtered through a pad of celite and purified by column chromatography (10:90, methanol:dichloromethane) to give 60 mg of a pale yellow film. Yield: 9%, MS: 478 (M+H$^+$).

Method E

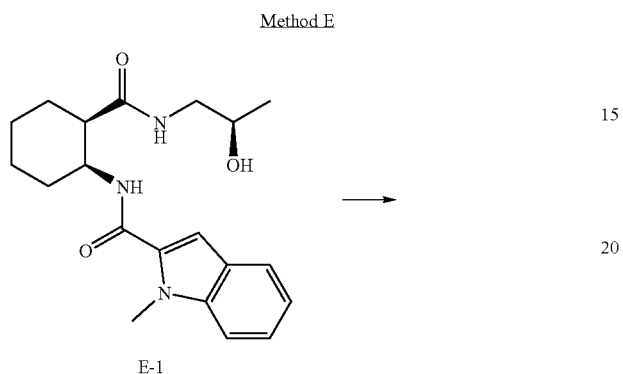

E-1

E-2

To 112 mg (0.31 mmol) of E-1 dissolved in 5 mL of dichloromethane was added 133 mg (0.31 mmol) Dess-Martin Periodinane. The mixture was stirred at room temperature for 1 h, partitioned between dichloromethane and water, dried over magnesium sulfate and concentrated. Column chromatography, eluting with 15% acetone/dichloromethane, provided 78 mg (90%) of compound E-2, pure by $^1$H NMR.

Method F

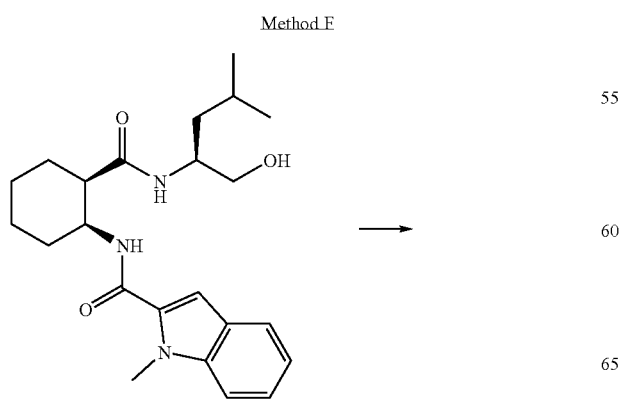

-continued

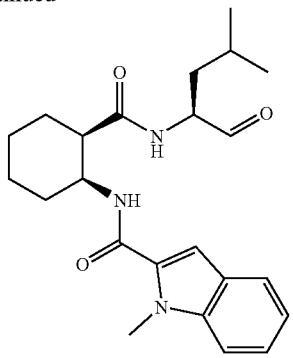

1-Methyl-1H-indole-2-carboxylic acid [(1S,2R)-2-((S)-1-hydroxymethyl-3-methyl-butylcarbamoyl)-cyclohexyl]-amide (0.328 g, 0.82 mmol) was added to 6 mL of dry DMSO. Triethylamine (0.46 mL, 3.28 mmol) was added followed by sulfur trioxide pyridine complex (0.52 g, 3.28 mmol) and the mixture was stirred at room temperature for a half hour. The mixture was poured into 100 mL of ice water and extracted twice with ethyl acetate. The ethyl acetate extracts were rinsed twice with a 10% citric acid solution, twice with water and once with saturated aqueous sodium bicarbonate and dried over sodium sulfate. Concentration in vacuo gave 0.311 g (0.78 mmol) of 1-methyl-1H-indole-2-carboxylic acid [(1S,2R)-2-((S)-1-formyl-3-methyl-butylcarbamoyl)-cyclohexyl]-amide as a solid.

Method G

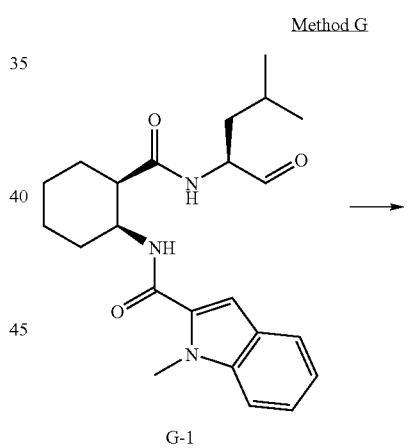

G-1

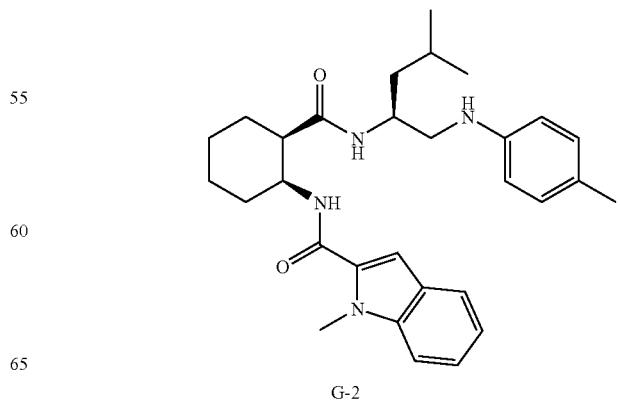

G-2

The aldehyde G-1 (0.10 g, 0.25 mmol), 4-methylaniline (0.030 g, 0.28 mmol), acetic acid (0.018 mL, 0.3 mmol) and 4 Å molecular sieves (0.6 g) were added to 5 mL of methanol and stirred for 30 minutes at room temperature. Sodium cyanoborohydride (0.018 g, 0.286 mmol) was added and the mixture was stirred overnight. The mixture was filtered, concentrated in vacuo, and the residue was diluted with aqueous sodium bicarbonate. The mixture is extracted twice with ethyl acetate, dried over magnesium sulfate and concentrate in vacuo to provide an oil. The oil was purified on a preparative TLC plate to give 1-methyl-1H-indole-2-carboxylic acid {(1S,2R)-2-[(S)-3-methyl-1-(p-tolylaminomethyl)-butylcarbamoyl]-cyclohexyl}-amide (0.058 g, 0.12 mmol).

Method H

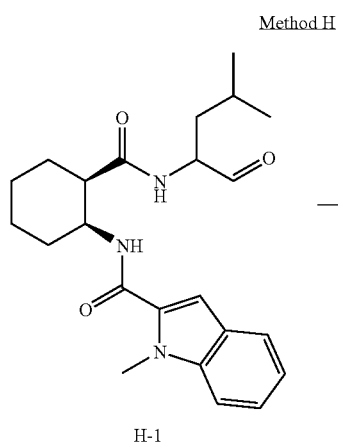

H-1

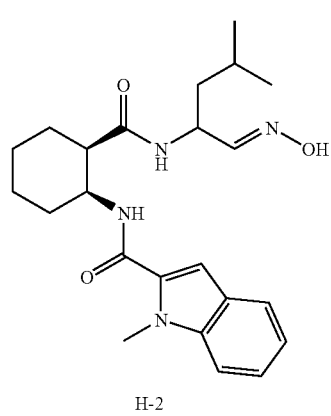

H-2

The aldehyde H-1 (100 mg, 0.25 mmol), 4-phenylsemicarbazide (45 mg, 0.30 mmol) and acetic acid (20 µL, 0.35 mmol) were added to 3 mL of methanol and stirred at room temperature. After several hours at room temperature the reaction mixture is concentrated under vacuum. Ethyl acetate was added, the solution was rinsed 3× with 0.01M HCl aqueous solution, dried over magnesium sulfate filtered and stripped and purified on preparative TLC plate to give 1-methyl-1H-indole-2-carboxylic acid ((1S,2R)-2-{1-[(anilinocarbonyl)hydrazono-methyl]-3-methyl-butylcarbamoyl}-cyclohexyl)-amide (60 mg, 0.11 mmol).

Method I

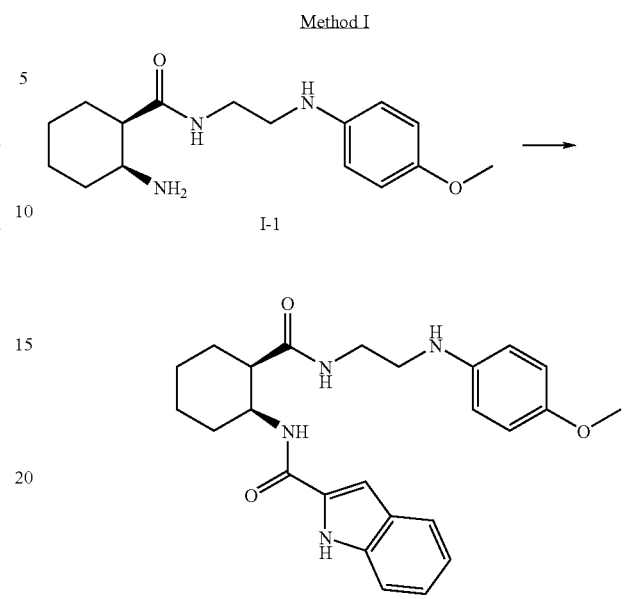

2-Amino-cyclohexanecarboxylic I-2 acid [2-(4-methoxy-phenylamino)-ethyl]-amide (0.100 g, 0.343 mmol) was added to 1.1 mL of DMF. Benzotriazol-1-yl-oxytrispyrrolidinophosphonium hexafluorophosphate (0.196 g, 0.377 mmol), N,N-diisopropylethylamine (0.08 mL, 0.446 mmol) and 1H-indole-2-carboxylic acid (0.066 g, 0.412 mmol) were added and the reaction mixture was stirred at room temperature. The reaction mixture diluted with ethyl acetate and washed successively with saturated aqueous sodium bicarbonate and 1 M hydrochloric acid solution. The organic layer was dried over magnesium sulfate and concentrated in vacuo to yield 0.051 g (0.12 mmol) of 1H-indole-2-carboxylic acid {2-[2-(4-methoxy-phenylamino)-ethylcarbamoyl-cyclohexyl]-amide as a solid.

Method J

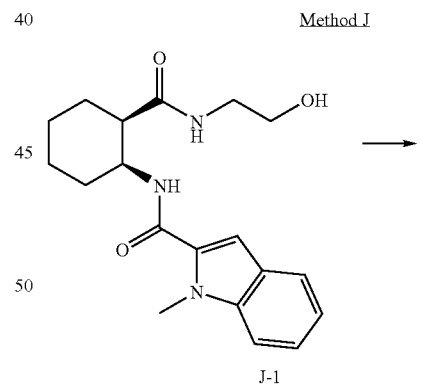

J-1

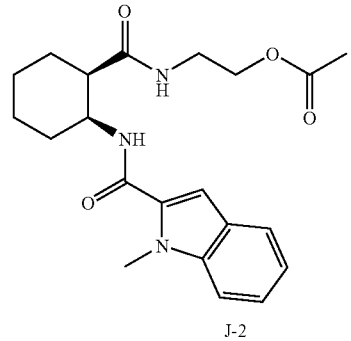

J-2

A solution of 1-methyl-1H-indole-2-carboxylic acid [2-(2-hydroxy-ethylcarbamoyl)-cyclohexyl]-amide (0.128 g, 0.37 mmol), acetyl chloride (29 µL, 0.41 mmol), and triethylamine (57 µL, 0.41 mmol) in 2 mL of THF was stirred at room temperature over night. The mixture was filtered and concentrated in vacuo. The resulting residue was dissolved in sat. aqueous sodium bicarbonate solution and extracted with ethyl acetate. The organic phases were combined, dried over magnesium sulfate, and concentrated. The crude material was purified by column chromatography (30:70, ethyl acetate:hexane) to yield 80 mg of the desired product, MS: 386 (M+H$^+$).

Method K

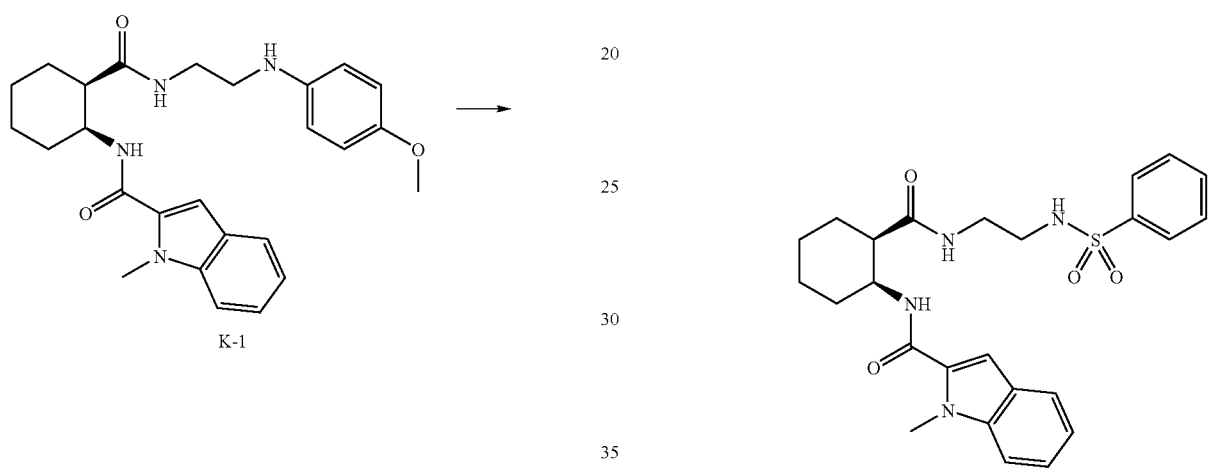

K-1

K-2

Sodium tris-acetoxy borohydride (120 mg, 1.4 mmol) was added to a solution of (1-methyl-1H-indole-2-carboxylic acid {2-[2-(4-methoxy-phenylamino)-ethylcarbamoyl]-cyclohexyl}-amide (180 mg, 1 mmol) and formaldehyde (30 µL, 1 mmol) in 15 mL of dichloromethane. The mixture was stirred under nitrogen at room temperature over night. Sat. aqueous sodium bicarbonate was added and extracted with ethyl acetate. The organic layers were combined, dried over magnesium sulfate and concentrated. The crude material was purified by column chromatography (1:1, ethyl acetate: hexane) to yield 110 mg of the desired product, MS: 463 (M+H$^+$).

Method L

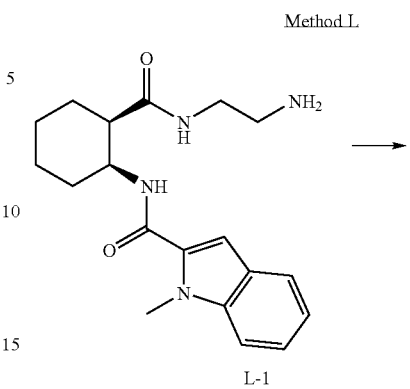

L-1

L-2

1-Methyl-1H-indole-2-carboxylic acid [2-(2-amino-ethylcarbamoyl)-cyclohexyl]-amide (200 mg, 0.59 mmol) was dissolved in 3 mL of DMF. To this solution was added NMM (129 µL, 1.2 mmol), 4-DMAP (8 mg, 0.06 mmol), and benzenesulfonyl chloride (75 µL, 0.59 mmol) and stirred at room temperature over night. Water was added and the mixture extracted with ethyl acetate. The organic layers were separated, combined, and washed successively with water, 1N HCl and brine. The organic layer was dried over magnesium sulfate and concentrated in vacuo to yield 226 mg of the desired product, MS: 483 (M+H$^+$).

Method M

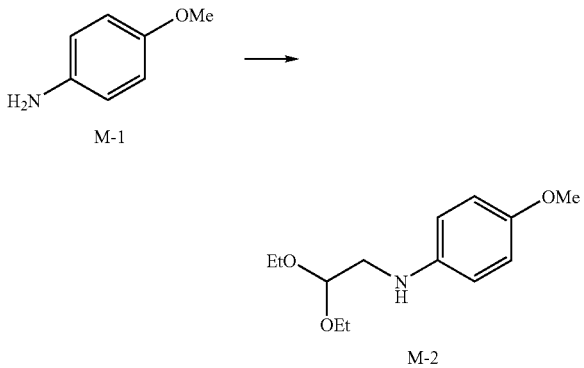

M-1

M-2 p-Anisidine (4.45 g, 36.1 mmol), bromoacetaldehyde diethylacetal (5.95 mL, 39.6 mmol), and potassium carbonate (5.13 g, 37.1 mmol) were placed in a flask containing 25 mL of NMP. The reaction mixture was placed in a 95° C. oil bath for 4 hrs. An additional amount of potassium carbonate (1.5 g, 10.9 mmol) and bromoacetaldehyde diethylacetal (0.5 mL, 3.32 mmol) were added and the reaction mixture was stirred at 95° C. under a N$_2$ atmosphere overnight. The cooled reaction mixture was partitioned between 150 mL of water and 150 mL of ethyl acetate. The organic layer was washed with water (2×150 mL), dried over sodium sulfate, filtered, concentrated, and purified by column chromatography (30-40:70-60, ethyl acetate:hexanes) to give 5.33 g of the product as a yellow liquid. Yield: 62%, MS: 240 (M+H$^+$).

Method N

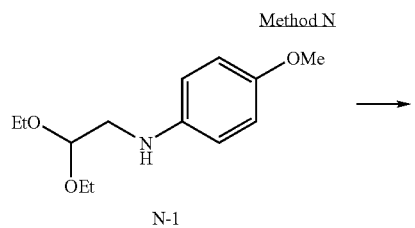

N-1

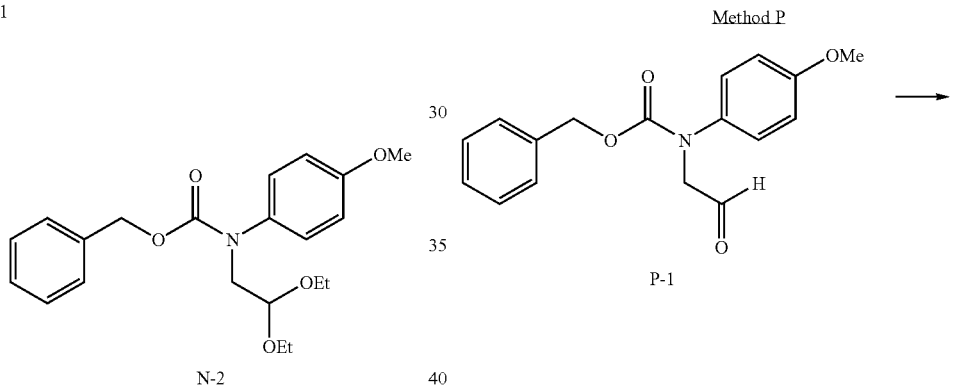

To a 0° C. solution of the acetal N-1 (5.33 g, 22.3 mmol) in 50 mL of dichloromethane was added benzylchloroformate (3.50 mL, 24.5 mmol) and 50 mL of aqueous sodium bicarbonate solution. The reaction mixture was placed into a 50° C. oil bath for 2 hrs. The cooled reaction mixture was partitioned between 150 mL of water and 150 mL of dichloromethane. The organic layer was washed with 150 mL of water, dried over sodium sulfate, filtered, concentrated, and purified by column chromatography (10-30:90-70, ethyl acetate:hexanes) to give 6.49 g of the product as a light tan-colored liquid. Yield: 78%, MS: 396 (M+Na$^+$).

Method O

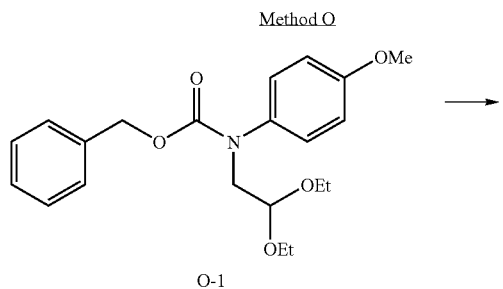

O-1

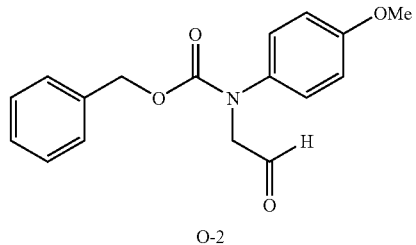

O-2

To a solution of the acetal O-1 (6.49 g, 17.4 mmol) in 100 mL of THF was added 100 mL of a 1N aqueous hydrochloric acid solution. The reaction mixture was refluxed for 2 hrs, cooled and partitioned between 200 mL of diethyl ether and 200 mL of water. The organic layer was washed with 200 mL of water, dried over sodium sulfate, filtered, concentrated and purified by column chromatography (30-40:70-60, ethyl acetate:hexanes) to give 4.24 g of the product as a clear liquid. Yield: 81%, MS: 300 (M+H$^+$).

Method P

P-1

P-2

To a 0° C. solution of sodium cyanide (1.70 g, 34.7 mmol) and ammonium chloride (1.97 g, 36.8 mmol) in 50 mL of ammonium hydroxide was added a solution of the aldehdye P-1 (5.00 g, 16.7 mmol) in 25 mL of methanol dropwise via an addition funnel. The reaction mixture was stirred at ambient temperature overnight, and partitioned between 300 mL of dichloromethane and 300 mL of water. The organic layer was washed with 300 mL of water, dried over sodium sulfate, filtered, concentrated, and purified by column chromatography (30-100:70-0, ethyl acetate:hexanes) to give 3.52 g of the product as a yellow liquid. Yield: 65%, MS: 326 (M+H$^+$).

Method Q

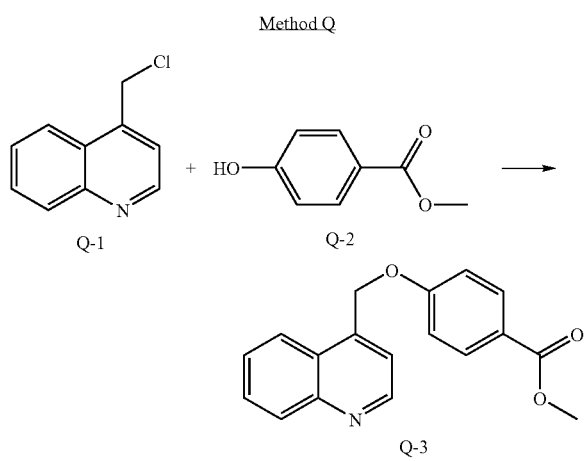

Sodium hydride (430 mg, 60%, 10.75 mmol) was placed in a flask with hexane and stirred under nitrogen. After 10 minutes the hexane was discarded and 10 ml dry DMF was added. After cooling to 0° C., 4-hydroxy-benzoic acid methyl ester Q-2 (1.67 g, 11 mmol) was added and the mixture stirred for 15 minutes. 4-Chloromethyl-quinoline Q-1 (1.8 g, 10.1 mmol) was dissolved in 3 mL of DMF and added dropwise to the reaction mixture. The temperature was raised to 130° C. and the mixture stirred for a half hour. After cooling to room temperature the reaction mixture was poured into 50 mL 1N sodium hydroxide solution and extracted three times with 20 mL dichloromethane. The combined organic layers were washed twice with water, dried over sodium sulfate and concentrated in vacuo. The crude product (2.5 g) was recrystallized from ethyl ether to give 4-(quinolin-4-ylmethoxy)-benzoic acid methyl ester (1.6 g, 5.45 mM) as a white solid.

Method R

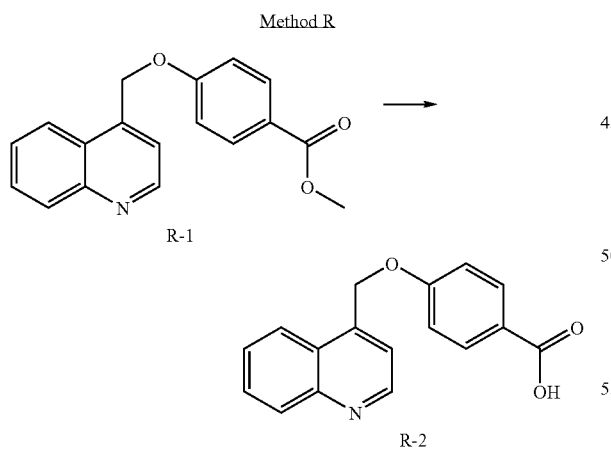

The methyl ester R-1 (1.6 g, 5.45 mmol) was dissolved in 50 mL of methanol, and the resulting solution was heated to reflux. To the reaction mixture was added dropwise 11 mL of 2.5 N sodium hydroxide solution. The mixture was refluxed 2 hours and cooled to room temperature. To the mixture was added 150 mL of ethyl acetate and 75 mL of water. The aqueous layer was brought to pH 6 and extracted twice with 100 mL of ethyl acetate. The organic layer was dried over sodium sulfate and concentrated in vacuo to give 4-(quinolin-4-ylmethoxy)-benzoic acid (0.554 g, 2 mmol) as a white powder.

Method S

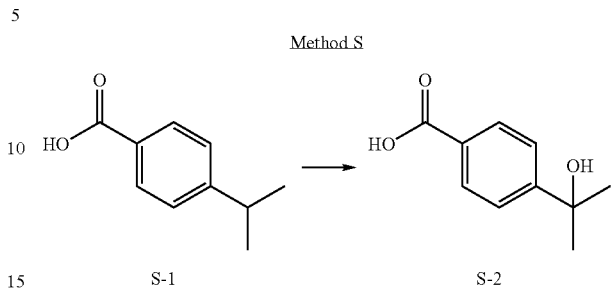

4-Isopropyl-benzoic acid (5.00 g, 30.0 mmol) was dissolved in 20 mL of 10% potassium hydroxide in water solution. To this solution was added 480 mL of 0.2 N aqueous potassium hydroxide solution, followed by a solution of potassium permanganate (9.65 g, 60.0 mmol) in 500 mL of water. The mixture was stirred at 70° C. for one hour. To the reaction mixture was added a few drops of glycerol, and the resulting mixture was cooled to 0° C. Solid residues were removed by filtration, and the filtrate was acidified to pH 1 and extracted twice with ether. The ether extracts were combined, rinsed once with brine and dried over magnesium sulfate and concentrated in vacuo. The concentrate was washed with carbon tetrachloride and recrystallized from water to give 2.2 g (12.2 mmol) of 4-(1-hydroxy-1-methyl-ethyl)-benzoic acid.

Method T

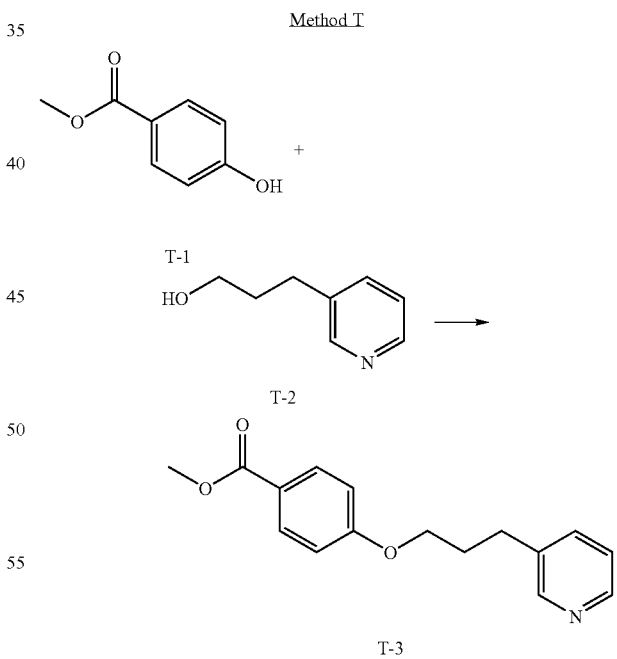

Diethyl azodicarboxylate (1.14 mL, 7.23 mmol) was added to a solution of 4-hydroxy-benzoic acid methyl ester (1 g, 6.57 mmol), 4-(3-pyridin-3-yl-propoxy)-benzoic acid methyl ester (902 mg, 6.57 mmol), triphenyl phosphine (1.9 g, 7.23 mmol) in 35 mL of THF. The mixture was stirred at room temperature over night. The mixture was concentrated in vacuo and the residue was dissolved in acidified water, and washed with ethyl acetate. The aqueous layer was basified with 10% sodium hydroxide and extracted with ethyl acetate to obtain 2.19 g of the crude material which was used without further purification (MS: 272 (M+H$^+$).

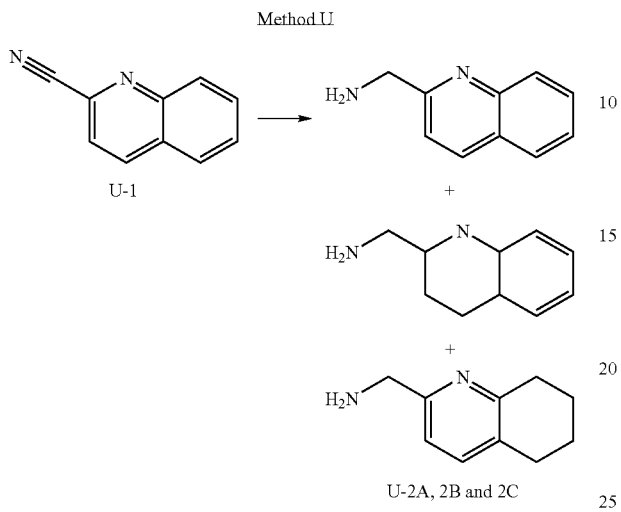

Quinoline-2-carbonitrile U-1 (1 g, 6.5 mmol) was dissolved in 50 mL of methanol and 1.5 mL of conc. HCl. Under atmospheric pressure, the mixture was hydrogenated with 0.71 g of 10% Pd/C over night. The mixture was filtered through celite and the filtrate was concentrated to obtain 1.3 g of a mixture of three products as HCl salts MS: 159 (M+H$^+$). MS: 163 (M+H$^+$). This mixture was used in the next step without further purification.

Example 2

This example illustrates inhibitory activity of some of the compounds of the present invention against Cathepsin K, S, L and B.

The inhibitory activity of the compounds against cathepsin K, S, L and B was tested at room temperature in 96-wells opaque white polystyrene plates (Costar). The cathepsin K inhibitory activity was tested as follows:
5 μL of a compound of the present invention diluted in 5 mM of sodium phosphate, 15 mM of NaCl, pH 7.4 solution containing 1% DMSO (final concentrations: 10-0.0001 μM) were preincubated for 10 min with 35 μL of human recombinant cathepsin K (final concentration: 1 nM) diluted in assay buffer (100 nM sodium acetate, pH 5.5, containing 5 mM of EDTA and 20 mM of cysteine). After addition of 10 μL of the fluorogenic substrate Z-Leu-Arg-MCA diluted in assay buffer (final concentration: 5 μM), increase of fluorescence (excitation at 390 nm and emission at 460 nm) was measured for 7.5 min every 45 sec. The initial velocity (RFU/min) was derived from the linear fit of the 11 reading points.

The cathepsin B inhibitory activity was assayed under the same conditions as the cathepsin K inhibitory activity using human liver cathepsin B (Calbiochem) at a final concentration of 1 nM.

The cathepsin L inhibitory activity was assayed under the same conditions as the cathepsin K inhibitory activity using human liver cathepsin L (Calbiochem) at a final concentration of 3 nM.

Cathepsin S inhibitory activity was assayed analogously to the cathepsin K inhibitory activity, except that the buffer was 100 mM potassium phosphate, 5 mM EDTA, 5 mM DTT (freshly added), 0.01% Triton X-100, pH 6.5 and the fluorogenic substrate was Z-Val-Val-Arg-MCA (Bachem) (final concentration: 20 μM). Human recombinant cathepsin S (Wiederanders et al., Eur. J. Biochem. 1997, 250, 745-750) was used at a final concentration of 0.5 nM.

Using the above assays, the compounds of the invention were found to selectively inhibit Catepsin K. For example, the compound 1-Methyl-1H-indole-2-carboxylic acid {(1S, 2R)-2-[2-(4-methoxy-phenylamino)-ethylcarbamoyl]-cyclohexyl}-amide exhibited an IC50 of less than 0.0002 using the above assay.

Example 3

Formulations

Pharmaceutical preparations for delivery by various routes are formulated as shown in the following Tables. "Active ingredient" or "Active compound" as used in the Tables means one or more of the Compounds of Formula I.

| Composition for Oral Administration | |
|---|---|
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

| Composition for Oral Administration | |
|---|---|
| Ingredient | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

| Composition for Oral Administration | |
|---|---|
| Ingredient | Amount |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

Parenteral Formulation

| Ingredient | % wt./wt. |
|---|---|
| Active ingredient | 0.25 g |
| Sodium Chloride | qs to make isotonic |
| Water for injection | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

Suppository Formulation

| Ingredient | % wt./wt. |
|---|---|
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

Topical Formulation

| Ingredients | grams |
|---|---|
| Active compound | 0.2-2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations

Several aqueous suspensions containing from about 0.025-0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50-100 microliters of formulation per actuation. A typical dosing schedule is 2-4 sprays every 4-12 hours.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:

1. A compound of the Formula:

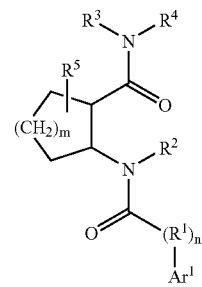

or pharmaceutically acceptable salt thereof,
wherein
m is an integer from 1 to 3;
n is 0 or 1;
$Ar^1$ is 1-methyl-indol-2-yl, indol-2-yl, indol-5-yl or benzothiazolyl;
$R^1$ is alkylene;
each of $R^2$, $R^3$ and $R^5$ is independently hydrogen or alkyl; and
$R^4$ is aralkyl, cycloalkyl, or —CH($R^6$)—$Z^1$, wherein
$R^6$ is hydrogen, or alkyl;
$Z^1$ is —$(CR^7R^8)_p$—$X^1$,
wherein
p is 1 or 2;
$X^1$ is —$OR^{10}$ or —$NR^{10}R^{11}$;
wherein
$R^{10}$ is hydrogen, alkyl or heteroalkyl; and
$R^{11}$ is hydrogen, acetyl, alkyl, aryl, aralkyl, —$S(O)_x$ $Ar^2$, hydroxy, alkoxy, aralkoxy, —C(O)-aryl, —C(O)—O-aralkyl, or heteroalkoxy,
wherein
x is an integer from 0 to 2; and
$Ar^2$ is aryl;
each $R^7$ is independently hydrogen or alkyl;
each $R^8$ is independently hydrogen, alkyl, hydroxy, alkoxy, hydroxyalkyl, alkoxyalkyl or aryl; or
$Z^1$ is —$(CR^9)$=$X^2$; wherein
$X^2$ is O or $NR^{12}$;
wherein
$R^{12}$ is hydrogen, alkyl, alkoxy, aralkoxy, hydroxyalkyl, alkoxyalkyl, hydroxy, or —NH—C(=$X^3$)—$R^{13}$,
wherein
$X^3$ is O or S; and
$R^{13}$ is alkyl, aryl, arylamino, or aralkylamino; and
$R^9$ is hydrogen, alkyl, hydroxy, alkoxy, aralkoxyalkyl, heteroalkyl, heteroalkylamino, aryl, or arylamino.

2. The compound according to claim 1, wherein $Ar^1$ is 1-methyl-1H-indol-2-yl.

3. The compound according to claim 1, wherein $R^4$ is aralkyl, or cycloalkyl.

4. The compound according to claim 3, wherein $R^4$ is selected from the group consisting of:
2-methoxybenzyl;
2-hydroxycyclohexyl;
2-hydroxycyclopentyl;
4-phenylbutyl;
3-phenylpropyl; and
2-phenylethyl.

5. The compound according to claim 1, wherein m is 2.

6. The compound according to claim 1, wherein $R^2$ is hydrogen.

7. The compound according to claim 1, wherein $R^3$ is hydrogen.

8. The compound according to claim 1 of the formula:

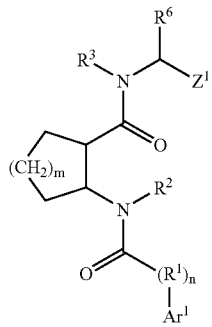

wherein
m, n, $R^1$, $R^2$, $R^3$, $R^6$, $Z^1$, and $Ar^1$ are as defined in claim 1.

9. The compound according to claim 8, wherein $Z^1$ is —$(CR^7R^8)_p$—$X^1$, and wherein p, $R^7$, $R^8$ and $X^1$ are as defined in claim 1.

10. The compound according to claim 8, wherein $Z^1$ is —$(CR^9)$=$X^2$, and wherein $R^9$ and $X^2$ are as defined in claim 8.

11. The compound according to claim 1 selected from the group consisting of:
Acetic acid 2-({(1R,2S)-2-[(1-methyl-1H-indole-2-carbonyl)-amino]-cyclohexanecarbonyl}-amino)-ethyl ester;
({(1R,2S)-2-[(1-Methyl-1H-indole-2-carbonyl)-amino]-cyclohexanecarbonyl}-amino)-acetic acid methyl ester;
({(1R,2S)-2-[(1-Methyl-1H-indole-2-carbonyl)-amino]-cyclohexanecarbonyl}-amino)-acetic acid;
1-Methyl-1H-indole-2-carboxylic acid [(1S,2R)-2-(3-methoxy-2-oxo-propylcarbamoyl)-cyclohexyl]-amide;
1-Methyl-1H-indole-2-carboxylic acid [(1S,2R)-2-((R)-1-formyl-3-methyl-butylcarbamoyl)-cyclohexyl]-amide;
1-Methyl-1H-indole-2-carboxylic acid [(1S,2R)-2-((S)-1-formyl-3-methyl-butylcarbamoyl)-cyclohexyl]-amide;
1-Methyl-1H-indole-2-carboxylic acid [(1S,2R)-2-(2-oxo-propylcarbamoyl)-cyclohexyl]-amide;
1-Methyl-1H-indole-2-carboxylic acid [(1S,2R)-2-((S)-2-oxo-cyclohexylcarbamoyl)-cyclohexyl]-amide;
1-Methyl-1H-indole-2-carboxylic acid [(1S,2R)-2-(2-oxo-ethylcarbamoyl)-cyclohexyl]-amide;
1-Methyl-1H-indole-2-carboxylic acid [(1S,2R)-2-(3-benzyloxy-2-oxo-propylcarbamoyl)-cyclohexyl]-amide;
1-Methyl-1H-indole-2-carboxylic acid {(1S,2R)-2-[2-(3-nitro-phenyl)-2-oxo-ethylcarbamoyl]-cyclohexyl}-amide;
1-Methyl-1H-indole-2-carboxylic acid [(1S,2R)-2-(2-oxo-2-phenyl-ethylcarbamoyl)-cyclohexyl]-amide;
1-Methyl-1H-indole-2-carboxylic acid [(1S,2R)-2-(2-phenoxy-ethylcarbamoyl)-cyclohexyl]-amide;
1-Methyl-1H-indole-2-carboxylic acid [(1S,2R)-2-(2-hydroxy-3-methoxy-propylcarbamoyl)-cyclohexyl]-amide;
1-Methyl-1H-indole-2-carboxylic acid [(1S,2R)-2-(2-methoxy-benzylcarbamoyl)-cyclohexyl]-amide;
1-Methyl-1H-indole-2-carboxylic acid [(1S,2R)-2-((R)-2-hydroxy-propylcarbamoyl)-cyclohexyl]-amide;
1-Methyl-1H-indole-2-carboxylic acid [(1S,2R)-2-((1S,2S)-2-hydroxy-cyclohexylcarbamoyl)-cyclohexyl]-amide;
1-Methyl-1H-indole-2-carboxylic acid [(1S,2R)-2-(2-hydroxy-cyclopentylcarbamoyl)-cyclohexyl]-amide;
1-Methyl-1H-indole-2-carboxylic acid {(1S,2R)-2-[2-(4-methoxy-phenylamino)-ethylcarbamoyl]-cyclohexyl}-amide;
[2-({(1R,2S)-2-[(1-Methyl-1H-indole-2-carbonyl)-amino]-cyclohexanecarbonyl}-amino)-ethyl]-carbamic acid benzyl ester,
1-Methyl-1H-indole-2-carboxylic acid [(1S,2R)-2-(2-amino-ethylcarbamoyl)-cyclohexyl]-amide;
1-Methyl-1H-indole-2-carboxylic acid {(1S,2R)-2-[3-methyl-1-(phenethylamino-methyl)-butylcarbamoyl]-cyclohexyl}-amide;
1-Methyl-1H-indole-2-carboxylic acid {(1S,2R)-2-[1-(benzylamino-methyl)-3-methyl-butylcarbamoyl]-cyclohexyl}-amide;
1-Methyl-1H-indole-2-carboxylic acid ((1S,2R)-2-{1-[(4-methoxy-phenylamino)-methyl]-3-methyl-butylcarbamoyl}-cyclohexyl)-amide;
1-Methyl-1H-indole-2-carboxylic acid [(1S,2R)-2-((S)-3-methyl-1-phenylaminomethyl-butylcarbamoyl)-cyclohexyl]-amide;
1-Methyl-1H-indole-2-carboxylic acid [(1S,2R)-2-(2-benzylamino-ethylcarbamoyl)-cyclohexyl]-amide;
1-Methyl-1H-indole-2-carboxylic acid [(1S,2R)-2-(2-dimethylamino-ethylcarbamoyl)-cyclohexyl]-amide;
1-Methyl-1H-indole-2-carboxylic acid [(1S,2R)-2-(2-phenylamino-ethylcarbamoyl)-cyclohexyl]-amide;
1-Methyl-1H-indole-2-carboxylic acid [(1S,2R)-2-(2-benzoylamino-ethylcarbamoyl)-cyclohexyl]-amide;
1-Methyl-1H-indole-2-carboxylic acid ((1S,2R)-2-{2-[(4-methoxy-phenyl)-methyl-amino]-ethylcarbamoyl}-cyclohexyl)-amide;
1-Methyl-1H-indole-2-carboxylic acid ((1S,2R)-2-{3-methyl-1-[(3-phenyl-propylamino)-methyl]-butylcarbamoyl}-cyclohexyl)-amide;
1-Methyl-1H-indole-2-carboxylic acid ((1S,2R)-2-{3-methyl-1-[(4-phenyl-butylamino)-methyl]-butylcarbamoyl}-cyclohexyl)-amide;
1-Methyl-1H-indole-2-carboxylic acid {(1S,2R)-2-[3-methyl-1-(pyridin-2-ylaminomethyl)-butylcarbamoyl]-cyclohexyl}-amide;
1-Methyl-1H-indole-2-carboxylic acid {(1S,2R)-2-[3-methyl-1-(pyridin-3-ylaminomethyl)-butylcarbamoyl]-cyclohexyl}-amide;
1-Methyl-1H-indole-2-carboxylic acid [(1S,2R)-2-(phenylcarbamoylmethylcarbamoyl)-cyclohexyl]-amide;
1-Methyl-1H-indole-2-carboxylic acid ((1S,2R)-2-{[(4-methoxy-phenylcarbamoyl)-methyl]-carbamoyl}-cyclohexyl)-amide;
N-{(1S,2R)-2-[2-(4-Methoxy-phenylamino)-ethylcarbamoyl]-cyclohexyl}-4-(quinolin-4-ylmethoxy)-benzamide;
1H-Indole-2-carboxylic acid {(1S,2R)-2-[2-(4-methoxy-phenylamino)-ethylcarbamoyl]-cyclohexyl}-amide;
Benzothiazole-6-carboxylic acid {(1S,2R)-2-[2-(4-methoxy-phenylamino)-ethylcarbamoyl]-cyclohexyl}-amide;

1-Methyl-1H-indole-2-carboxylic acid {(1S,2R)-2-[(S)-3-methyl-1-(o-tolylamino-methyl)-butylcarbamoyl]-cyclohexyl}-amide;

1-Methyl-1H-indole-2-carboxylic acid {(1S,2R)-2-[(S)-3-methyl-1-(m-tolylamino-methyl)-butylcarbamoyl]-cyclohexyl}-amide;

1-Methyl-1H-indole-2-carboxylic acid {(1S,2R)-2-[(S)-3-methyl-1-(p-tolylamino-methyl)-butylcarbamoyl]-cyclohexyl}-amide;

1-Methyl-1H-indole-2-carboxylic acid [(1S,2R)-2-((R)-3-methyl-1-phenylaminomethyl-butylcarbamoyl)-cyclohexyl]-amide;

1-Methyl-1H-indole-2-carboxylic acid ((1S,2R)-2-{(S)-1-[(4-chloro-phenylamino)-methyl]-3-methyl-butylcarbamoyl}-cyclohexyl)-amide;

1H-Indole-5-carboxylic acid {(1S,2R)-2-[2-(4-methoxyphenylamino)-ethylcarbamoyl]-cyclohexyl}-amide;

1-Methyl-1H-indole-2-carboxylic acid [(1S,2R)-2-(2-benzenesulfonylamino-ethylcarbamoyl)-cyclohexyl]-amide;

1-Methyl-1H-indole-2-carboxylic acid {(1S,2R)-2-[1-(hydroxyimino-methyl)-3-methyl-butylcarbamoyl]-cyclohexyl}-amide;

1-Methyl-1H-indole-2-carboxylic acid ((1S,2R)-2-{1-[(anilinocarbonyl)hydrazono-methyl]-3-methyl-butylcarbamoyl}-cyclohexyl)-amide;

1-Methyl-1H-indole-2-carboxylic acid [(1S,2R)-2-(1-{[(benzylamino)carbonothioyl]hydrazono-methyl}-3-methyl-butylcarbamoyl)-cyclohexyl]-amide;

1-Methyl-1H-indole-2-carboxylic acid {(1S,2R)-2-[1-(benzyloxyimino-methyl)-3-methyl-butylcarbamoyl]-cyclohexyl}-amide;

1-Methyl-1H-indole-2-carboxylic acid {(1S,2R)-2-[1-(acetyl-hydrazonomethyl)-3-methyl-butylcarbamoyl]-cyclohexyl}-amide;

1-Methyl-1H-indole-2-carboxylic acid ((1S,2R)-2-{1-[(4-chloro-benzoyl)-hydrazonomethyl]-3-methyl-butylcarbamoyl}-cyclohexyl)-amide;

[4-Methyl-2-({(1R,2S)-2-[(1-methyl-1H-indole-2-carbonyl)-amino]-cyclohexanecarbonyl}-amino)-pent-(E)-ylideneaminooxy]-acetic acid;

1-Methyl-1H-indole-2-carboxylic acid {(1S,2R)-2-[1-(methoxyimino-methyl)-3-methyl-butylcarbamoyl]-cyclohexyl}-amide;

1-Methyl-1H-indole-2-carboxylic acid [(1S,2R)-2-(4-phenyl-butylcarbamoyl)-cyclohexyl]-amide;

1-Methyl-1H-indole-2-carboxylic acid [(1S,2R)-2-(3-phenyl-propylcarbamoyl)-cyclohexyl]-amide;

1-Methyl-1H-indole-2-carboxylic acid ((1S,2R)-2-phenethylcarbamoyl-cyclohexyl)-amide; and 1-Methyl-1H-indole-2-carboxylic acid ((1S,2R)-2-{[(2-hydroxy-ethylcarbamoyl)-methyl]-carbamoyl}-cyclohexyl)-amide.

12. A pharmaceutical composition comprising a compound of claim 1 and a pharmaceutically acceptable carrier and/or adjuvant.

13. A pharmaceutical composition comprising a compound of claim 1 and a phosphonic acid or phosphonic ester selected from alendronic acid, cimadronic acid, clodronic acid, tiludronic acid, etidronic acid, ibandronic acid, risedronic acid, pyridronic acid, pamidronic acid, zolendronic acid, or a pharmaceutically acceptable salt or solvate thereof, or mixture thereof.

14. The compound of claim 1, wherein the compound is of formula ID:

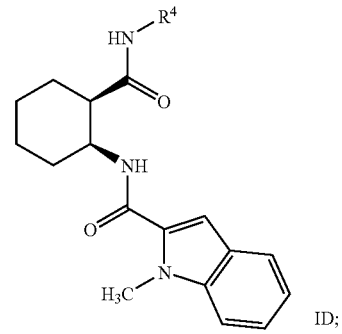

$R^4$ is a group selected from:

t is 1; and $R^a$ is alkyl or alkoxy.

* * * * *